United States Patent
Jorand-Lebrun et al.

(10) Patent No.: US 11,873,303 B2
(45) Date of Patent: Jan. 16, 2024

(54) SUBSTITUTED PYRAZOLES AS TYPE II IRAK INHIBITORS

(71) Applicant: Merck Patent GmbH, Darmstadt (DE)

(72) Inventors: Catherine Jorand-Lebrun, Billerica, MA (US); Nadia Brugger, Billerica, MA (US); Theresa Johnson, Billerica, MA (US)

(73) Assignee: Merck Patent GmbH, Darmstadt (DE)

( * ) Notice: Subject to any disclaimer, the term of this patent is extended or adjusted under 35 U.S.C. 154(b) by 294 days.

(21) Appl. No.: 17/046,751

(22) PCT Filed: Apr. 1, 2019

(86) PCT No.: PCT/EP2019/058186
§ 371 (c)(1),
(2) Date: Oct. 9, 2020

(87) PCT Pub. No.: WO2019/192962
PCT Pub. Date: Oct. 10, 2019

(65) Prior Publication Data
US 2021/0163487 A1    Jun. 3, 2021

Related U.S. Application Data

(60) Provisional application No. 62/652,981, filed on Apr. 5, 2018.

(51) Int. Cl.
| | |
|---|---|
| *A61K 31/4155* | (2006.01) |
| *C07D 231/40* | (2006.01) |
| *C07D 487/04* | (2006.01) |
| *C07D 471/04* | (2006.01) |
| *C07D 495/04* | (2006.01) |

(52) U.S. Cl.
CPC ......... *C07D 487/04* (2013.01); *C07D 471/04* (2013.01); *C07D 495/04* (2013.01)

(58) Field of Classification Search
CPC .......................... A61K 31/4155; C07D 231/40
USPC ........................................ 514/407; 548/373.1
See application file for complete search history.

(56) References Cited

U.S. PATENT DOCUMENTS

| | | |
|---|---|---|
| 7,662,827 B2 | 2/2010 | Hoelzemann et al. |
| 8,008,322 B2 | 8/2011 | Ronan et al. |
| 10,233,189 B2 | 3/2019 | Miyazaki et al. |

FOREIGN PATENT DOCUMENTS

| | | |
|---|---|---|
| WO | 20060108640 A1 | 10/2006 |
| WO | 20120007375 A1 | 1/2012 |
| WO | 2015/068856 A1 | 5/2015 |
| WO | 2017178844 A1 | 10/2017 |
| WO | 2017205762 A1 | 11/2017 |
| WO | 20180006171 A1 | 1/2018 |
| WO | WO-2019192962 A1 * | 10/2019 ........... A61K 31/437 |

OTHER PUBLICATIONS

Jordan, V. C. Nature Reviews: Drug Discovery, 2, 2003, 205.*
Hackam, et al. JAMA, 296(14), 2006, 1731-1732.*
S. M. Berge et al., J. Pharmaceutical Sciences, 66, 1-19 (1977).
Buckley et al. Bioorg Med Chem Lett. 18(12):3656-60 (2008).
Cao et al., Science 271(5252): 1128-31 (1996).
Cohen, Current Opinion in Cell Biology 21, 317-324 (2009).
Foster, Adv. Drug Res. 14, 1-40 (1985).
Gillette et al., Biochemistry 33(10) 2927-2937 (1994).
Hanzlik et al., J. Org. Chem. 55, 3992-3997 (1990).
Jarman et al., Carcinogenesis 16(4), 683-688 (1993).
Li et al. Proc. Natl. Acad. Sci. USA 99(8):5567-5572 (2002).
Muzio et al., Science 278(5343): 1612-5 (1997).
Reider et al., J. Org. Chem. 52, 3326-3334 (1987).
Ringwood and Li, Cytokine 42, 1-7 (2008).
Wesche et al. J. Biol. Chem. 274(27): 19403-10 (1999).
Zhulun Wang et al., IRAK-4 Inhibitors for Inflammation. Current Topics in Medicinal Chemistry, 2009, 9(8):724-737.
Translation of JP Office Action dated Mar. 7, 2023.

* cited by examiner

*Primary Examiner* — Douglas M Willis
(74) *Attorney, Agent, or Firm* — Nicholas J. Sisti; EMD Serono Research and Development Institute, Inc.

(57) ABSTRACT

The present invention relates to compounds of Formula I and pharmaceutically acceptable compositions thereof, useful as IRAK inhibitors.

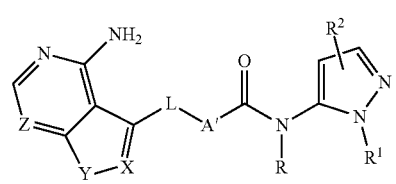

13 Claims, No Drawings

SUBSTITUTED PYRAZOLES AS TYPE II IRAK INHIBITORS

RELATED APPLICATIONS

This application is a US national stage application of PCT international application PCT/EP2019/058186, filed on Apr. 1, 2019, which claims the benefit of U.S. Provisional Application 62/652,981, filed Apr. 5, 2018. The entire contents of the aforementioned applications are, herein, incorporated by reference.

TECHNICAL FIELD OF THE INVENTION

The present invention provides for compounds of Formula (I) as IRAK inhibitors and their use in the treatment of cancer, and other diseases related to IRAK overexpression, including inflammatory disorders, autoimmune disorders, and cancer.

BACKGROUND OF THE INVENTION

Kinases catalyze the phosphorylation of proteins, lipids, sugars, nucleosides and other cellular metabolites and play key roles in all aspects of eukaryotic cell physiology. Especially, protein kinases and lipid kinases participate in the signaling events which control the activation, growth, differentiation and survival of cells in response to extracellular mediators or stimuli such as growth factors, cytokines or chemokines. In general, protein kinases are classified in two groups, those that preferentially phosphorylate tyrosine residues and those that preferentially phosphorylate serine and/or threonine residues.

Kinases are important therapeutic targets for the development of anti-inflammatory drugs (Cohen, 2009. Current Opinion in Cell Biology 21, 1-8), for example kinases that are involved in the orchestration of adaptive and innate immune responses. Kinase targets of particular interest are members of the IRAK family.

IRAKs (IL-1 receptor associated kinases) are Ser/Thr kinases signaling downstream of TNF-R, IL-1β-R, IL-18R and toll-like receptors. IRAKs in turn mediate JNK/p38 and NFκB activation, leading to pro-inflammatory cytokine production. From four family members only IRAK1 and 4 possess kinase activity, where IRAK4 acts upstream of IRAK1 within the same pathway. In myeloid cells IRAK1 is required for LPS-induced IL-8 and INF-γ release, STAT3 activation, IL10 release and β2-integrin-mediated cell spreading. In pDC's, IRAK mediates TLR7 and 9-induced release of INF-α. In T cells, IRAK mediates IL-2 production and proliferation, as well as IL-18-induced Th1 cell proliferation and INF-γ production. Expression of IRAKs is particularly high in endothelium, epithelium, macrophages, monocytes, mast cells, granulocytes, dendritic cells, B, T and NK cells. Mice deficient in IRAK-1 or 4 present impaired INF-α production in response to TLR7/9 activation, fail to activate NFκB in response to IL-18 or IL-1, present a drastic decrease in INF-γ production by Th1 and NK cells. They are also protected in models of LPS-induced cardiac failure, CIA, Carageenan, lung inflammation and fibrosis and MOG-induced EAE. IRAK1 phosphorylation is enhanced upon LPS treatment of synoviocytes from RA patients. SNP's in IRAK1 are associated with SLE.

The interleukin-1 receptor-associated kinases (IRAKs) are critically involved in the regulation of intracellular signaling networks controlling inflammation (Ringwood and Li, 2008. Cytokine 42, 1-7). IRAKs are expressed in many cell types and can mediate signals from various cell receptors including toll-like receptors (TLRs). IRAK4 is thought to be the initial protein kinase activated downstream of the interleukin-1 (IL-1) receptor and all toll-like-receptors (TLRs) except TLR3, and initiates signaling in the innate immune system via the rapid activation of IRAK1 and slower activation of IRAK2. IRAK1 was first identified through biochemical purification of the IL-1 dependent kinase activity that co-immunoprecipitates with the IL-1 type 1 receptor (Cao et al., 1996. Science 271(5252): 1128-31). IRAK2 was identified by the search of the human expressed sequence tag (EST) database for sequences homologous to IRAKI (Muzio et al., 1997. Science 278 (5343): 1612-5). IRAK3 (also called IRAKM) was identified using a murine EST sequence encoding a polypeptide with significant homology to IRAK1 to screen a human phytohemagglutinin-activated peripheral blood leukocyte (PBL) cDNA library (Wesche et al., 1999. J. Biol. Chem. 274(27): 19403-10). IRAK4 was identified by database searching for IRAK-like sequences and PCR of a universal cDNA library (Li et al., 2002. Proc. Natl. Acad. Sci. USA 99(8):5567-5572).

Mice that express a catalytically inactive mutant of IRAK4 instead of the wild-type kinase are completely resistant to septic shock triggered by several TLR agonists and are impaired in their response to IL-1. Children who lack IRAK4 activity due to a genetic defect suffer from recurring infection by pyogenic bacteria. It appears that IRAK-dependent TLRs and IL-1Rs are vital for childhood immunity against some pyogenic bacteria but play a redundant role in protective immunity to most infections in adults. Therefore IRAK4 inhibitors may be useful for the treatment of chronic inflammatory diseases in adults without making them too susceptible to bacterial and viral infections (Cohen, 2009. Current Opinion in Cell Biology 21, 1-8). Potent IRAK4 inhibitors have been developed (Buckley et al., 2008. Bioorg Med Chem Lett. 18(12):3656-60). IRAK1 is essential for the TLR7-mediated and TLR9-mediated activation of IRF7 and the production of interferon-alpha (IFN-α) suggesting that IRAK1 inhibitors may be useful for the treatment of Systemic lupus erythematosus (SLE). IRAK2 is activated downstream of IRAK4 and plays a role in proinflammatory cytokine production. Therefore IRAK2 inhibitors may be useful for inflammatory diseases.

SUMMARY OF THE INVENTION

In one aspect, the invention provides a compound of Formula (I):

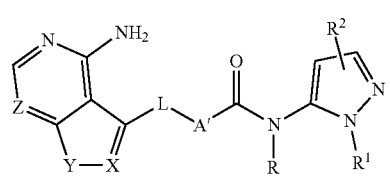

and pharmaceutically acceptable derivatives, solvates, salts, hydrates and stereoisomers thereof, wherein each of A', L, X, Y, Z, $R^1$, and $R^2$, is as defined below and described in the embodiments.

In another aspect, the invention provides compounds of Formula (I) which are suitable for the treatment and/or prevention of disorders related to IRAK. In another aspect, the invention provides compounds which are able to modulate, especially inhibit the activity or function of IRAK in disease states in mammals, especially in humans.

According to another aspect of the invention are provided methods for the treatment and/or prevention of disorders selected from auto-immune, inflammatory disorders, cardiovascular diseases, neurodegenerative disorders, bacterial and viral infections, allergy, asthma, pancreatitis, multiorgan failure, kidney diseases, platelet aggregation, cancer, transplantation, sperm motility, erythrocyte deficiency, graft rejection, lung injuries, respiratory diseases, ischemic conditions, and cancer.

According to another aspect, the present invention provides compounds of Formula (I) which are selective for IRAK-4 and/or IRAK-1, with type II mode of binding.

According to another aspect, the present invention provides compounds of Formula (I) which are selective for IRAK-4 and IRAK-1, with type II mode of binding.

DETAILED DESCRIPTION OF CERTAIN EMBODIMENTS

1. General Description of Compounds of the Invention

In certain aspects, the present invention provides for inhibitors of IRAK. In some embodiments, such compounds include those of the formulae described herein, or a pharmaceutically acceptable salt thereof, wherein each variable is as defined and described herein.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Exemplary aliphatic groups are linear or branched, substituted or unsubstituted $C_1$-$C_8$ alkyl, $C_2$-$C_8$ alkenyl, $C_2$-$C_8$ alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, or phosphorus (including, any oxidized form of nitrogen, sulfur, or phosphorus; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl", "aralkoxy", or "aryloxyalkyl", refers to monocyclic and bicyclic ring systems having a total of five to fourteen ring members, wherein at least one ring in the system is aromatic and wherein each ring in the system contains three to seven ring members. The term "aryl" is used interchangeably with the term "aryl ring". In certain embodiments of the present invention, "aryl" refers to an aromatic ring system. Exemplary aryl groups are phenyl, biphenyl, naphthyl, anthracyl and the like, which optionally includes one or more substituents. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group is optionally mono- or bicyclic. The term "heteroaryl" is used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen is N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group is optionally mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, certain compounds of the invention contain "optionally substituted" moieties. In general, the term "substituted", whether preceded by the term "optionally" or not, means that one or more hydrogens of the designated moiety are replaced with a suitable substituent. "Substituted" applies to one or more hydrogens that are either explicit or implicit from the structure (e.g.,

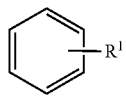

refers to at least

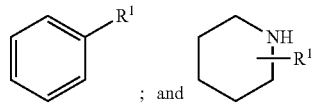

; and refers to at least

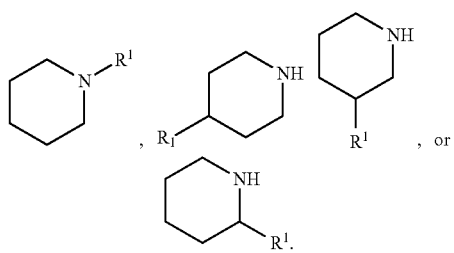

, or

Unless otherwise indicated, an "optionally substituted" group has a suitable substituent at each substitutable position of the group, and when more than one position in any given structure is substituted with more than one substituent selected from a specified group, the substituent is either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently deuterium; halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$ Ph, which is optionally substituted with R°; —(CH$_2$)$_{0-4}$O(CH$_2$)$_{0-1}$Ph which is optionally substituted with R°; —CH=CHPh, which is optionally substituted with R°; —(CH$_2$)$_{0-4}$O(CH$_2$)$_{0-1}$-pyridyl which is optionally substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°, SC(S) SR°, —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°, —(CH$_2$)$_{0-4}$S(O)$_2$R°; —(CH$_2$)$_{0-4}$S(O)$_2$OR°; —(CH$_2$)$_{0-4 0}$ S(O)$_2$R°; —S(O)$_2$NR°)$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched)alkylene)C(O)O—N(R°)$_2$, wherein each R° is optionally substituted as defined below and is independently hydrogen, $C_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which is optionally substituted as defined below.

Suitable monovalent substituents on R° (or the ring formed by taking two independent occurrences of R° together with their intervening atoms), are independently deuterium, halogen, —(CH$_2$)$_{0-2}$R$^●$, -(haloR$^●$), —(CH$_2$)$_{0-2}$OH, —(CH$_2$)$_{0-2}$R$^●$, —(CH$_2$)$_{0-2}$CH(OR$^●$)$_2$; —O(haloR$^●$), —CN, —N$_3$, —(CH$_2$)$_{0-2}$C(O)R$^●$, —(CH$_2$)$_{0-2}$C(O)OH, —(CH$_2$)$_{0-2}$C(O)OR$^●$, —(CH$_2$)$_{0-2}$SR$^●$, —(CH$_2$)$_{0-2}$SH, —(CH$_2$)$_{0-2}$NH$_2$, —(CH$_2$)$_{0-2}$NHR$^●$, —(CH$_2$)$_{0-2}$NR$^●_2$, —NO$_2$, —SiR$^●_3$, —OSiR$^●_3$, —C(O)SR$^●$, —(C$_{1-4}$ straight or branched alkylene)C(O)OR$^●$, or —SSR$^●$ wherein each R$^●$ is unsubstituted or where preceded by "halo" is substituted only with one or more halogens, and is independently selected from $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, $C_{1-6}$ aliphatic which is substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*2)$_{2-3}$O—, wherein each independent occurrence of R* is selected from hydrogen, $C_{1-6}$ aliphatic which is optionally substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^●$, -(haloR$^●$), —OH, —OR$^●$, —O(haloR$^●$), —CN, —C(O)OH, —C(O)OR$^●$, —NH$_2$, —NHR$^●$, —NR$^●_2$, or —NO$_2$, wherein each R$^●$ is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, $C_{1-6}$ aliphatic which is optionally substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of Rt, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R$^●$, -(haloR$^●$), —OH, —OR$^●$, —O(haloR$^●$), —CN, —C(O)OH, —C(O)OR$^●$, —NH$_2$, —NHR$^●$, —NR$^●_2$, or —NO$_2$, wherein each R$^●$ is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

In certain embodiments, the terms "optionally substituted", "optionally substituted alkyl," "optionally substituted "optionally substituted alkenyl," "optionally substituted alkynyl", "optionally substituted carbocyclic," "optionally substituted aryl", "optionally substituted heteroaryl," "optionally substituted heterocyclic," and any other optionally substituted group as used herein, refer to groups that are substituted or unsubstituted by independent replacement of one, two, or three or more of the hydrogen atoms thereon with typical substituents including, but not limited to:

—F, —Cl, —Br, —I, deuterium,

—OH, protected hydroxy, alkoxy, oxo, thiooxo,

—NO$_2$, —CN, CF$_3$, N$_3$,

—NH$_2$, protected amino, —NH alkyl, —NH alkenyl, —NH alkynyl, —NH cycloalkyl, —NH-aryl, —NH-heteroaryl, —NH-heterocyclic, -dialkylamino, -diarylamino, -diheteroarylamino, —O-alkyl, —O-alkenyl, —O-alkynyl, —O-cycloalkyl, —O-aryl, —O-heteroaryl, —O-heterocyclic, —C(O)-alkyl, —C(O)-alkenyl, —C(O)-alkynyl, —C(O)-carbocyclyl, —C(O)-aryl, —C(O)-heteroaryl, —C(O)-heterocyclyl, —CONH$_2$, —CONH-alkyl, —CONH-alkenyl, —CONH-alkynyl, —CONH-carbocyclyl, —CONH-aryl, —CONH-heteroaryl, —CONH-heterocyclyl, —OCO$_2$-alkyl, —OCO$_2$-alkenyl, —OCO$_2$-alkynyl, —OCO$_2$-carbocyclyl, —OCO$_2$-aryl, —OCO$_2$-heteroaryl, —OCO$_2$-heterocyclyl, —OCONH$_2$, —OCONH-alkyl, —OCONH-alkenyl, —OCONH-alkynyl, —OCONH-carbocyclyl, —OCONH-aryl, —OCONH-heteroaryl, —OCONH-heterocyclyl, —NHC(O)-alkyl, —NHC(O)-alkenyl, —NHC(O)-alkynyl, —NHC(O)-carbocyclyl, —NHC(O)-aryl, —NHC(O)-heteroaryl, —NHC(O)-heterocyclyl, —NHCO$_2$-alkyl, —NHCO$_2$-alkenyl, —NHCO$_2$-alkynyl, —NHCO$_2$-carbocyclyl, —NHCO$_2$-aryl, —NHCO$_2$-heteroaryl, —NHCO$_2$-heterocyclyl, —NHC(O)NH$_2$, —NHC(O)NH-alkyl, —NHC(O)NH-alkenyl, —NHC(O)NH-alkenyl, —NHC(O)NH— carbocyclyl, —NHC(O)NH-aryl, —NHC(O)NH-heteroaryl, —NHC(O)NH-heterocyclyl, NHC(S)NH$_2$, —NHC(S)NH-alkyl, —NHC(S)NH-alkenyl, —NHC(S)NH-alkynyl, —NHC(S)NH— carbocyclyl, —NHC(S)NH-aryl, —NHC(S)NH-heteroaryl, —NHC(S)NH-heterocyclyl, —NHC(NH)NH$_2$, —NHC(NH)NH-alkyl, —NHC(NH)NH-alkenyl, —NHC(NH)NH-alkenyl, —NHC(NH)NH— carbocyclyl, —NHC(NH)NH-aryl, —NHC(NH)NH-heteroaryl, —NHC(NH)NH-heterocyclyl, —NHC(NH)-alkyl, —NHC(NH)-alkenyl, —NHC(NH)-alkenyl, —NHC(NH)-carbocyclyl, —NHC(NH)-aryl, —NHC(NH)-heteroaryl, —NHC(NH)-heterocyclyl, —C(NH)NH-alkyl, —C(NH)NH-alkenyl, —C(NH)NH-alkynyl, —C(NH)NH-carbocyclyl, —C(NH)NH-aryl, —C(NH)NH-heteroaryl, —C(NH)NH-heterocyclyl,
—S(O)-alkyl, —S(O)-alkenyl, —S(O)-alkynyl, —S(O)-carbocyclyl, —S(O)-aryl, —S(O)-heteroaryl, —S(O)-heterocyclyl —$SO_2NH_2$, —$SO_2$NH-alkyl, —$SO_2$NH-alkenyl, —$SO_2$NH-alkynyl, —$SO_2$NH-carbocyclyl, —$SO_2$NH-aryl, —$SO_2$NH-heteroaryl, —$SO_2$NH-heterocyclyl,
—$NHSO_2$-alkyl, —$NHSO_2$-alkenyl, —$NHSO_2$-alkynyl, —$NHSO_2$-carbocyclyl, —$NHSO_2$-aryl, —$NHSO_2$-heteroaryl, —$NHSO_2$-heterocyclyl,
—$CH_2NH_2$, —$CH_2SO_2CH_3$,
-mono-, di-, or tri-alkyl silyl,
-alkyl, -alkenyl, -alkynyl, -aryl, -arylalkyl, -heteroaryl, -heteroarylalkyl, -heterocycloalkyl, -cycloalkyl, -carbocyclic, -heterocyclic, polyalkoxyalkyl, polyalkoxy, -methoxymethoxy, -methoxyethoxy, —SH, —S-alkyl, —S-alkenyl, —S-alkynyl, —S-carbocyclyl, —S-aryl, —S-heteroaryl, —S-heterocyclyl, or methylthiomethyl.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$- enriched carbon are within the scope of this invention. In some embodiments, the group comprises one or more deuterium atoms.

There is furthermore intended that a compound of the formula I includes isotope-labeled forms thereof. An isotope-labeled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phos-phorus, fluo-rine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. A compound of the formula I, a prodrug, thereof or a pharmaceutically acceptable salt of either which contains one or more of the above-mentioned isotopes and/or other isotopes of other atoms is intended to be part of the present invention. An isotope-labeled compound of the formula I can be used in a number of beneficial ways. For example, an isotope-labeled compound of the formula I into which, for example, a radioisotope, such as $^3H$ or $^{14}C$, has been incorporated, is suitable for medicament and/or substrate tissue distribution assays. These radioisotopes, i.e. tritium ($^3H$) and carbon-14 ($^{14}C$), are particularly preferred owing to simple preparation and excellent detectability. Incorporation of heavier isotopes, for example deuterium ($^2H$), into a compound of the formula I has therapeutic advantages owing to the higher metabolic stability of this isotope-labeled compound. Higher metabolic stability translates directly into an increased in vivo half-life or lower dosages, which under most circumstances would represent a preferred embodiment of the present invention. An isotope-labeled compound of the formula I can usually be prepared by carrying out the procedures disclosed in the synthesis schemes and the related description, in the example part and in the preparation part in the present text, replacing a non-isotope-labeled reactant by a readily available isotope-labeled reactant.

Deuterium ($^2H$) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D=2-7$ are typical. If this rate difference is successfully applied to a com-pound of the formula I that is susceptible to oxidation, the profile of this compound in vivo can be drastically modified and result in improved pharmacokinetic properties.

When discovering and developing therapeutic agents, the person skilled in the art is able to optimize pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of compounds of the formula I are thereby obtained, and can be expressed quantitatively in terms of increases in the in vivo half-life (t/2), concentration at maximum therapeutic effect ($C_{max}$), area under the dose response curve (AUC), and F; and in terms of reduced clearance, dose and materials costs.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favorable and accurate determination of the extent of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound of the formula I can also be used to achieve a favorable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

As used herein, the term "modulator" is defined as a compound that binds to and/or inhibits the target with measurable affinity. In certain embodiments, a modulator has an $IC_{50}$ and/or binding constant of less about 50 µM, less than about 1 µM, less than about 500 nM, less than about 100 nM, or less than about 10 nM.

The terms "measurable affinity" and "measurably inhibit," as used herein, means a measurable change in IRAK activity between a sample comprising a compound of the present invention, or composition thereof, and IRAK, and an equivalent sample comprising IRAK, in the absence of said compound, or composition thereof.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

3. Description of Exemplary Compounds

According to one aspect, the present invention provides a compound of formula I,

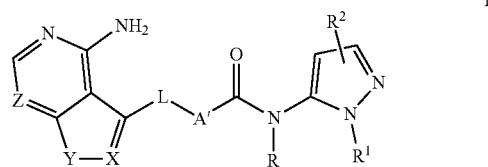

or a pharmaceutically acceptable salt thereof, wherein:
A' is C=O, C(R)$_2$ or NR;
L is a divalent group selected from $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;
X is CR or N;
Y is NR or S;
Z is CR or N;
$R^1$ is $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;
$R^2$ is —R, halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;
each R is independently hydrogen, $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or
two R groups on the same atom are taken together with the atom to which they are attached to form a $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, A' is C=O. In certain embodiments, A' is C(R)$_2$. In certain embodiments, A' is NR.

In certain embodiments, A' is C=O, CH$_2$, CHOH, or NH.

In certain embodiments, A' is C=O. In certain embodiments, A' is CH$_2$. In certain embodiments, A' is CHOH. In certain embodiments, A' is NH.

In certain embodiments, L is a divalent optionally substituted C$_{3-10}$ aryl. In certain embodiments, L is a divalent optionally substituted 3-8 membered saturated or partially unsaturated carbocyclic ring. In certain embodiments, L is a divalent optionally substituted 3-7 membered heterocylic ring having 1-4 heteroatoms independently selected from nitrogen, oxygen, or sulfur. In certain embodiments, L is a divalent optionally substituted 5-6 membered monocyclic heteroaryl ring having 1-4 heteroatoms independently selected from nitrogen, oxygen, or sulfur.

In certain embodiments, L is a divalent group selected from phenyl, naphthyl, cyclopropyl, cyclobutyl, cyclopentyl, cyclohexyl, cyclohexenyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, and xanthenyl; each of which is optionally substituted.

In certain embodiments, L is a divalent group selected from phenyl, cyclopentyl, cyclohexyl, cyclohexenyl, cycloheptyl, furanyl, furazanyl, imidazolidinyl, imidazolinyl, imidazolyl, 1H-indazolyl, indolenyl, isoxazolyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, piperazinyl, piperidinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, 2H-pyrrolyl, pyrrolyl, tetrahydrofuranyl, thiazolyl, thienyl, thiophenyl, oxetanyl, and azetidinyl, each of which is optionally substituted.

In certain embodiments, L is a divalent group selected from phenyl, cyclohexyl, and cyclohexenyl; each of which is optionally substituted.

In certain embodiments, L is a divalent group selected from

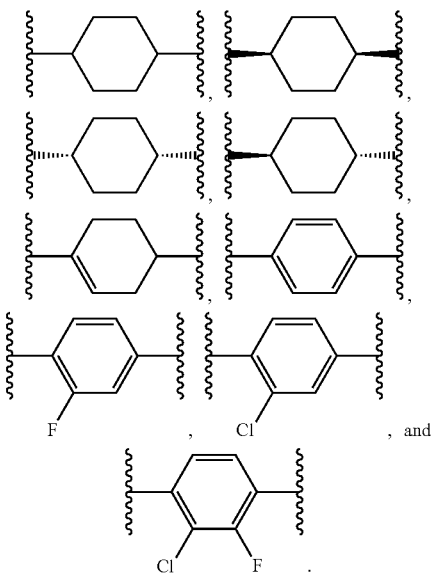

In certain embodiments, in the definitions of L provided above, each group may face the direction as shown, or the reverse direction (e.g.,

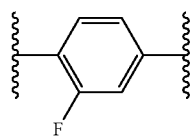 [SMILES: *c1ccc(*)c(F)c1]

represents both

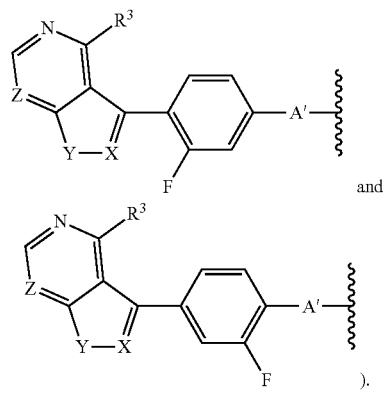

In certain embodiments, X is CR. In certain embodiments, X is CH. In certain embodiments, X is N.

In certain embodiments, Y is NR. In certain embodiments, Y is NMe. In certain embodiments, Y is S.

In certain embodiments, Z is CR. In certain embodiments, Z is CH. In certain embodiments, Z is N.

In certain embodiments, Z is N, Y is NR, and X is CR.
In certain embodiments, Z is N, Y is NR, and X is N.
In certain embodiments, Z is N, Y is S, and X is CR.
In certain embodiments, Z is CR, Y is NR, and X is N.
In certain embodiments, R$^1$ is C$_{3-10}$ aryl.
In certain embodiments, R$^1$ is

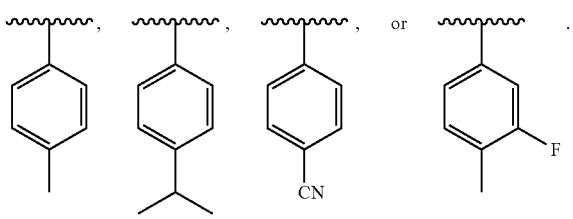

In certain embodiments, R$^2$ is C$_{1-6}$ aliphatic, C$_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, R$^2$ is C$_{1-6}$ aliphatic.

In certain embodiments, R$^2$ is C$_{3-10}$ aryl.

In certain embodiments, R$^2$ is a 3-8 membered saturated or partially unsaturated carbocyclic ring.

In certain embodiments, R$^2$ is a 3-7 membered heterocylic ring having 1-4 heteroatoms independently selected from nitrogen, oxygen, or sulfur.

In certain embodiments, R$^2$ is a 5-6 membered monocyclic heteroaryl ring having 1-4 heteroatoms independently selected from nitrogen, oxygen, or sulfur In certain embodiments, R$^2$ is C$_{1-6}$ aliphatic or 3-7 membered heterocylic ring having 1-4 heteroatoms independently selected from nitrogen, oxygen, or sulfur.

In certain embodiments, R$^2$ is methyl, ethyl, propyl, i-propyl, n-butyl, i-butyl, t-butyl, straight chain or branched pentyl, or straight chain or branched hexyl, or R$^2$ is a 4 membered heterocylic ring having 1-4 heteroatoms independently selected from nitrogen, oxygen, or sulfur.

In certain embodiments, R$^2$ is —CF$_3$,

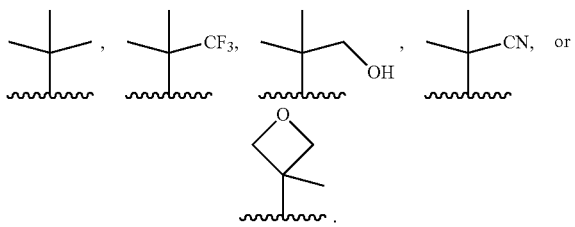

In certain embodiments, each of A', L, X, Y, Z, R, R$^1$, and R$^2$, is as defined above and described in embodiments, classes and subclasses above and herein, singly or in combination.

In certain embodiments, the present invention provides a compound of formula I-a,

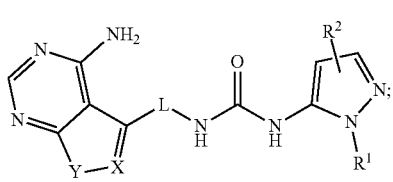

or a pharmaceutically acceptable salt thereof, wherein each of L, X, Y, R$^1$, and R$^2$ is as defined above and described in embodiments, classes and subclasses above and herein, singly or in combination.

In certain embodiments, the present invention provides a compound of formula I-b,

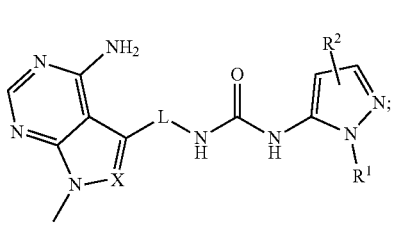

or a pharmaceutically acceptable salt thereof, wherein each of L, X, R$^1$, and R$^2$ is as defined above and described in embodiments, classes and subclasses above and herein, singly or in combination.

In certain embodiments, the present invention provides a compound of formula I-c,

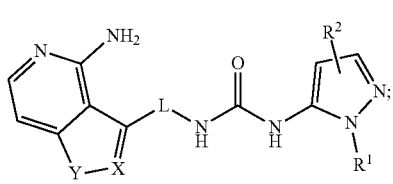

or a pharmaceutically acceptable salt thereof, wherein each of L, X, Y, R$^1$, and R$^2$ is as defined above and described in embodiments, classes and subclasses above and herein, singly or in combination.

In certain embodiments, the present invention provides a compound of formula I-d,

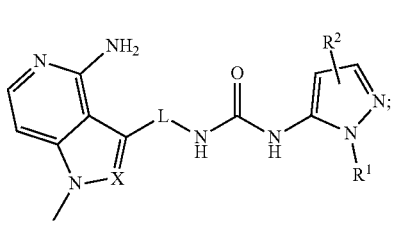

or a pharmaceutically acceptable salt thereof, wherein each of L, X, R$^1$, and R$^2$ is as defined above and described in embodiments, classes and subclasses above and herein, singly or in combination.

In certain embodiments, the present invention provides a compound of formula I-e,

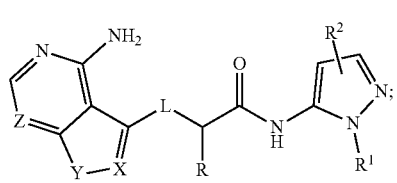

I-e or a pharmaceutically acceptable salt thereof, wherein each of L, X, Y, Z, R$^1$, and R$^2$ is as defined above and described in embodiments, classes and subclasses above and herein, singly or in combination.

In certain embodiments, the present invention provides a compound of formula I-f,

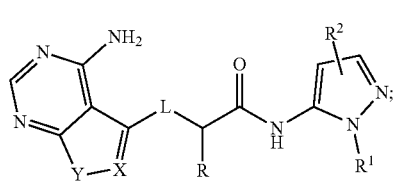

I-f or a pharmaceutically acceptable salt thereof, wherein each of L, X, Y, R$^1$, and R$^2$ is as defined above and described in embodiments, classes and subclasses above and herein, singly or in combination.

In certain embodiments, the present invention provides a compound of formula I-g,

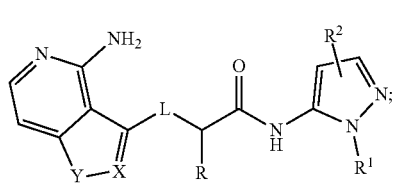

I-g or a pharmaceutically acceptable salt thereof, wherein each of L, X, Y, R$^1$, and R$^2$ is as defined above and described in embodiments, classes and subclasses above and herein, singly or in combination.

In certain embodiments, the present invention provides a compound of formula I-h,

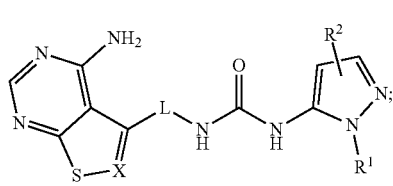

I-h or a pharmaceutically acceptable salt thereof, wherein each of L, X, R$^1$, and R$^2$ is as defined above and described in embodiments, classes and subclasses above and herein, singly or in combination.

In certain embodiments, the present invention provides a compound of formula I-j,

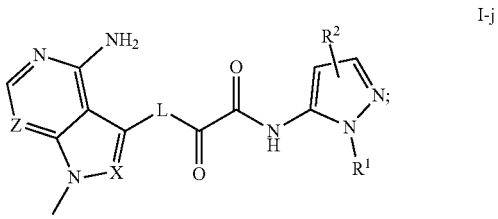

I-j or a pharmaceutically acceptable salt thereof, wherein each of L, X, Z, R$^1$, and R$^2$ is as defined above and described in embodiments, classes and subclasses above and herein, singly or in combination.

In certain embodiments, the invention provides a compound selected from Table 1:

TABLE 1

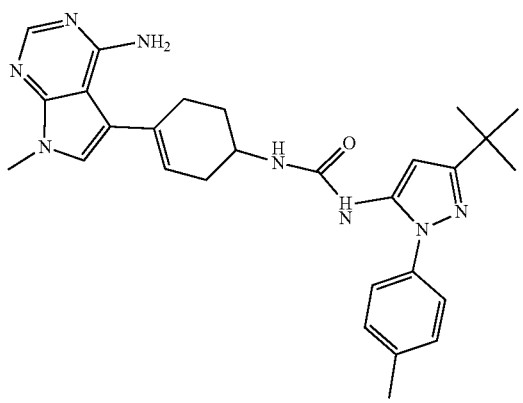 [SMILES: Cc1ccc(-n2nc(C(C)(C)C)cc2NC(=O)NC2CC=C(c3cn(C)c4ncnc(N)c34)CC2)cc1]

1

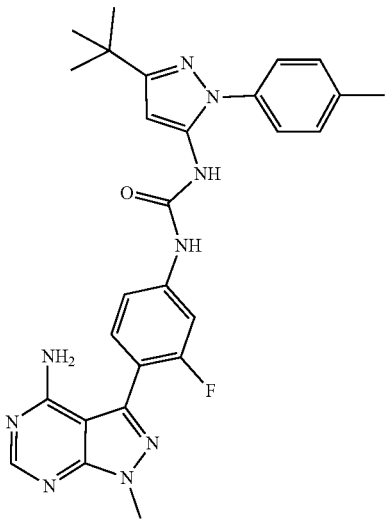 [SMILES: Cc1ccc(-n2nc(C(C)(C)C)cc2NC(=O)Nc2ccc(-c3nn(C)c4ncnc(N)c34)c(F)c2)cc1]

2

TABLE 1-continued
3
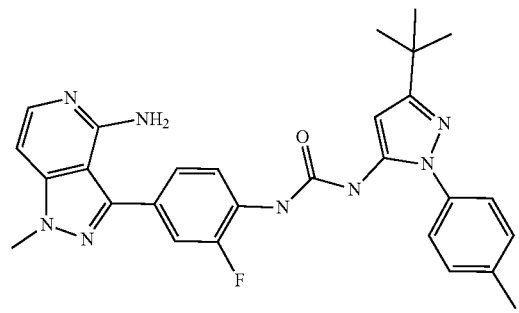
4
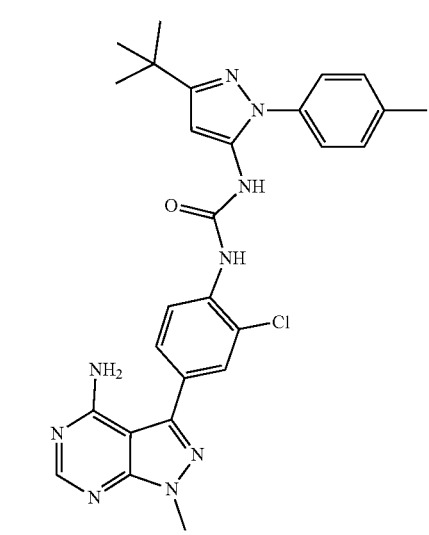 [SMILES: Cc1ccc(-n2nc(C(C)(C)C)cc2NC(=O)Nc2ccc(-c3nn(C)c4ncnc(N)c34)cc2Cl)cc1]
5
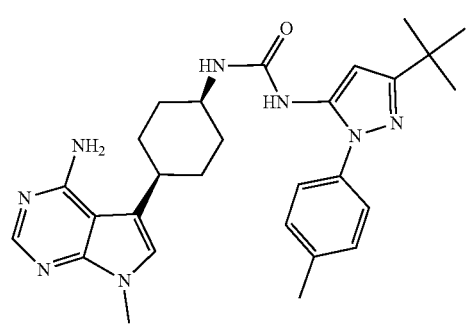 [SMILES: Cc1ccc(-n2nc(C(C)(C)C)cc2NC(=O)N[C@H]2CC[C@@H](c3cn(C)c4ncnc(N)c43)CC2)cc1]
TABLE 1-continued
6
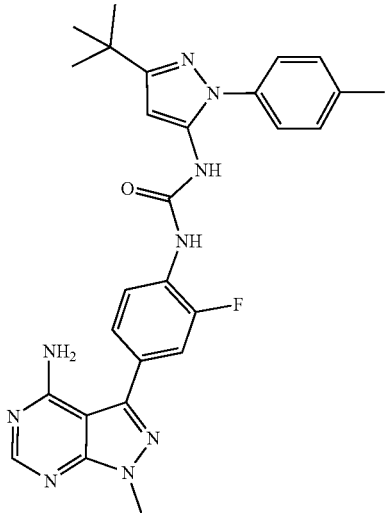 [SMILES: Cc1ccc(-n2nc(C(C)(C)C)cc2NC(=O)Nc2ccc(-c3nn(C)c4ncnc(N)c34)cc2F)cc1]
7
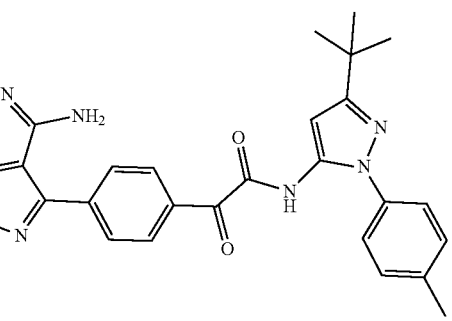
8
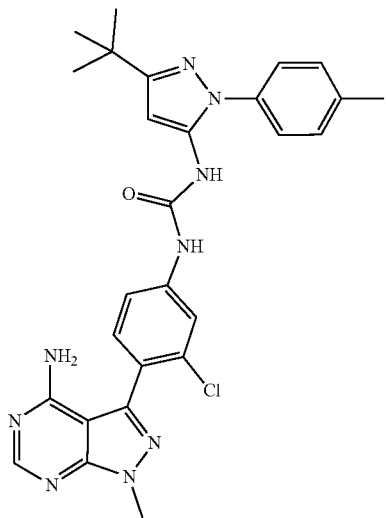 [SMILES: Cc1ccc(-n2nc(C(C)(C)C)cc2NC(=O)Nc2ccc(-c3nn(C)c4ncnc(N)c34)c(Cl)c2)cc1]

TABLE 1-continued
9
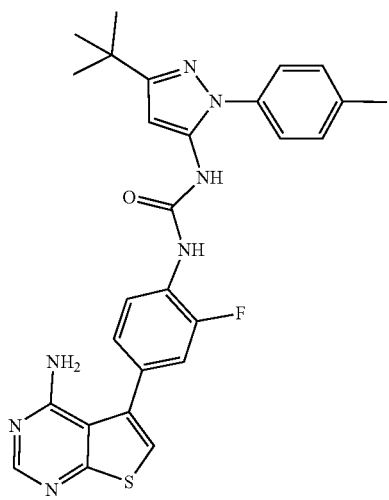 [SMILES: Cc1ccc(-n2nc(C(C)(C)C)cc2NC(=O)Nc2ccc(-c3csc4ncnc(N)c34)cc2F)cc1]
10
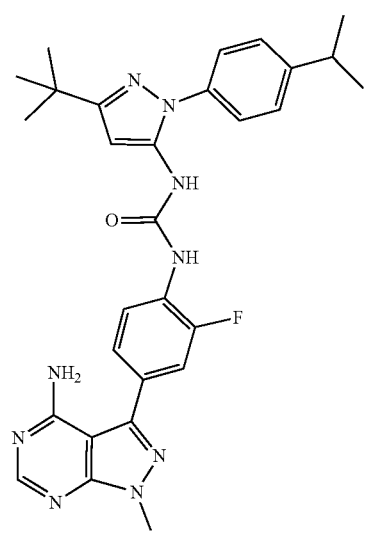 [SMILES: CC(C)c1ccc(-n2nc(C(C)(C)C)cc2NC(=O)Nc2ccc(-c3nn(C)c4ncnc(N)c34)cc2F)cc1]
11
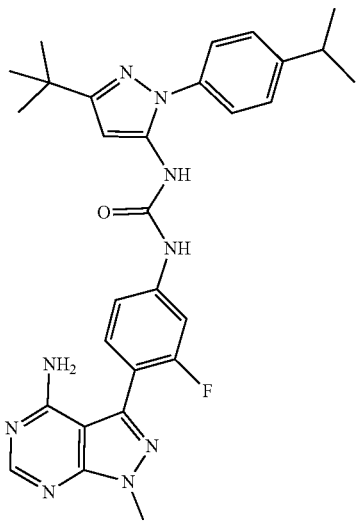 [SMILES: CC(C)c1ccc(-n2nc(C(C)(C)C)cc2NC(=O)Nc2ccc(-c3nn(C)c4ncnc(N)c34)c(F)c2)cc1]
TABLE 1-continued
12
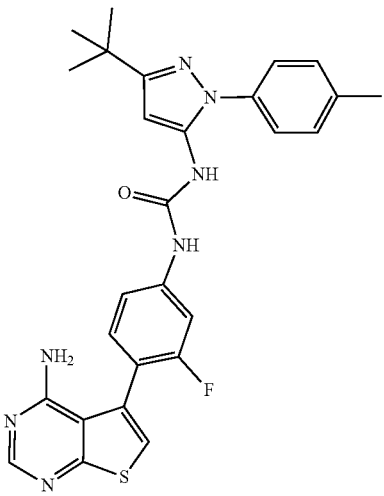 [SMILES: Cc1ccc(-n2nc(C(C)(C)C)cc2NC(=O)Nc2ccc(-c3csc4ncnc(N)c34)c(F)c2)cc1]
13
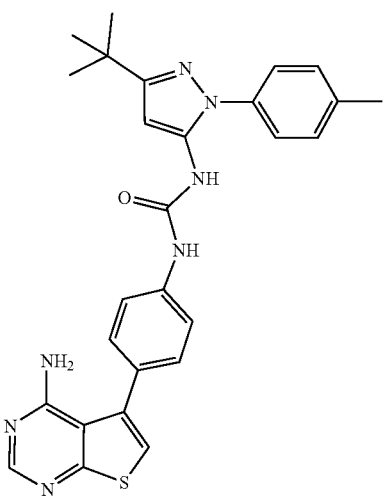 [SMILES: Cc1ccc(-n2nc(C(C)(C)C)cc2NC(=O)Nc2ccc(-c3csc4ncnc(N)c34)cc2)cc1]
14
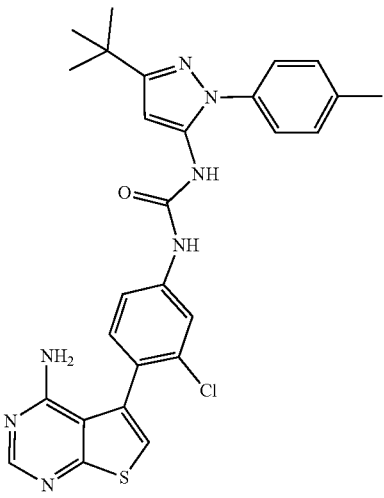 [SMILES: Cc1ccc(-n2nc(C(C)(C)C)cc2NC(=O)Nc2ccc(-c3csc4ncnc(N)c34)c(Cl)c2)cc1]

TABLE 1-continued
15
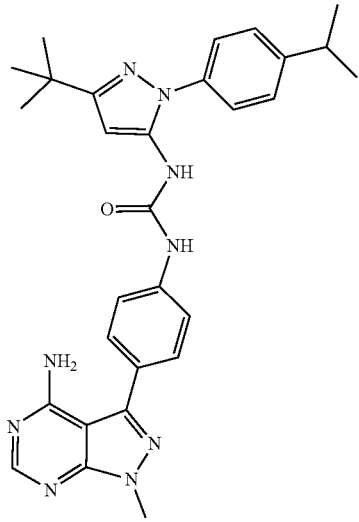 [SMILES: CC(C)c1ccc(-n2nc(C(C)(C)C)cc2NC(=O)Nc2ccc(-c3nn(C)c4ncnc(N)c34)cc2)cc1]
16
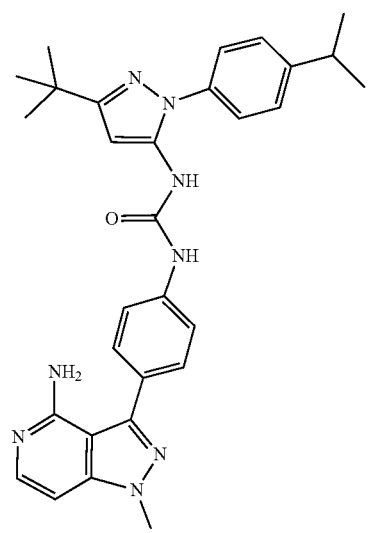 [SMILES: CC(C)c1ccc(-n2nc(C(C)(C)C)cc2NC(=O)Nc2ccc(-c3nn(C)c4ccnc(N)c34)cc2)cc1]
17
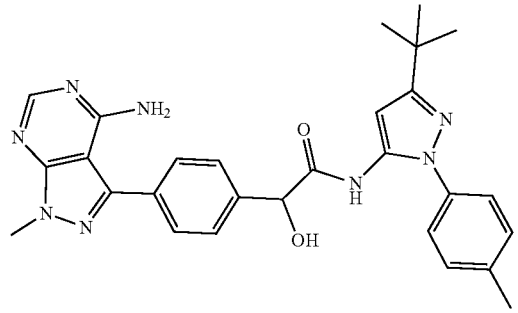 [SMILES: Cc1ccc(-n2nc(C(C)(C)C)cc2NC(=O)C(O)c2ccc(-c3nn(C)c4ncnc(N)c34)cc2)cc1]
TABLE 1-continued
18
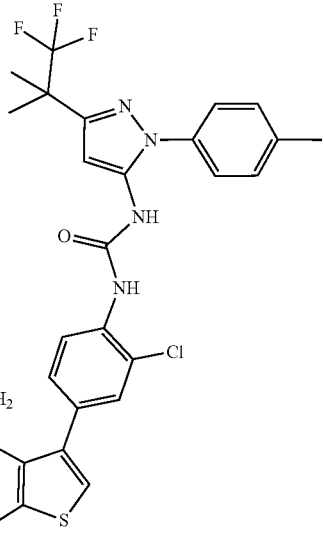
19
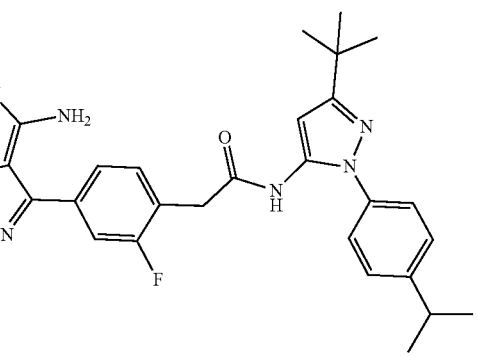
20
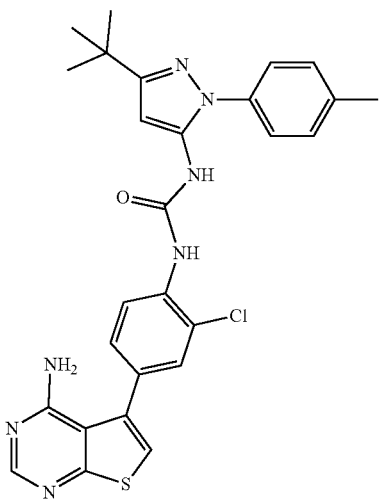 [SMILES: Cc1ccc(-n2nc(C(C)(C)C)cc2NC(=O)Nc2ccc(-c3csc4ncnc(N)c34)cc2Cl)cc1]

TABLE 1-continued
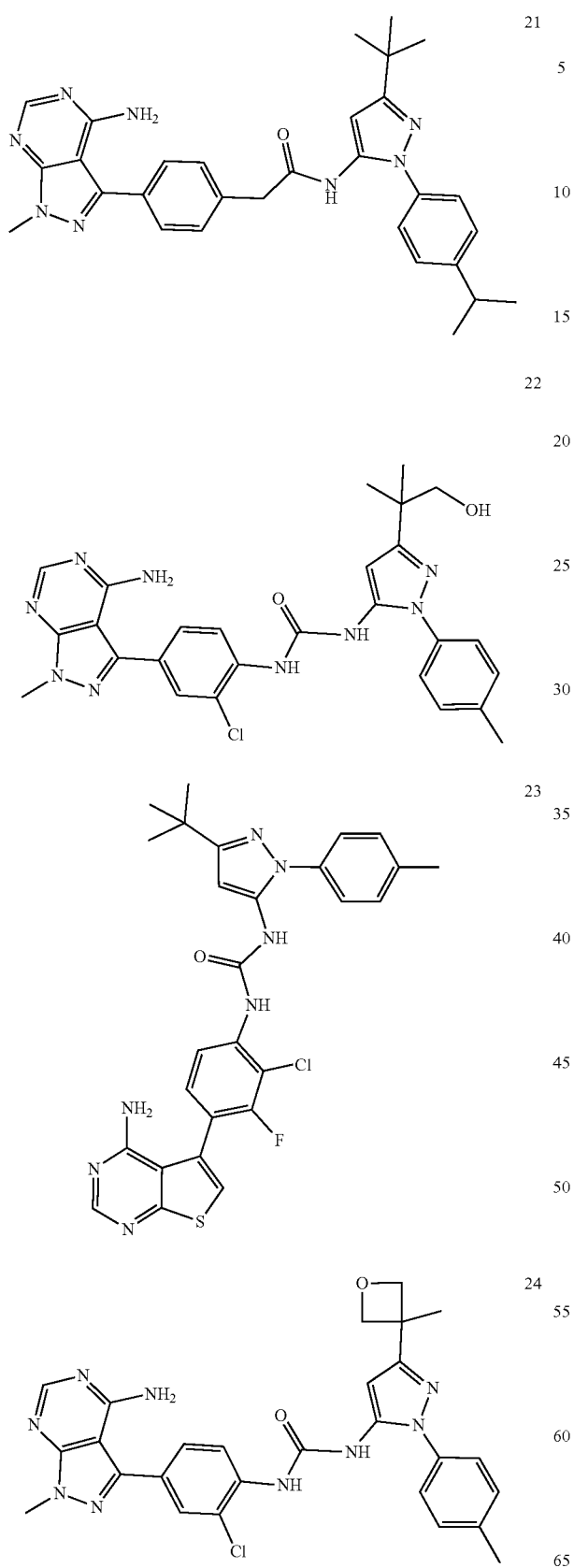
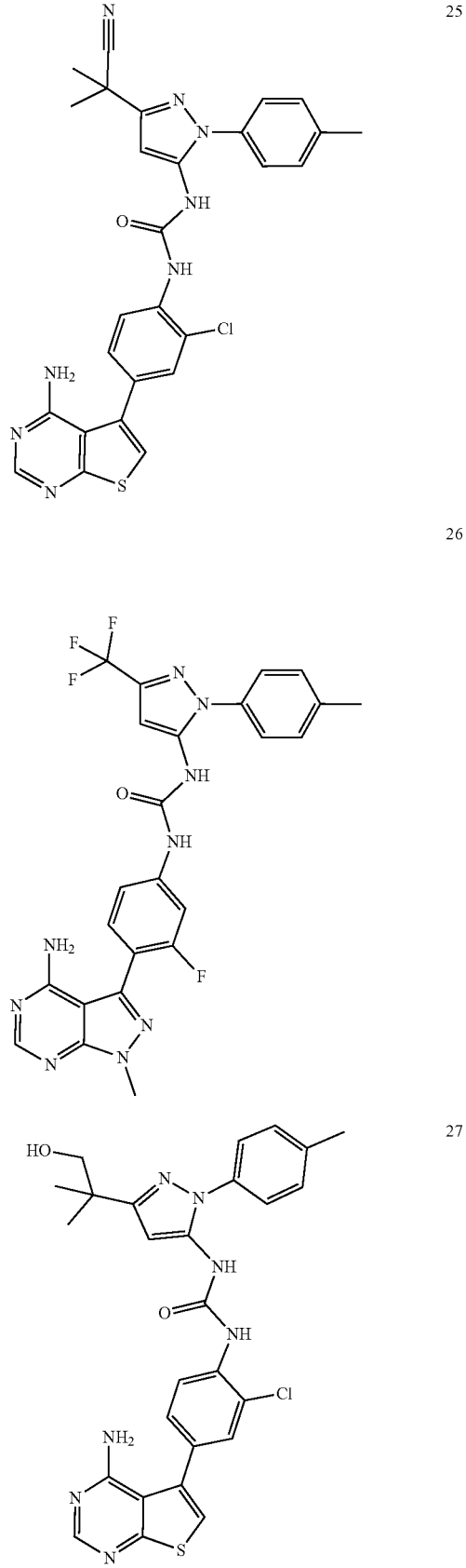

TABLE 1-continued

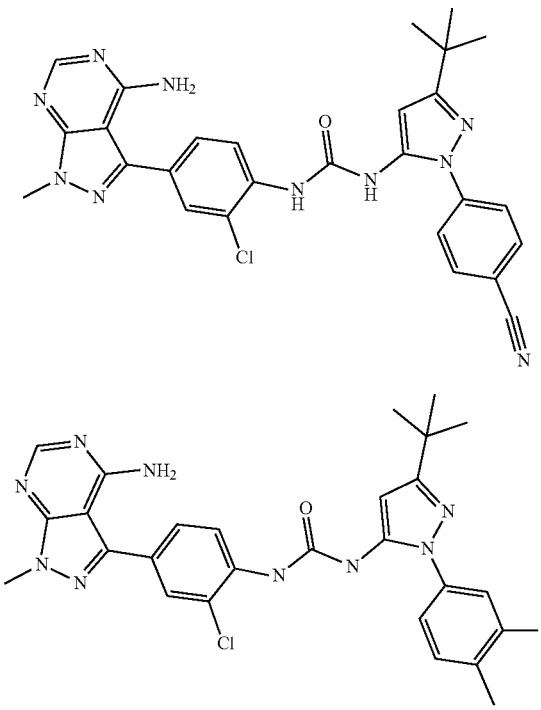

In some embodiments, the present invention provides a compound selected from those depicted above, or a pharmaceutically acceptable salt thereof.

In certain embodiments, the compounds of the invention exhibit increased microsome stability and permeability.

Various structural depictions may show a heteroatom without an attached group, radical, charge, or counterion. Those of ordinary skill in the art are aware that such depictions are meant to indicate that the heteroatom is attached to hydrogen (e.g.,

is understood to be

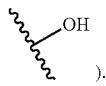

).

In certain embodiments, the compounds of the invention were synthesized in accordance with the schemes provided in the Examples below.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit IRAK, or a mutant thereof, in a biological sample or in a patient. In certain embodiments, the amount of compound in compositions of this invention is such that is effective to measurably inhibit IRAK, or a mutant thereof, in a biological sample or in a patient. In certain embodiments, a composition of this invention is formulated for administration to a patient in need of such composition.

The term "patient" or "subject", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that are used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium tri silicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention are administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention include aqueous or oleaginous suspension. These suspensions are formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that are employed are water, Ringer's solution and isotonic sodium chloride solution. In addition, sterile, fixed oils are conventionally employed as a solvent or suspending medium.

For this purpose, any bland fixed oil employed includes synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms are also be used for the purposes of formulation.

Pharmaceutically acceptable compositions of this invention are orally administered in any orally acceptable dosage form. Exemplary oral dosage forms are capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents are optionally also added.

Alternatively, pharmaceutically acceptable compositions of this invention are administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention are also administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches are also used.

For topical applications, provided pharmaceutically acceptable compositions are formulated in a suitable ointment containing the active component suspended or dissolved in one or more carriers. Exemplary carriers for topical administration of compounds of this are mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Pharmaceutically acceptable compositions of this invention are optionally administered by nasal aerosol or inhalation. Such compositions are prepared according to techniques well-known in the art of pharmaceutical formulation and are prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that are optionally combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

The present invention furthermore relates to a method for treating a subject suffering from an IRAK related disorder, comprising administering to said subject an effective amount of a compound of formula I and related formulae.

The present invention preferably relates to a method, wherein the IRAK associated disorder is an autoimmune disorder or condition associated with an overactive immune response or cancer. The present invention furthermore relates to a method of treating a subject suffering from an immunoregulatory abnormality, comprising administering to said subject a compound of formula (I), and related formulae in an amount that is effective for treating said immunoregulatory abnormality.

The present invention preferably relates to a method wherein the immunoregulatory abnormality is an autoimmune or chronic inflammatory disease selected from the group consisting of: allergic diseases, amyotrophic lateral sclerosis (ALS), systemic lupus erythematosus, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy and asthma.

The present invention furthermore relates to a method wherein the immunoregulatory abnormality is bone marrow or organ transplant rejection or graft-versus-host disease.

The present invention furthermore relates to a method wherein the immunoregulatory abnormality is selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, systemic sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C4 release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, parkison diseases, trauma, and chronic bacterial infection.

In certain embodiments, disorders associated with IRAK are selected from Rheumatoid Arthritis, Psoriatic arthritis, Osteoarthritis, Systemic Lupus Erythematosus, Lupus nephritis, Ankylosing Spondylitis, Osteoporosis, Systemic sclerosis, Multiple Sclerosis, Psoriasis, Type I diabetes, Type II diabetes, Inflammatory Bowel Disease (Cronh's Disease and Ulcerative Colitis), Hyperimmunoglobulinemia D and periodic fever syndrome, Cryopyrin-associated periodic syndromes, Schnitzler's syndrome, Systemic juvenile idiopathic arthritis, Adult's onset Still's disease, Gout, Pseudogout, SAPHO syndrome, Castleman's disease, Sepsis, Stroke, Atherosclerosis, Celiac disease, DIRA (Deficiency of IL-1 Receptor Antagonist), Alzheimer's disease, Parkinson's disease, and Cancer.

In certain embodiments, the cancer is selected from carcinoma, lymphoma, blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, and leukemia or lymphoid malignancies. More particular examples of such cancers include squamous cell cancer (e.g., epithelial squamous cell cancer), lung cancer including small-cell lung cancer (SCLC), non-small cell lung cancer (NSCLC), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer (including metastatic breast cancer), colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophageal cancer, tumors of the biliary tract, as well as head and neck cancer.

In certain embodiments, the cancer is brain, lung, colon, epidermoid, squamous cell, bladder, gastric, pancreatic, breast, head, neck, renal, kidney, liver, ovarian, prostate, colorectal, uterine, rectal, oesophageal, testicular, gynecological, thyroid cancer, melanoma, hematologic malignancies such as acute myelogenous leukemia, multiple myeloma, chronic myelogneous leukemia, myeloid cell leukemia, glioma, Kaposi's sarcoma, or any other type of solid or liquid tumors. In some embodiments, the cancer is metastatic cancer. In some embodiments, the cancer is colorectal cancer. In some embodiments, the cancer is colon cancer.

In various embodiments, compounds of formula (I), and related formulae exhibit a IC50 for the binding to IRAK of less than about 5 µM, preferably less than about 1 µM and even more preferably less than about 0.100 µM.

The method of the invention can be performed either in-vitro or in-vivo. The susceptibility of a particular cell to treatment with the compounds according to the invention can be particularly determined by in-vitro tests, whether in the course of research or clinical application. Typically, a culture of the cell is combined with a compound according to the invention at various concentrations for a period of time which is sufficient to allow the active agents to inhibit IRAK activity, usually between about one hour and one week. In-vitro treatment can be carried out using cultivated cells from a biopsy sample or cell line.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

For identification of a signal transduction pathway and for detection of interactions between various signal transduction pathways, various scientists have developed suitable models or model systems, for example cell culture models and models of transgenic animals. For the determination of certain stages in the signal transduction cascade, interacting compounds can be utilized in order to modulate the signal. The compounds according to the invention can also be used as reagents for testing IRAK-dependent signal transduction pathways in animals and/or cell culture models or in the clinical diseases mentioned in this application.

Moreover, the subsequent teaching of the present specification concerning the use of the compounds according to formula (I) and its derivatives for the production of a medicament for the prophylactic or therapeutic treatment and/or monitoring is considered as valid and applicable without restrictions to the use of the compound for the inhibition of IRAK activity if expedient.

The invention also relates to the use of compounds according to formula (I) and/or physiologically acceptable salts thereof for the prophylactic or therapeutic treatment and/or monitoring of diseases that are caused, mediated and/or propagated by IRAK activity. Furthermore, the invention relates to the use of compounds according to formula (I) and/or physiologically acceptable salts thereof for the production of a medicament for the prophylactic or therapeutic treatment and/or monitoring of diseases that are caused, mediated and/or propagated by IRAK activity. In certain embodiments, the invention provides the use of a compound according to formula I or physiologically acceptable salts thereof, for the production of a medicament for the prophylactic or therapeutic treatment of an IRAK-mediated disorder.

Compounds of formula (I) and/or a physiologically acceptable salt thereof can furthermore be employed as intermediate for the preparation of further medicament active ingredients. The medicament is preferably prepared in a non-chemical manner, e.g. by combining the active ingredient with at least one solid, fluid and/or semi-fluid carrier or excipient, and optionally in conjunction with a single or more other active substances in an appropriate dosage form.

The compounds of formula (I) according to the invention can be administered before or following an onset of disease once or several times acting as therapy. The aforementioned compounds and medical products of the inventive use are particularly used for the therapeutic treatment. A therapeutically relevant effect relieves to some extent one or more symptoms of a disorder, or returns to normality, either partially or completely, one or more physiological or biochemical parameters associated with or causative of a disease or pathological condition. Monitoring is considered as a kind of treatment provided that the compounds are administered in distinct intervals, e.g. in order to boost the response and eradicate the pathogens and/or symptoms of the disease completely. Either the identical compound or different compounds can be applied. The methods of the invention can also be used to reduce the likelihood of developing a disorder or even prevent the initiation of disorders associated with IRAK activity in advance or to treat the arising and continuing symptoms.

In the meaning of the invention, prophylactic treatment is advisable if the subject possesses any preconditions for the aforementioned physiological or pathological conditions, such as a familial disposition, a genetic defect, or a previously incurred disease.

The invention furthermore relates to a medicament comprising at least one compound according to the invention and/or pharmaceutically usable derivatives, salts, solvates and stereoisomers thereof, including mixtures thereof in all ratios. In certain embodiments, the invention relates to a medicament comprising at least one compound according to the invention and/or physiologically acceptable salts thereof.

A "medicament" in the meaning of the invention is any agent in the field of medicine, which comprises one or more compounds of formula (I) or preparations thereof (e.g. a pharmaceutical composition or pharmaceutical formulation) and can be used in prophylaxis, therapy, follow-up or aftercare of patients who suffer from diseases, which are associated with IRAK activity, in such a way that a pathogenic modification of their overall condition or of the condition of particular regions of the organism could establish at least temporarily.

In various embodiments, the active ingredient may be administered alone or in combination with other treatments. A synergistic effect may be achieved by using more than one compound in the pharmaceutical composition, i.e. the compound of formula (I) is combined with at least another agent as active ingredient, which is either another compound of formula (I) or a compound of different structural scaffold. The active ingredients can be used either simultaneously or sequentially.

Included herein are methods of treatment in which at least one chemical entity provided herein is administered in combination with an anti-inflammatory agent. Anti-inflammatory agents include but are not limited to NSAIDs, non-specific and COX-2 specific cyclooxygenase enzyme inhibitors, gold compounds, corticosteroids, methotrexate, tumor necrosis factor (TNF) antagonists, immunosuppressants and methotrexate.

Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib dnd/or etoricoxib.

In some embodiments, the anti-inflammatory agent is a salicylate. Salicylates include by are not limited to acetyl-salicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory compound is an anti-monoclonal antibody (such as eculizumab or pexelizumab), a TNF antagonist, such as entanercept, or infliximab, which is an anti-TNF alpha monoclonal antibody.

Still other embodiments of the invention pertain to combinations in which at least one active agent is an immunosuppressant compound such as an immunosuppressant compound chosen from methotrexate, leflunomide, cyclosporine, tacrolimus, azathioprine, and mycophenolate mofetil.

The disclosed compounds of the formula I can be administered in combination with other known therapeutic agents, including anticancer agents. As used here, the term "anti-cancer agent" relates to any agent which is administered to a patient with cancer for the purposes of treating the cancer.

The anti-cancer treatment defined above may be applied as a monotherapy or may involve, in addition to the herein disclosed compounds of formula I, conventional surgery or radiotherapy or medicinal therapy. Such medicinal therapy, e.g. a chemotherapy or a targeted therapy, may include one or more, but preferably one, of the following anti-tumor agents:

Alkylating agents: such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechloretamine, carboquone; apaziquone, fotemustine, glufosfamide, palifosfamide, pipobroman, trofosfamide, uramustine, TH-302[4], VAL-083[4];

Platinum Compounds: such as carboplatin, cisplatin, eptaplatin, miriplatine hydrate, oxaliplatin, lobaplatin, nedaplatin, picoplatin, satraplatin; lobaplatin, nedaplatin, picoplatin, satraplatin;

DNA altering agents: such as amrubicin, bisantrene, decitabine, mitoxantrone, procarbazine, trabectedin, clofarabine; amsacrine, brostallicin, pixantrone, laromustine[1,3];

Topoisomerase Inhibitors: such as etoposide, irinotecan, razoxane, sobuzoxane, teniposide, topotecan; amonafide, belotecan, elliptinium acetate, voreloxin;

Microtubule modifiers: such as cabazitaxel, docetaxel, eribulin, ixabepilone, paclitaxel, vinblastine, vincristine, vinorelbine, vindesine, vinflunine; fosbretabulin, tesetaxel;

Antimetabolites: such as asparaginase[3], azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur; doxifluridine, elacytarabine, raltitrexed, sapacitabine, tegafur[2,3], trimetrexate;

Anticancer antibiotics: such as bleomycin, dactinomycin, doxorubicin, epirubicin, idarubicin, levamisole, miltefosine, mitomycin C, romidepsin, streptozocin, valrubicin, zinostatin, zorubicin, daunurobicin, plicamycin; aclarubicin, peplomycin, pirarubicin;

Hormones/Antagonists: such as abarelix, abiraterone, bicalutamide, buserelin, calusterone, chlorotrianisene, degarelix, dexamethasone, estradiol, fluocortolone fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol; acolbifene, danazol, deslorelin, epitiostanol, orteronel, enzalutamide[1,3];

Aromatase inhibitors: such as aminoglutethimide, anastrozole, exemestane, fadrozole, letrozole, testolactone; formestane;

Small molecule kinase inhibitors: such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib; afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifarnib, tivantinib, tivozanib, trametinib, pimasertib, brivanib alaninate, cediranib, apatinib[4], cabozantinib S-malate[1,3], ibrutinib[1,3], icotinib[4], buparlisib[2], cipatinib[4], cobimetinib[1,3], idelalisib[1,3], fedratinib[1], XL-647[4];

Photosensitizers: such as methoxsalen[3]; porfimer sodium, talaporfin, temoporfin;

Antibodies: such as alemtuzumab, besilesomab, brentuximab vedotin, cetuximab, denosumab, ipilimumab, ofatumumab, panitumumab, rituximab, tositumomab, trastuzumab, bevacizumab, pertuzumab[2,3]; catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab[1,2,3], onartuzumab[1,3], racotumomab[1], tabalumab[1,3], EMD-525797[4], nivolumab[1,3];

Cytokines: such as aldesleukin, interferon alfa[2], interferon alfa2a[3], interferon alfa2b[2,3]; celmoleukin, tasonermin, teceleukin, oprelvekin[1,3], recombinant interferon beta-1a[4];

Drug Conjugates: such as denileukin diftitox, ibritumomab tiuxetan, iobenguane 1123, prednimustine, trastuzumab emtansine, estramustine, gemtuzumab, ozogamicin, aflibercept; cintredekin besudotox, edotreotide, inotuzumab ozogamicin, naptumomab estafenatox, oportuzumab monatox, technetium (99mTc) arcitumomab[1,3], vintafolide[1,3];

Vaccines: such as sipuleucel[3]; vitespen[3], emepepimut-S[3], oncoVAX[4], rindopepimut[3], troVax[4], MGN-1601[4], MGN-1703[4]; and Miscellaneous: alitretinoin, bexarotene, bortezomib, everolimus, ibandronic acid, imiquimod, lenalidomide, lentinan, metirosine, mifamurtide, pamidronic acid, pegaspargase, pentostatin, sipuleucel[3], sizofiran, tamibarotene, temsirolimus, thalidomide, tretinoin, vismodegib, zoledronic acid, vorinostat; celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine[4], picibanil[4], reolysin[4], retaspimycin hydrochloride[1,3], trebananib[2,3], virulizin[4], carfilzomib[1,3], endostatin[4], immucothel[4], belinostat[3], MGN-1703[4].

[1] Prop. INN (Proposed International Nonproprietary Name);
[2] Rec. INN (Recommended International Nonproprietary Names);
[3] USAN (United States Adopted Name);
[4] no INN.

In another aspect, the invention provides for a kit consisting of separate packs of an effective amount of a compound according to the invention and/or pharmaceutically acceptable salts, derivatives, solvates and stereoisomers thereof, including mixtures thereof in all ratios, and optionally, an effective amount of a further active ingredient. The kit comprises suitable containers, such as boxes, individual bottles, bags or ampoules. The kit may, for example, comprise separate ampoules, each containing an effective amount of a compound according to the invention and/or pharmaceutically acceptable salts, derivatives, solvates and stereoisomers thereof, including mixtures thereof in all ratios, and an effective amount of a further active ingredient in dissolved or lyophilized form.

Thus, especially preferred is:
(1) A compound of formula I,

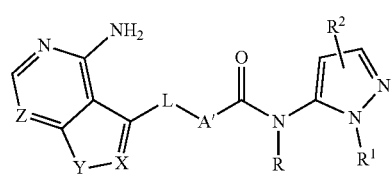

or a pharmaceutically acceptable salt thereof, wherein:
A' is C=O, C(R)$_2$ or NR;
L is a divalent group selected from C$_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;

X is CR or N;

Y is NR or S;

Z is CR or N;

$R^1$ is $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;

$R^2$ is —R, halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;

each R is independently hydrogen, $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or two R groups on the same atom are taken together with the atom to which they are attached to form a $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

(2) A compound as described herein, preferably as described above and/or below and more preferably as described in Section (1), wherein A' is C=O, =CH$_2$, CHOH, or NH.

(3) A compound as described herein, preferably as described above and/or below and more preferably as described in Section (1) and/or Section (2), wherein L is a divalent group selected from phenyl, cyclopentyl, cyclohexyl, cyclohexenyl, cycloheptyl, furanyl, furazanyl, imidazolidinyl, imidazolinyl, imidazolyl, 1H-indazolyl, indolenyl, isoxazolyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, piperazinyl, piperidinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, 2H-pyrrolyl, pyrrolyl, tetrahydrofuranyl, thiazolyl, thienyl, thiophenyl, oxetanyl, and azetidinyl, each of which is optionally substituted.

(4) A compound as described herein, preferably as described above and/or below and more preferably as described in one or more of Sections (1) to (3), wherein L is a divalent group selected from

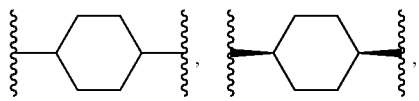

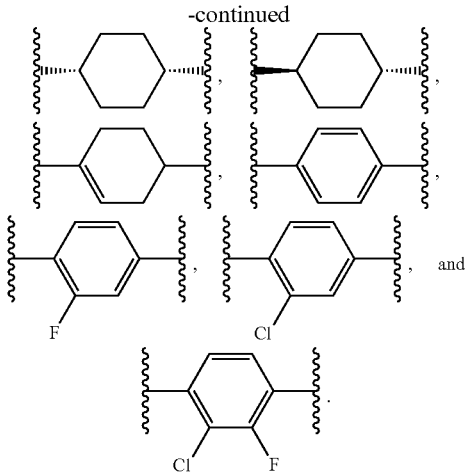

(5) A compound as described herein, preferably as described above and/or below and more preferably as described in one or more of Sections (1) to (4), wherein $R^1$ is $C_{3-10}$ aryl.

(6) A compound as described herein, preferably as described above and/or below and more preferably as described in one or more of Sections (1) to (5), wherein $R^1$ is

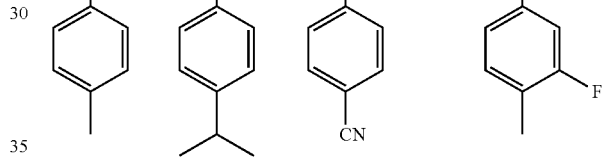

(7) A compound as described herein, preferably as described above and/or below and more preferably as described in one or more of Sections (1) to (6), wherein $R^2$ is $C_{1-6}$ aliphatic or 3-7 membered heterocylic ring having 1-4 heteroatoms independently selected from nitrogen, oxygen, or sulfur.

(8) A compound as described herein, preferably as described above and/or below and more preferably as described in one or more of Sections (1) to (7), wherein $R^2$ is methyl, ethyl, propyl, i-propyl, n-butyl, i-butyl, t-butyl, straight chain or branched pentyl, or straight chain or branched hexyl, or $R^2$ is a 4 membered heterocylic ring having 1-4 heteroatoms independently selected from nitrogen, oxygen, or sulfur.

(9) A compound as described herein, preferably as described above and/or below and more preferably as described in one or more of Sections (1) to (8), wherein $R^2$ is —CF$_3$,

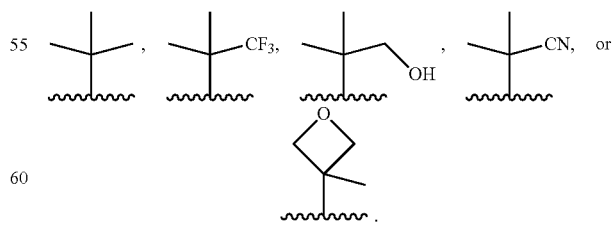

(10) A compound as described herein, preferably as described above and/or below, more preferably as described in one or more of Sections (1) to (10) and especially as described in Section (1), of formula I-a,

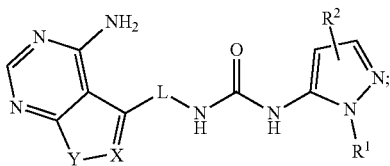

I-a or a pharmaceutically acceptable salt thereof.

(11) A compound as described herein, preferably as described above and/or below, more preferably as described in one or more of Sections (1) to (10) and especially as described in Section (1), of formula I-c,

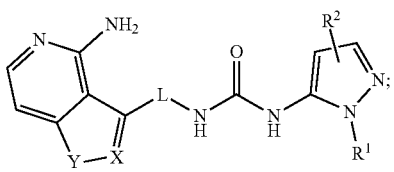

I-c or a pharmaceutically acceptable salt thereof.

(12) A compound as described herein, preferably as described above and/or below, more preferably as described in one or more of Sections (1) to (10) and especially as described in Section (1), of formula I-e,

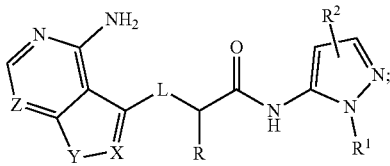

I-e or a pharmaceutically acceptable salt thereof.

(13) A compound as described herein, preferably as described above and/or below, more preferably as described in one or more of Sections (1) to (10) and especially as described in Section (1), of formula I-h,

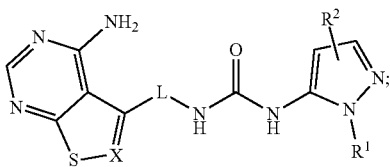

I-h or a pharmaceutically acceptable salt thereof.

(14) A compound as described herein, preferably as described above and/or below, more preferably as described in one or more of Sections (1) to (10) and especially as described in Section (1), selected from Table 1.

(15) A pharmaceutical composition comprising a compound as described herein, preferably as described above and/or below, more preferably as described in one or more of Sections (1) to (14) and especially as described in Section (1), and a pharmaceutically acceptable adjuvant, carrier, or vehicle.

(16) A method for inhibiting IRAK, or a mutant thereof, activity in a patient or in a biological sample, comprising the step of administering to said patient or contacting said biological sample with a compound as described herein, preferably as described above and/or below, more preferably as described in one or more of Sections (1) to (14) and especially as described in Section (1), or a physiologically acceptable salt thereof.

(17) A method for treating an IRAK-mediated disorder in a patient in need thereof, comprising the step of administering to said patient a compound as described herein, preferably as described above and/or below, more preferably as described in one or more of Sections (1) to (14) and especially as described in Section (1).

(18) A method as described herein, preferably as described above and/or below, more preferably as described in Section (16) and/or Section (17) and especially as described in Section (17), wherein the disorder is selected from Rheumatoid Arthritis, Psoriatic arthritis, Osteoarthritis, Systemic Lupus Erythematosus, Lupus nephritis, Ankylosing Spondylitis, Osteoporosis, Systemic sclerosis, Multiple Sclerosis, Psoriasis, Type I diabetes, Type II diabetes, Inflammatory Bowel Disease (Cronh's Disease and Ulcerative Colitis), Hyperimmunoglobulinemia D and periodic fever syndrome, Cryopyrin-associated periodic syndromes, Schnitzler's syndrome, Systemic juvenile idiopathic arthritis, Adult's onset Still's disease, Gout, Pseudogout, SAPHO syndrome, Castleman's disease, andometriosis; Sepsis, Stroke, Atherosclerosis, Celiac disease, DIRA (Deficiency of IL-1 Receptor Antagonist), Alzheimer's disease, Parkinson's disease, and Cancer.

(19) A method for treating a subject as described herein, preferably as described above and/or below and more preferably a method for treating cancer in a subject, said method comprising the step of administering to said subject a compound as described herein, preferably as described above and/or below, more preferably as described in one or more of Sections (1) to (14) and especially as described in Section (1), or a physiologically acceptable salt thereof.

(20) A method as described herein, preferably as described above and/or below, more preferably as described in Section (16), Section (17), Section (18) and/or Section (19) and especially as described in Section (18), wherein the disorder is selected from Rheumatoid Arthritis, Systemic Lupus Erythematosus, Lupus nephritis, and Multiple Sclerosis.

As used herein, the terms "treatment," "treat," and "treating" refer to reversing, alleviating, delaying the onset of, or inhibiting the progress of a disease or disorder, or one or more symptoms thereof, as described herein. In some embodiments, treatment is administered after one or more symptoms have developed. In other embodiments, treatment is administered in the absence of symptoms. For example, treatment is administered to a susceptible individual prior to the onset of symptoms (e.g., in light of a history of symptoms and/or in light of genetic or other susceptibility factors). Treatment is also continued after symptoms have resolved, for example to prevent or delay their recurrence.

The compounds and compositions, according to the method of the present invention, are administered using any amount and any route of administration effective for treating or lessening the severity of a disorder provided above. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention are administered orally or parenterally at dosage levels of about 0.01 mg/kg to about 100 mg/kg and preferably from about 1 mg/kg to about 50 mg/kg, of subject body weight per day, one or more times a day, to obtain the desired therapeutic effect.

In certain embodiments, a therapeutically effective amount of a compound of the formula (I), and related formulae and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

In certain embodiments, the pharmaceutical formulations can be administered in the form of dosage units, which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process, which is generally known in the pharmaceutical art.

Liquid dosage forms for oral administration include, but are not limited to, pharmaceutically acceptable emulsions, microemulsions, solutions, suspensions, syrups and elixirs. In addition to the active compounds, the liquid dosage forms optionally contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions are formulated according to the known art using suitable dispersing or wetting agents and suspending agents. The sterile injectable preparation are also a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This is accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form also optionally comprises buffering agents.

Solid compositions of a similar type are also employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type are also employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms also comprise, as is normal practice, additional substances other than inert diluents, e.g., tableting lubricants and other tableting aids such a magnesium stearate and microcrystalline cellulose. In the case of capsules, tablets and pills, the dosage forms optionally also comprise buffering agents. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting IRAK activity in a biological sample comprising the step of contacting said biological sample with a compound of this invention, or a composition comprising said compound.

According to another embodiment, the invention relates to a method of inhibiting IRAK, or a mutant thereof, activity in a biological sample in a positive manner, comprising the step of contacting said biological sample with a compound of this invention, or a composition comprising said compound.

The compounds of the invention are useful in-vitro as unique tools for understanding the biological role of IRAK, including the evaluation of the many factors thought to influence, and be influenced by, the production of IRAK and the interaction of IRAK. The present compounds are also useful in the development of other compounds that interact with IRAK since the present compounds provide important structure-activity relationship (SAR) information that facilitate that development. Compounds of the present invention that bind to IRAK can be used as reagents for detecting IRAK in living cells, fixed cells, in biological fluids, in tissue homogenates, in purified, natural biological materials, etc. For example, by labeling such compounds, one can identify cells expressing IRAK. In addition, based on their ability to bind IRAK, compounds of the present invention can be used in in-situ staining, FACS (fluorescence-activated cell sorting), sodium dodecyl sulfate polyacrylamide gel electrophoresis (SDS-PAGE), ELISA (enzyme-linked immunoadsorptive assay), etc., enzyme purification, or in purifying cells expressing IRAK inside permeabilized cells. The compounds of the invention can also be utilized as commercial research reagents for various medical research and diagnostic uses. Such uses can include but are not limited to: use as a calibration standard for quantifying the activities of candidate IRAK inhibitors in a variety of functional assays; use as blocking reagents in random compound screening, i.e. in looking for new families of IRAK ligands, the compounds can be used to block recovery of the presently claimed IRAK compounds; use in the co-crystallization with IRAK enzyme, i.e. the compounds of the present invention will allow formation of crystals of the compound bound to IRAK, enabling the determination of enzyme/compound structure by x-ray crystallography; other research and diagnostic applications, wherein IRAK is preferably activated or such activation is conveniently calibrated against a known quantity of an IRAK inhibitor, etc.; use in assays as probes for determining the expression of IRAK in cells; and developing assays for detecting compounds which bind to the same site as the IRAK binding ligands.

The compounds of the invention can be applied either themselves and/or in combination with physical measurements for diagnostics of treatment effectiveness. Pharmaceutical compositions containing said compounds and the use of said compounds to treat IRAK-mediated conditions is a promising, novel approach for a broad spectrum of therapies causing a direct and immediate improvement in the state of health, whether in human or in animal. The orally bioavailable and active new chemical entities of the invention improve convenience for patients and compliance for physicians.

The compounds of formula (I), their salts, isomers, tautomers, enantiomeric forms, diastereomers, racemates, derivatives, prodrugs and/or metabolites are characterized by a high specificity and stability, low manufacturing costs and convenient handling. These features form the basis for a reproducible action, wherein the lack of cross-reactivity is included, and for a reliable and safe interaction with the target structure.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of IRAK, or a mutant thereof, activity in a biological sample is useful for a variety of purposes that are known to one of skill in the art. Examples of such purposes include, but are not limited to, blood transfusion, organ transplantation, biological specimen storage, and biological assays.

The term "about" as used herein with respect to numbers, figures, ranges and/or amounts is preferably meant to mean "circa" and/or "approximately". The meaning of those terms is well known in the art and preferably includes a variance, deviation and/or variability of the respective number, figure, range and/or amount of plus/minus 15% and especially of plus/minus 10%.

In any case, the term "about" as used herein with respect to numbers, figures, ranges and/or amounts is preferably meant to mean "circa" and/or "approximately". The meaning of those terms is well known in the art and preferably includes a variance, deviation and/or variability of the respective number, figure, range and/or amount of at least plus/minus 5% or of plus/minus 5%.

The terms "disorder(s)" and "disease(s)" as used herein are well-known and understood in the art. In the context of the present invention they are preferably used as synonyms and thus are preferably interchangeable, if the context they are used herein does not strongly implicate otherwise.

In the medical context, including, but not limited to treatment regimens, dosing schedules and clinical trial designs, for convenience and/or ease of use by patients, medical staff and/or physicians, as well as reliability and/or reproducibility of results etc., the terms "week"/"a week", "month"/"a month" and/or "year"/"a year" can used with slight deviations from the definitions of the Gregorian calendar. For example, in said medical context, a month is often referred to as 28 days, and a year is often referred to 48 weeks.

Thus, in the context of the instant invention, the term "week" or "a week" preferably refers to a period of time of about 5, about 6 or about 7 days, more preferably about 7 days.

In the medical context, the term "month" or "a month" preferably refers to a period of time of about 28, about 29, about 30 or about 31 days, more preferably about 28, about 30 or about 31 days.

In the medical context, the term "year" or "a year" preferably refers to a period of time of about 12 months or to a period of time of about 48, about 50, or about 52 weeks, more preferably 12 months, or about 48 or about 52 weeks.

Especially preferred according to the invention is subject matter as described herein, wherein the characteristics of two or more preferred, more preferred and/or especially preferred embodiments, aspects and/or subjects are combined into one embodiment, aspect and/or subject. Preferably, according to this invention, preferred subjects or embodiments can be combined with other preferred subjects or embodiments; more preferred subjects or embodiments can be combined with other less preferred or even more preferred subjects or embodiments; especially preferred subjects or embodiments can be combined with other just preferred or just even more preferred subjects or embodiments, and the like.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

The symbols and conventions used in the following descriptions of processes, schemes, and examples are consistent with those used in the contemporary scientific literature, for example, the Journal of the American Chemical Society or the Journal of Biological Chemistry.

All NMR experiments were recorded on Bruker Avance III 400 NMR Spectrometer equipped with a Bruker PABBO BB-1H/D Z GRD probe at 400 MHz for proton NMR or a Bruker DPX-300 MHz. Most deuterated solvents contained typically 0.03% to 0.05% v/v tetramethylsilane, which was used as the reference signal (set at δ 0.00 for both $^1$H and $^{13}$C). In cases where the deuterated solvents did not contain tetramethylsilane, the residual non-deuterated solvent peaks were used as a reference signal, as per published guidelines (J. Org. Chem., Vol. 62, No. 21, 1997). Chemical shifts are expressed in parts per million (ppm, δ units). Coupling constants are in units of hertz (Hz). Splitting patterns describe apparent multiplicities and are designated as s (singlet), d (doublet), t (triplet), q (quartet), m (multiplet), qt (quintuplet) or brs (broad singlet).

The following abbreviations refer to the abbreviations used below:
Ac (acetyl); ACN (acetonitrile); atm (atmosphere); DIEA (Di-isopropyl ethylamine); ° C. (degrees centigrade); DMF (dimethylformamide); DMSO (dimethylsulfoxide); dppf (1,1'-bis-diphenyl phosphine ferrocene); eq (equivalent); EtOAc (Ethylacetate); g (gram); HATU (N-[(Dimethylamino)(3H-[1,2,3]triazolo[4,5-b]pyridin-3-yloxy)methylene]-N-methylmethanaminiumhexafluoro phosphate); HPLC (High Performance Liquid Chromatography); h (hour); LC (liquid Chromatography); LDA (lithium diisopropylamine); MeOH (methanol); min (minute); mL (milliliter); mmol (millimole); MS (Mass spectroscopy); NMR (Nuclear Magnetic Resonance); 0/N (overnight); PE (Petroleum Ether); RT (room temperature); TBDMS (tert-Butyldimethylsilyl); TEA (triethylamine); TFA (trifluoroacetic acid); THF (tetrahydofurane); TMS (trimethylsilyl).

UPLC/MS analyses were performed on a Waters AquityH with SQ detector (ESI) and LC/MS on an Agilent 1200 Series with a quadupole detector or a SHIMADZU LC-MS machine consisting of an UFLC 20-AD system and a LCMS 2020 MS detector.

Purity was measured using a Waters aquityH equipped with a XBridge column C8, 3.5 µm, 4.6×50 mm, using water/ACN with 0.1% TFA as eluent, gradient from 0 to 100% in 8 min (reported as 'UPLC'), unless otherwise indicated.

The microwave reactions were conducted using Biotage Initiator Microwave Synthesizer using standard protocols that are known in the art.

The compounds of the invention were prepared from readily available starting materials by several synthetic approaches, using both solution-phase and solid-phase chemistry protocols or mixed solution and solid phase protocols. Examples of synthetic pathways are described below in the examples. Unless otherwise stated, compounds of the invention obtained as a racemic mixture can be separated to provide an enantiomerically enriched mixture or a pure enantiomer.

The commercially available starting materials used in the following experimental description were purchased from Sigma-Aldrich or Fisher unless otherwise reported.

Intermediate 1: 3-(4-aminophenyl)-1-methyl-1H-pyrazolo[3,4-d]pyrimidin-4-amine

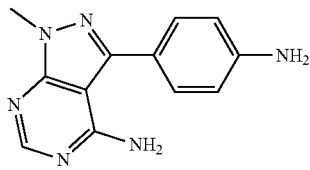 [SMILES: Cn1nc(-c2ccc(N)cc2)c2c(N)ncnc21]

A mixture of 4-(tetramethyl-1,3,2-dioxaborolan-2-yl)aniline (300 mg, 1.37 mmol, 1.0 eq), 3-bromo-1-methyl-1H-pyrazolo[3,4-d]pyrimidin-4-amine (310 mg, 1.36 mmol, 1.0 eq), Pd(dppf)Cl$_2$ (100 mg, 0.14 mmol, 0.10 eq) in Dioxane (12 mL) and a solution of sodium bicarbonate (110 mg, 1.31 mmol, 1.0 eq) in water (4 mL) was purged with nitrogen in a sealed tube before being heated at 100° C. for 2 h. The resulting solution was then concentrated under reduced pressure, diluted with water (50 mL) and extracted ethyl acetate (3×20 mL). Combined organic layers were dried over anhydrous sodium sulfate, filtered and concentrated to give the title compound (300 mg, 82%) as a yellow solid. LC/MS: 241.0 [M+H].

Intermediate 2: 3-(4-Amino-2-fluoro-phenyl)-1-methyl-1H-pyrazolo[3,4-d]pyrimidin-4-ylamine

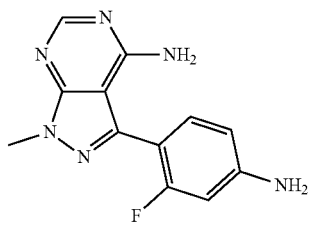 [SMILES: Cn1nc(-c2ccc(N)cc2F)c2c(N)ncnc21]

A mixture of 3-Bromo-1-methyl-1H-pyrazolo[3,4-d]pyrimidin-4-ylamine (231 mg; 1.01 mol, 1.2 eq), 3-Fluoro-4-(4,4,5,5-tetramethyl-[1,3,2]dioxaborolan-2-yl)-phenylamine (200 mg; 0.84 mmol, 1 eq), Pd(dppf)Cl$_2$·DCM (138 mg; 0.17 mmol; 0.2 eq) and cesium carbonate (605 mg; 1.8 mmol; 2.2 eq) in 1,4-dioxane (4 mL) and water (1 mL) was stirred overnight at 100° C. under nitrogen atmosphere. The reaction mixture was then filtered through a celite pad. The filtrate was diluted with EtOAc (50 mL) and washed with 1M NaOH (2×30 mL) and brine (2×30 mL). The organic layer was dried over sodium sulfate, filtered and concentrated. Purification by flash chromatography on silica (DCM:MeOH, gradient 99:1 to 80:20) afforded the title compound (95 mg, 44%) as a brown solid. LC/MS: 259.1 [M+H].

Intermediate 3: 3-(4-Amino-3-fluoro-phenyl)-1-methyl-1H-pyrazolo[3,4-d]pyrimidin-4-ylamine

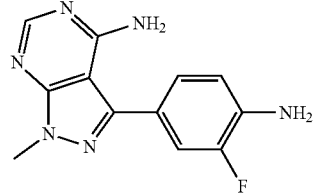

The title compound was obtained following a similar procedure as described for intermediate 2 but starting from 2-Fluoro-4-(4,4,5,5-tetramethyl-[1,3,2]dioxaborolan-2-yl)-phenylamine (200 mg; 0.84 mmol) as a white solid (90 mg, 41%).

Intermediate 4: 3-(4-Amino-3-chloro-phenyl)-1-methyl-1H-pyrazolo[3,4-d]pyrimidin-4-ylamine

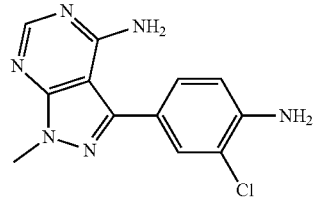 [SMILES: Cn1nc(-c2ccc(N)c(Cl)c2)c2c(N)ncnc21]

The title compound was obtained following a similar procedure as described for intermediate 2 but starting from 4-amino-3-chlorophenylboronic acid pinacol ester (200 mg; 0.79 mmol) as a white solid (111 mg, 51%). 1H NMR (400 MHz, DMSO-d6) δ 9.12 (s, 1H), 8.88 (s, 1H), 8.33 (t, J=8.4 Hz, 1H), 8.26 (s, 1H), 7.48-7.34 (m, 6H), 6.42 (s, 1H), 5.76 (s, 1H), 3.95 (s, 3H), 2.40 (s, 3H), 1.29 (s, 9H). UPLC: (254 nm) 100% purity; Rt 1.66 min. UPLC/MS: 275.2 [M+H].

Intermediate 5: 5-(4-Amino-2-fluoro-phenyl)-thieno[2,3-d]pyrimidin-4-ylamine

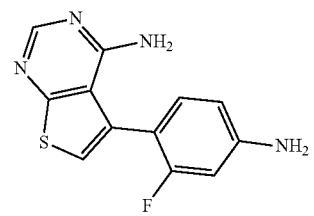 [SMILES: Nc1ccc(-c2csc3ncnc(N)c23)c(F)c1]

The title compound was obtained following a similar procedure as described for intermediate 2 but starting from 5-Bromo-thieno[2,3-d]pyrimidin-4-ylamine (233 mg; 1.0 mmol) and 4-amino-2-fluorophenylboronic acid pinacol ester (200 mg; 0.84 mmol) as a yellow oil (126 mg, 57%).

Intermediate 6: 5-(4-Amino-3-fluoro-phenyl)-thieno[2,3-d]pyrimidin-4-ylamine

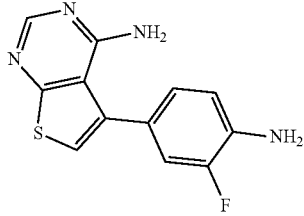 [SMILES: Nc1ccc(-c2csc3ncnc(N)c23)cc1F]

The title compound was obtained following a similar procedure as described for intermediate 2 but starting from 4-amino-3-fluorophenylboronic acid pinacol ester (200 mg; 0.84 mmol) and 5-Bromo-thieno[2,3-d]pyrimidin-4-ylamine (233 mg; 1.0 mmol) as a white solid (132 mg, 60%).

Intermediate 7: 3-(4-Amino-2-chloro-phenyl)-1-methyl-1H-pyrazolo[3,4-d]pyrimidin-4-ylamine

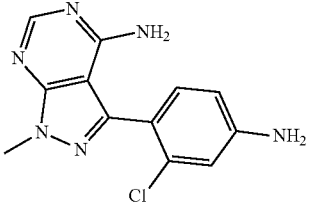 [SMILES: Cn1nc(-c2ccc(N)cc2Cl)c2c(N)ncnc21]

The title compound was obtained following a similar procedure as described for intermediate 2 but starting from 3-Bromo-1-methyl-1H-pyrazolo[3,4-d]pyrimidin-4-ylamine (216 mg; 1.0 mmol) and 3-chloro-4-(4,4,5,5-tetramethyl-1,3,2-dioxaborolan-2-yl)aniline (200 mg; 0.79 mmol) as a white solid (169 mg, 78%).

Intermediate 8: 3-{3-tert-butyl-1-[4-(propan-2-yl)phenyl]-1H-pyrazol-5-yl}-1-[2-fluoro-4-(tetramethyl-1,3,2-dioxaborolan-2-yl)phenyl]urea

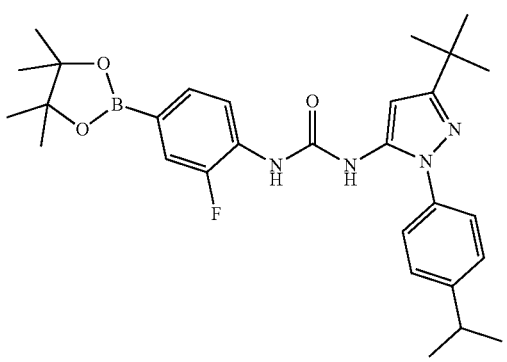 [SMILES: CC(C)c1ccc(-n2nc(C(C)(C)C)cc2NC(=O)Nc2ccc(B3OC(C)(C)C(C)(C)O3)cc2F)cc1]

A solution of 4-nitrophenyl chloroformate (440 mg, 2.07 mmol, 1.0 eq), dichloromethane (5 mL), pyridine (235 mg, 2.91 mmol, 1.4 eq) and 3-tert-butyl-1-[4-(propan-2-yl)phenyl]-1H-pyrazol-5-amine (prepared as described in Molecules, 2014, Volume 19, Issue 2, 2004-2028, 520 mg, 1.92 mmol, 0.93 eq) in DCM (5 mL) maintained under nitrogen atmosphere was stirred at 5° C. for 2 h before the addition of 2-fluoro-4-(tetramethyl-1,3,2-dioxaborolan-2-yl)aniline (470 mg, 1.88 mmol, 0.9 eq) and DIEA (520 mg, 3.94 mmol, 1.9 eq). The resulting reaction mixture was stirred for an additional 3 h at RT. The solvent was removed under reduced pressure and the crude was purified by flash chromatography on silica (EtOAc:PE; 1:1) to afford the title compound as a yellow solid (300 mg, 19%).

Intermediate 9: 5-(4-Amino-2-chloro-phenyl)-thieno[2,3-d]pyrimidin-4-ylamine

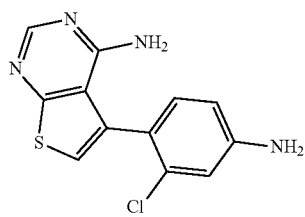 [SMILES: Nc1ccc(-c2csc3ncnc(N)c23)c(Cl)c1]

The title compound was obtained following a similar procedure as described for intermediate 2 but starting from 5-Bromo-thieno[2,3-d]pyrimidin-4-ylamine (218 mg; 0.95 mmol; 1.2 eq) and 3-chloro-4-(4,4,5,5-tetramethyl-1,3,2-dioxaborolan-2-yl)aniline (200 mg; 0.79 mmol; 1.0 eq) as a white amorphous solid (71 mg, 32%).

Intermediate 10: 5-(4-Amino-2-chloro-phenyl)-thieno[2,3-d]pyrimidin-4-ylamine

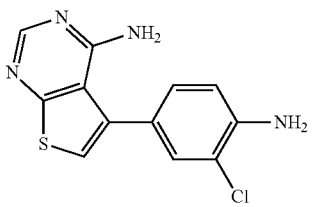 [SMILES: Nc1ccc(-c2csc3ncnc(N)c23)cc1Cl]

The title compound was obtained following a similar procedure as described for intermediate 2 but starting from 5-Bromo-thieno[2,3-d]pyrimidin-4-ylamine (218 mg; 0.95 mmol; 1.20 eq.) and 3-chloro-4-(4,4,5,5-tetramethyl-1,3,2-dioxaborolan-2-yl)aniline (200 mg; 0.79 mmol; 1.0 eq) as a yellow oil (71 mg, 32%).

Intermediate 11: 1-(5-tert-Butyl-2-p-tolyl-2H-pyrazol-3-yl)-3-[4-(4,4,5,5-tetramethyl-[1,3,2]dioxaborolan-2-yl)-phenyl]-urea

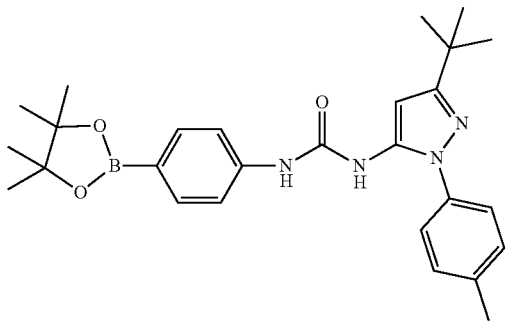

A solution of (4-isocyanatophenyl)boronic acid, pinacol ester (200 mg; 0.82 mmol; 1.0 eq) in DCM (1 mL) was added slowly to a solution of 5-tert-Butyl-2-p-tolyl-2H-pyrazol-3-ylamine (187 mg; 0.82 mmol; 1.0 eq) in DCM (17 mL) maintained under nitrogen atmosphere and at 0° C. The reaction mixture was then allowed to warm at RT and stirred for 16 h. The solvent was removed under reduced pressure and the crude was purified by Preparative HPLC (column C18 X-Bridge 30×250 mm, 10 um, gradient 30-95% ACN with 0.1% ammonium hydroxide) to give the title compound as a white solid (172 mg, 45%).

Intermediate 12: 3-iodo-1-methyl-1H-pyrazolo[4,3-c]pyridin-4-amine

Step 1: N-[(2,4-dimethoxyphenyl)methyl]-3-iodo-1H-pyrazolo[4,3-c]pyridin-4-amine

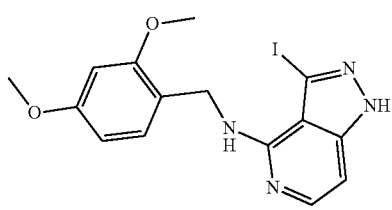

A solution of 4-chloro-3-iodo-1H-pyrazolo[4,3-c]pyridine (1.10 g, 3.74 mmol, 1.00 eq) and (2,4-dimethoxyphenyl)methanamine (1.97 g, 11.2 mmol, 3.0 eq) in DMSO (20 mL) was stirred O/N at 120° C. under nitrogen atmosphere. The reaction mixture was then diluted with water (30 mL) and extracted with DCM (2×30 mL). Combined organic layers were washed with brine, dried over anhydrous sodium sulfate, filtered and concentrated. Purification by flash chromatography on silica (DCM:MeOH, gradient 100:1 to 10:1) afforded the title compound as a brown solid (1.3 g, 67%). LC/MS: 410.9 [M+H].

Step 2: 3-iodo-1H-pyrazolo[4,3-c]pyridin-4-amine

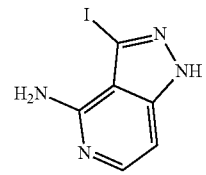

A solution of N-[(2,4-dimethoxyphenyl)methyl]-3-iodo-1H-pyrazolo[4,3-c]pyridin-4-amine (1.3 g, 2.54 mmol, 1.0 eq) in TFA (10 mL) was heated for 3 h at 50° C. TFA was then removed under reduced pressure and the resulting oil was diluted with EtOAc (50 mL). It was washed with sodium bicarbonate (30 mL), dried over anhydrous sodium sulfate, filtered and concentrated to give the title compound as a brown solid (450 mg, 58%). LC/MS: 260.8 [M+H].

Step 3: 3-iodo-1-methyl-1H-pyrazolo[4,3-c]pyridin-4-amine

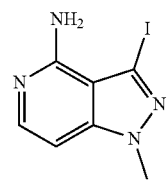

A mixture of 3-iodo-1H-pyrazolo[4,3-c]pyridin-4-amine (100 mg, 0.33 mmol, 1.0 eq), sodium hydride (19 mg, 0.79 mmol, 1.20 equiv) and MeI (56 mg, 0.39 mmol, 1.2 eq) was stirred for 2 h at RT in DMF (3 mL). The reaction was then quenched by the addition of 5 mL of sat. NH$_4$Cl and extracted with DCM (2×10 mL). Combined organic layers were washed with brine (2×10 mL), dried over anhydrous sodium sulfate, filtered and concentrated. Purification by flash chromatography on silica (EtOAc:PE, gradient from 1:10 to 1:1) afforded the title compound as a brown solid (60 mg, 62%). LC/MS (Column Kinetex EVO C18 100 A, 3.0×50 mm, 2.6 um; water/5 mM NH$_4$HCO$_3$/Acetonitrile from 10 to 95%, 254 nm): 93% purity; 274.7 [M+H].

Intermediate 13: 3-{3-tert-butyl-1-[4-(propan-2-yl)phenyl]-1H-pyrazol-5-yl}-1-[4-(tetramethyl-1,3,2-dioxaborolan-2-yl)phenyl]urea

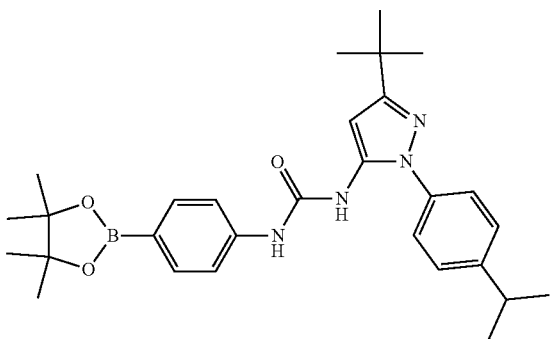

The title compound was obtained following a similar procedure as described for intermediate 8 but starting from 3-tert-butyl-1-[4-(propan-2-yl)phenyl]-1H-pyrazol-5-amine (520 mg, 1.92 mmol, 1.00 eq) and 4-(tetramethyl-1,3,2-dioxaborolan-2-yl)aniline (440 mg, 1.91 mmol, 0.99 eq) as a yellow solid (600 mg, 59%). LC/MS (Column Shim-pack XR-ODS, 3.0×50 mm, 2.2 um; Water/ACN with 0.05% TFA, gradient from 5 to 100% in 2.2 min, hold 1.0 min; 254 nm): 86.0% purity; 503.2 [M+H].

Intermediate 14: N-{3-tert-butyl-1-[4-(propan-2-yl)phenyl]-1H-pyrazol-5-yl}-2-[4-(tetramethyl-1,3,2-dioxaborolan-2-yl)phenyl]acetamide

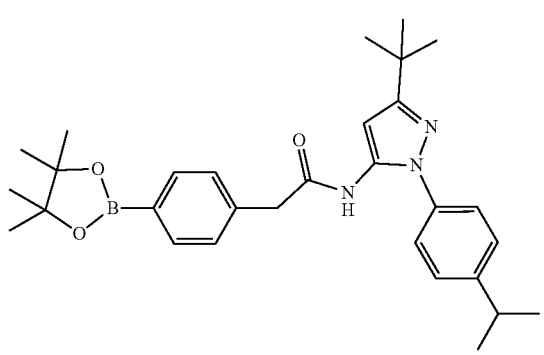

A solution of HATU (228 mg, 0.57 mmol, 1.05 eq) in DMF (2 mL) was added dropwise to a solution of 2-[4-(tetramethyl-1,3,2-dioxaborolan-2-yl)phenyl]acetic acid (150 mg, 0.54 mmol, 1.0 eq), 3-tert-butyl-1-[4-(propan-2-yl)phenyl]-1H-pyrazol-5-amine (180 mg, 0.63 mmol, 1.16 eq) and DIEA (222 mg, 1.63 mmol, 3.0 eq) in DMF (3 mL). The reaction mixture was then stirred at 15° C. for 16 h and concentrated under reduced pressure. Purification by preparative TLC on silica (PE:EtOAc, 5:1) afforded the title compound as a yellow oil (65 mg, 16%). LC/MS: 502.4 [M+H].

Intermediate 15: N-{3-tert-butyl-1-[4-(propan-2-yl)phenyl]-1H-pyrazol-5-yl}-2-[2-fluoro-4-(tetramethyl-1,3,2-dioxaborolan-2-yl)phenyl]acetamide Step 1: 2-(4-bromo-2-fluorophenyl)-N-{3-tert-butyl-1-[4-(propan-2-yl)phenyl]-1H-pyrazol-5-yl}acetamide

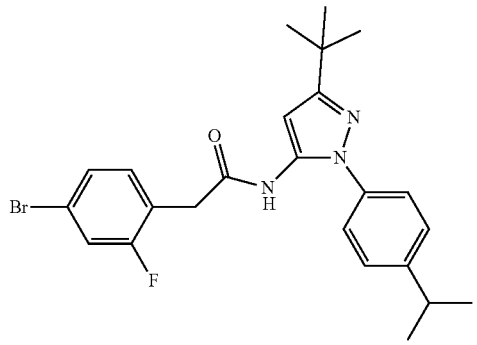

The title compound was obtained following a similar procedure as described for intermediate 14 but starting from 4-bromo-2-fluorobenzoic acid (500 mg, 2.17 mmol, 1.0 eq) and 3-tert-butyl-1-[4-(propan-2-yl)phenyl]-1H-pyrazol-5-amine (611 mg, 2.26 mmol, 1.0 eq) as a yellow solid (1.38 g, 100%). LC/MS (Column Kinetex EVO C18 100 A, 3.0×50 mm, 2.6 um; water/5 mM NH$_4$HCO$_3$/Acetonitrile from 10 to 95%, 254 nm): 76.0% purity; 472.2 [M+H].

Step 2: N-{3-tert-butyl-1-[4-(propan-2-yl)phenyl]-1H-pyrazol-5-yl}-2-[2-fluoro-4-(tetramethyl-1,3,2-dioxaborolan-2-yl)phenyl]acetamide

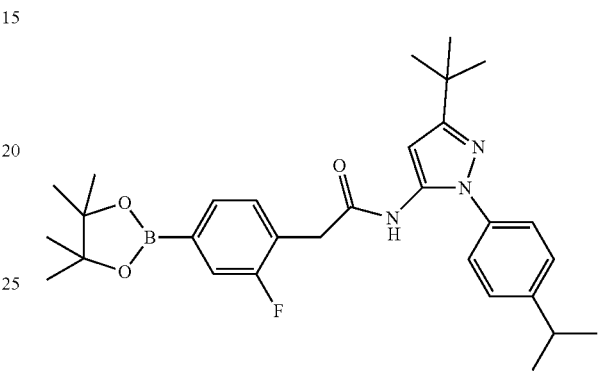

A mixture of 2-(4-bromo-2-fluorophenyl)-N-[3-tert-butyl-1-[4-(propan-2-yl)phenyl]-1H-pyrazol-5-yl]acetamide (200 mg, 0.32 mmol, 1.0 eq), 4,4,5,5-tetramethyl-2-(tetramethyl-1,3,2-dioxaborolan-2-yl)-1,3,2-dioxaborolane (133 mg, 0.50 mmol, 1.55 eq), Pd(dppf)Cl$_2$·CH$_2$Cl$_2$ (33 mg, 0.04 mmol, 0.12 eq) and AcOK (66 mg, 0.64 mmol, 2.0 eq) in dioxane (5 mL) in a sealed tube was purged with nitrogen before being heated at 100° C. for 3.5 h. Solvent was then removed under reduced pressure and the residue was diluted with DCM, washed with brine, dried over anhydrous sodium sulfate, filtered and concentrated to give the title compound as a black oil (300 mg, 100%). LC/MS: 520.3 [M+H].

Intermediate 16: 2-[5-({[2-chloro-4-(tetramethyl-1,3,2-dioxaborolan-2-yl)phenyl]carbamoyl}amino)-1-(4-methylphenyl)-1H-pyrazol-3-yl]-2-methylpropyl acetate

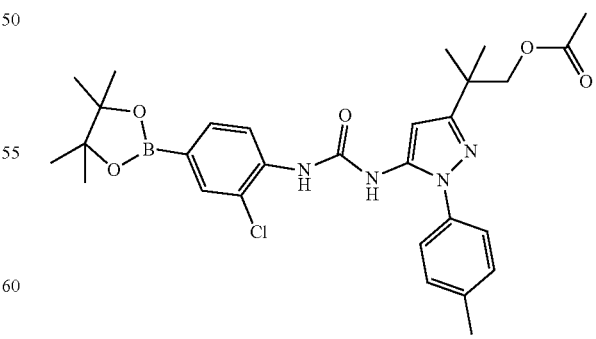

The title compound was obtained following a similar procedure as described for intermediate 8 but starting from 2-[5-amino-1-(4-methylphenyl)-1H-pyrazol-3-yl]-2-methylpropyl acetate (prepared as described in Journal of Medicinal Chemistry, 46(22), 4676-4686; 2003; 290 mg, 0.96 mmol, 0.93 eq) and 2-chloro-4-(tetramethyl-1,3,2-dioxaborolan-2-yl)aniline (250 mg, 0.94 mmol, 0.90 eq) as yellow solid (300 mg, 51%). LC/MS: 567.2 [M+H].

Intermediate 17: 3-(3-methyloxetan-3-yl)-1-(4-methylphenyl)-1H-pyrazol-5-amine

Step 1: 3-(3-methyloxetan-3-yl)-3-oxopropanenitrile

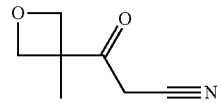

A solution of t-BuOK (9 g, 78.60 mmol, 2.00 eq) in THF (30 mL) was added dropwise to a solution of benzyl 3-methyloxetane-3-carboxylate (9 g, 39.28 mmol, 1.0 eq) and MeCN (2.1 mL, 39.95 mmol, 1.02 equiv) in THF (100 mL) maintained under nitrogen atmosphere. The reaction mixture was stirred for 16 h at 25° C. It was then concentrated under reduced pressure and purified by flash chromatography on silica (EtOAc:PE, gradient from 1:4 to 1:2) to give the title compound as a yellow oil (4.0 g, 66%).

Step 2: 3-(3-methyloxetan-3-yl)-1-(4-methylphenyl)-1H-pyrazol-5-amine

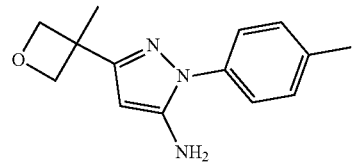 [SMILES: Cc1ccc(-n2nc(C3(C)COC3)cc2N)cc1]

A solution of 3-(3-methyloxetan-3-yl)-3-oxopropanenitrile (7.8 g, 50.4 mmol, 1.0 eq), (4-methylphenyl)hydrazine hydrochloride (8.17 g, 50.5 mmol, 1.0 eq) and AcOH (310 mg, 5.06 mmol, 0.1 eq) in EtOH (150 mL) was stirred for 16 h at 50° C. The solvent was removed under reduced pressure and purification by flash chromatography on silica (EtOAc:PE, gradient from 1:4 to 1:2) then on a C18-silica gel column (MeOH:water, gradient from 1:4 to 1:3) to give the title compound as a yellow solid (1 g, 9%). 1H NMR (300 MHz, DMSO-d6) δ 7.45 (d, J=8.4 Hz, 2H), 7.26 (d, J=8.1 Hz, 2H), 5.46 (s, 1H), 5.27 (s, 2H), 4.78 (d, J=5.2 Hz, 2H), 4.40 (d, J=5.2 Hz, 2H), 2.34 (s, 3H), 1.59 (s, 3H). LC/MS (Column Kinetex EVO C18 100 A, 3.0×50 mm, 2.6 um; water/5 mM NH4HCO3/Acetonitrile from 10 to 95%, 254 nm): 97% purity; 244.2 [M+H]; mp: 136-140° C.

Intermediate 18: 1-[2-chloro-4-(tetramethyl-1,3,2-dioxaborolan-2-yl)phenyl]-3-[3-(3-methyloxetan-3-yl)-1-(4-methylphenyl)-1H-pyrazol-5-yl]urea

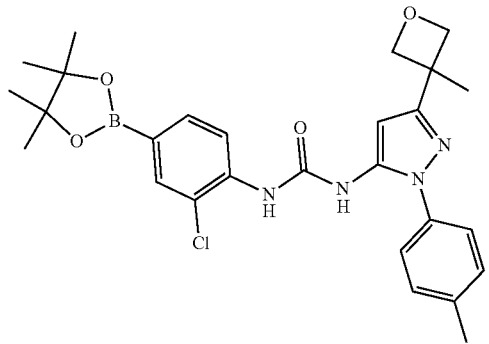

The title compound was obtained following a similar procedure as described for intermediate 8 but starting from 3-(3-methyloxetan-3-yl)-1-(4-methylphenyl)-1H-pyrazol-5-amine (101 mg, 0.40 mmol, 1.0 eq) and 2-chloro-4-(tetramethyl-1,3,2-dioxaborolan-2-yl)aniline (114 mg, 0.40 mmol, 1.01 eq) as a yellow solid (140 mg, 54%). LC/MS (Column Phenomenex Kinetext 3.0×50 mm, 2.7 um; Water/ACN with 0.05% TFA; gradient from 5% to 100% in 1.1 min, hold 0.5 min; 254 nm): 80% purity; 523.3 [M+H].

Intermediate 19: N-[3-tert-butyl-1-(4-methylphenyl)-1H-pyrazol-5-yl]-2-hydroxy-2-[4-(tetramethyl-1,3,2-dioxaborolan-2-yl)phenyl]acetamide Step 1: N-[3-tert-butyl-1-(4-methylphenyl)-1H-pyrazol-5-yl]-2-[4-(tetramethyl-1,3,2-dioxaborolan-2-yl)phenyl]-2-[(trimethylsilyl)oxy]acetamide

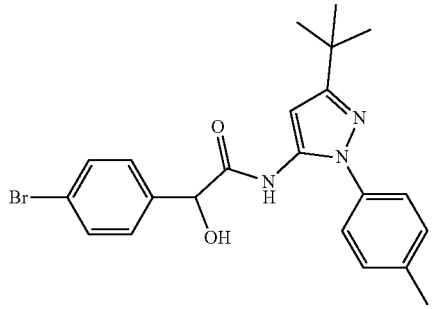

Chlorotrimethylsilane (188 mg, 1.64 mmol, 2.0 eq) was added to a solution of 2-(4-bromophenyl)-2-hydroxyacetic acid (200 mg, 0.82 mmol, 1.00 eq), 4-dimethylaminopyridine (10.6 mg, 0.08 mmol, 0.10 eq) and pyridine (137 mg, 1.65 mmol, 2.00 eq) in DCM (2 mL) maintained under nitrogen atmosphere. The reaction mixture was stirred at RT for 4 h. It was then cooled down to 0° C. DMF (0.2 mL) followed by Oxalyl chloride (115 mg, 0.86 mmol, 1.05 eq) were added dropwise and the reaction mixture was stirred for 1 h at 0° C. It was allowed to warm to RT before the addition of a solution of 3-tert-butyl-1-(4-methylphenyl)-1H-pyrazol-5-amine (218 mg, 0.86 mmol, 1.04 eq) in pyridine (0.2 mL) and stirred for an additional 2 h at 15° C. After dilution with water, the mixture was extracted with DCM (3×5 mL). Combined organic layers were washed with sat. NaHCO₃ and brine, dried over anhydrous sodium sulfate, filtered and concentrated. Purification on preparative TLC (PE:EtOAc, 5:1) afforded the title compound a as yellow solid (95 mg, 24%).

Step 2: N-[3-tert-butyl-1-(4-methylphenyl)-1H-pyrazol-5-yl]-2-hydroxy-2-[4-(tetramethyl-1,3,2-dioxaborolan-2-yl)phenyl]acetamide

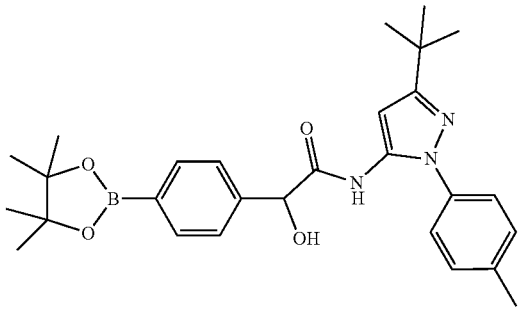

The title compound was obtained following a similar procedure as described for intermediate 15, step 2, but starting from 2-(4-bromophenyl)-N-[3-tert-butyl-1-(4-methylphenyl)-1H-pyrazol-5-yl]-2-hydroxyacetamide (85 mg, 0.17 mmol, 1.0 eq) as a yellow solid (80 mg, 58%). LC/MS: 490.4 [M+H].

Intermediate 20: 2-(5-Amino-1-p-tolyl-1H-pyrazol-3-yl)-2-methyl-propionitrile

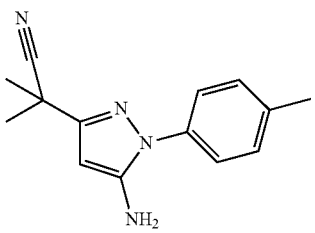 [SMILES: Cc1ccc(-n2nc(C(C)(C)C#N)cc2N)cc1]

The title compound was obtained following a similar procedure as described for intermediate 17, step 2, but starting from 2,2-Dimethyl-3-oxopentanedinitrile. LC/MS: 241.1 [M+H].

Intermediate 21: 2-Chloro-3-fluoro-4-(4,4,5,5-tetramethyl-[1,3,2]dioxaborolan-2-yl)-phenylamine

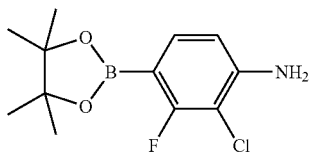 [SMILES: CC1(C)OB(c2ccc(N)c(Cl)c2F)OC1(C)C]

The title compound was obtained following a similar procedure as described for intermediate 15, step 2, but starting from 4-Bromo-2-chloro-3-fluoro-phenylamine (100 mg; 0.45 mmol) as a brown solid (100 mg, 83%). UPLC/MS: 272.3 [M+H].

Intermediate 22: 5-(4-Amino-3-chloro-2-fluorophenyl)-thieno[2,3-d]pyrimidin-4-ylamine

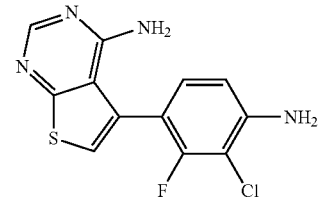 [SMILES: Nc1ccc(-c2csc3ncnc(N)c23)c(F)c1Cl]

The title compound was obtained following a similar procedure as described for intermediate 2 but starting from 5-Bromo-thieno[2,3-d]pyrimidin-4-ylamine (102 mg; 0.44 mmol; 1.2 eq) and 2-Chloro-3-fluoro-4-(4,4,5,5-tetramethyl-[1,3,2]dioxaborolan-2-yl)-phenylamine (100 mg; 0.37 mmol; 1 eq) as a yellow solid (31 mg, 29%).

Intermediate 23: 1-(4-methylphenyl)-3-(1,1,1-trifluoro-2-methylpropan-2-yl)-1H-pyrazol-5-amine

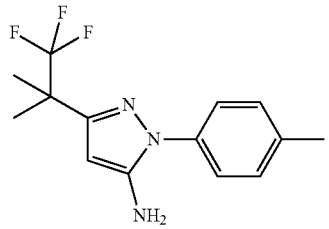 [SMILES: Cc1ccc(-n2nc(C(C)(C)C(F)(F)F)cc2N)cc1]

A solution of 5,5,5-trifluoro-4,4-dimethyl-3-oxopentanenitrile (4 g, 19 mmol, 1.0 eq) and (4-methylphenyl)hydrazine hydrochloride (3.3 g, 19.8 mmol, 1.04 eq) in EtOH (50 mL) was heated at 80° C. for 16 h. The solvent was removed under reduced pressure and the residue was purified by flash chromatography on C18-silica (water:MeOH; 1:1) to give the title compound as a yellow solid (2 g, 35%). 1H NMR (400 MHz, DMSO-d6) δ 7.43 (d, J=8.3 Hz, 2H), 7.28 (d, J=8.1 Hz, 2H), 5.50 (s, 1H), 5.29 (s, 2H), 2.34 (s, 3H), 1.4 (s, 6H). LC/MS: 284.1 [M+H]. mp: 90° C.

Intermediate 24: 5-(4-aminocyclohex-1-en-1-yl)-7-methyl-7H-pyrrolo[2,3-d]pyrimidin-4-amine Step 1: tert-butyl N-(4-{4-amino-7-methyl-7H-pyrrolo[2,3-d]pyrimidin-5-yl}cyclohex-3-en-1-yl)carbamate

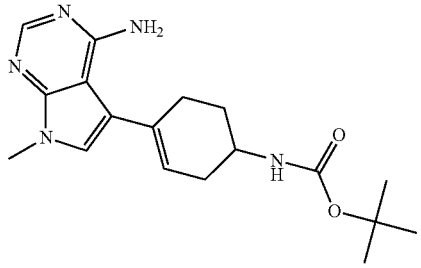 [SMILES: Cn1cc(C2=CCC(NC(=O)OC(C)(C)C)CC2)c2c(N)ncnc21]

The title compound was obtained following a similar procedure as described for intermediate 2 but starting from tert-butyl N-[4-(tetramethyl-1,3,2-dioxaborolan-2-yl)cyclohex-3-en-1-yl]carbamate (501 mg, 1.47 mmol, 1.20 eq) and 5-iodo-7-methyl-7H-pyrrolo[2,3-d]pyrimidin-4-amine (372 mg, 1.22 mmol, 1.00 eq) as a brown solid (200 mg, 43%). LC/MS (Column Ascentis Express C18, 3.0*×50 mm, 0.7 um; Water/ACN with 0.05% TFA gradient from 5 to 100% in 1.2 min, hold 0.5 min; 254 nm): 90% purity; 344.0 [M+H].

Step 2: 5-(4-aminocyclohex-1-en-1-yl)-7-methyl-7H-pyrrolo[2,3-d]pyrimidin-4-amine

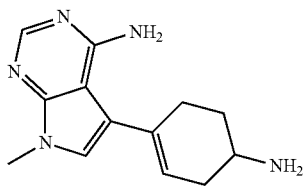 [SMILES: Cn1cc(C2=CCC(N)CC2)c2c(N)ncnc21]

A solution of tert-butyl N-(4-[4-amino-7-methyl-7H-pyrrolo[2,3-d]pyrimidin-5-yl]cyclohex-3-en-1-yl)carbamate (200 mg, 0.52 mmol, 1.0 equiv, 90%) and trifluoroacetic acid (1 mL) in DCM (5 mL) was stirred for 3 h at 25° C. The pH was then adjusted to 8 by addition of NH$_4$OH and the mixture was diluted with DCM (20 mL). Organic phase was washed with brine (2×20 mL), dried over anhydrous sodium sulfate, filtered and concentrated to give the title compound as a brown solid (130 mg, 92%). LC/MS (Column Ascentis Express C18, 3.0×50 mm, 2.7 um; Water/ACN with 0.05% TFA, Gradient from 5% to 100% in 1.2 min, hold 0.5 min; 254 nm): 90% purity; 244.0 [M+H].

Intermediate 25: 3-[3-tert-butyl-1-(4-methylphenyl)-1H-pyrazol-5-yl]-1-[2-fluoro-4-(tetramethyl-1,3,2-dioxaborolan-2-yl)phenyl]urea

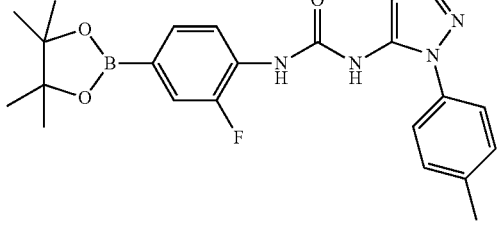

A solution of 3-tert-butyl-1-(4-methylphenyl)-1H-pyrazol-5-amine (300 mg, 1.18 mmol, 1.0 eq) and DIEA (641 mg, 4.7 mmol, 4.0 eq) in DCM (1 mL) was added dropwise to a solution of triphosgene (69 mg, 0.22 mmol, 0.6 eq) in DCM (5 mL) maintained at 0° C. and under nitrogen atmosphere. The reaction mixture was stirred for 20 min at 0° C. and added to a solution of 2-fluoro-4-(tetramethyl-1,3,2-dioxaborolan-2-yl)aniline (323 mg, 1.3 mmol, 1.1 eq) in DCM (3 mL). The resulting reaction mixture was stirred for 3 h at RT, washed with a saturated solution of NH$_4$Cl (2×10 mL) and brine (1×10 mL), dried over anhydrous sodium sulfate, filtered and concentrated. Purification by flash chromatography on silica (DCM:MeOH; 3:1) afforded the title compound as a brown solid (180 mg, 20%). LC/MS: 493.0 [M+H].

Example 1: 1-(4-{4-amino-1-methyl-1H-pyrazolo[3,4-d]pyrimidin-3-yl}phenyl)-3-{3-tert-butyl-1-[4-(propan-2-yl)phenyl]-1H-pyrazol-5-yl}urea (15)

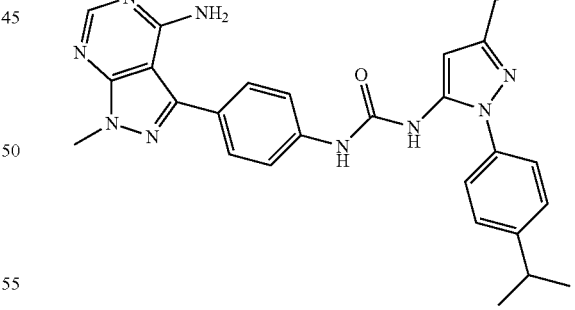

A solution of 3-tert-butyl-1-[4-(propan-2-yl)phenyl]-1H-pyrazol-5-amine (prepared as described in Molecules, 2014, Volume 19, Issue 2, 2004-2028, 257 mg, 1.00 mmol, 1.0 eq) in DCM (2 mL) was added dropwise to a solution of 4-nitrophenyl chloroformate (220 mg, 1.09 mmol, 1.1 eq) and pyridine (120 mg, 1.52 mmol, 1.6 eq) in DCM (20 mL) maintained at 5° C. 3-(4-aminophenyl)-1-methyl-1H-pyrazolo[3,4-d]pyrimidin-4-amine (intermediate 1, 240 mg, 1.00 mmol, 1.0 eq) and DIEA (260 mg, 2.01 mmol, 2.0 eq) were then added and the resulting reaction mixture was stirred at 25° C. for 16 h. It was then concentrated under vacuum and purified by Prep-HPLC (Column, Gemini-NX C18 AXAI, 21.2×150 mm, Sum; Water with 10 mM NH4HCO3 and ACN gradient from 40% to 63% in 10 min) to afford the title compound as a yellow solid (6 mg, 19%). 1H NMR (400 MHz, DMSO-d6): 9.24 (s, 1), 8.48 (s, 1), 8.25 (s, 1), 7.59 (m, 4), 7.43 (m, 4), 6.40 (s, 1), 3.94 (s, 3), 2.98 (t, 1, J=6.8 Hz), 1.28 (s, 9), 1.25 (d, 6, J=7.2 Hz); LC/MS (Column Shim-pack XR-ODS, 3.0×50 mm, 2.2 um; Water/CAN with 0.05% TFA, Gradient from 5 to 100% in 3.6 min, hold 1.0 min; 254 nm): (purity) 97.9%; 524.3 [M+H].

Example 2: 1-[4-(4-Amino-1-methyl-1H-pyrazolo[3,4-d]pyrimidin-3-yl)-3-fluoro-phenyl]-3-(5-tert-butyl-2-p-tolyl-2H-pyrazol-3-yl)-urea (2)

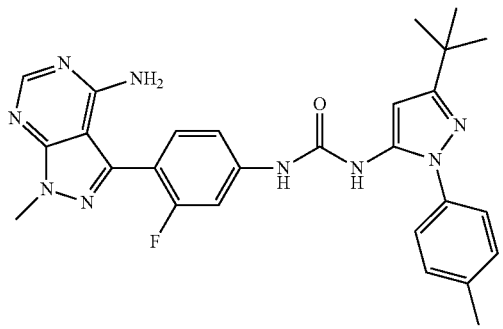 [SMILES: Cc1ccc(-n2nc(C(C)(C)C)cc2NC(=O)Nc2ccc(-c3nn(C)c4ncnc(N)c34)c(F)c2)cc1]

The title compound was obtained following a similar procedure as described for example 1 but starting from 5-tert-Butyl-2-p-tolyl-2H-pyrazol-3-ylamine (67 mg; 0.29 mmol; 1.5 eq) and 3-(4-Amino-2-fluoro-phenyl)-1-methyl-1H-pyrazolo[3,4-d]pyrimidin-4-ylamine (intermediate 2, 50 mg; 0.19 mmol; 1.0 eq) as a white solid (15 mg, 15%). 1H NMR (400 MHz, DMSO-d6) δ 9.12 (s, 1H), 8.88 (s, 1H), 8.33 (t, J=8.4 Hz, 1H), 8.26 (s, 1H), 7.48-7.34 (m, 6H), 6.42 (s, 1H), 5.76 (s, 1H), 3.95 (s, 3H), 2.40 (s, 3H), 1.29 (s, 9H). UPLC: (254 nm) 100% purity; Rt 3.5 min. UPLC/MS: 514.5 [M+H].

Example 3: 1-[4-(4-Amino-1-methyl-1H-pyrazolo[3,4-d]pyrimidin-3-yl)-3-fluoro-phenyl]-3-[5-tert-butyl-2-(4-isopropyl-phenyl)-2H-pyrazol-3-yl]-urea (11)

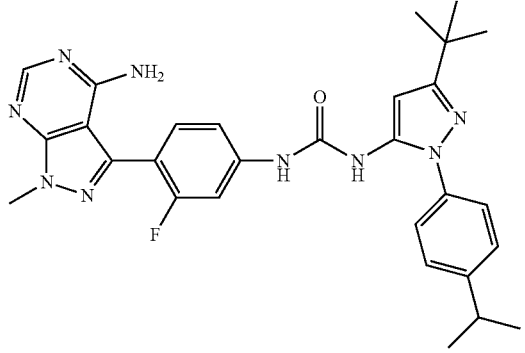 [SMILES: CC(C)c1ccc(-n2nc(C(C)(C)C)cc2NC(=O)Nc2ccc(-c3nn(C)c4ncnc(N)c34)c(F)c2)cc1]

The title compound was obtained following a similar procedure as described for example 1 but starting from 3-tert-butyl-1-[4-(propan-2-yl)phenyl]-1H-pyrazol-5-amine (86 mg, 0.32 mmol, 1.0 eq) as a white solid (20 mg, 12%). 1H NMR (300 MHz, DMSO-d6) δ 9.42 (s, 1H), 8.54 (s, 1H), 8.24 (s, 1H), 7.66-7.60 (m, 1H), 7.46-7.39 (m, 5H), 7.25-7.21 (m, 1H), 6.39 (s, 1H), 3.94 (s, 3H), 3.00-2.95 (m, 1H), 1.28 (s, 9H), 1.26-1.24 (d, J=6.9 Hz, 6H); LC/MS (Column Kinetex EVO C18 100 A, 3.0×50 mm, 2.6 um, water with 5 mM NH4HCO3/ACN, Gradient from 10% to 95% in 2.0 min, hold 0.5 min; 254 nm): 99.6% purity; 542.3 [M+H]. mp: 160.0 to 162.0° C.

Example 4: 1-[4-(4-Amino-1-methyl-1H-pyrazolo[3,4-d]pyrimidin-3-yl)-2-fluoro-phenyl]-3-(5-tert-butyl-2-p-tolyl-2H-pyrazol-3-yl)-urea (6)

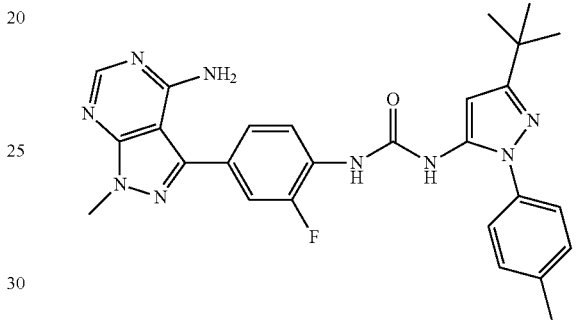

The title compound was obtained following a similar procedure as described for example 1 but starting from 5-tert-Butyl-2-p-tolyl-2H-pyrazol-3-ylamine (44 mg; 0.19 mmol; 1.0 eq) and 3-(4-Amino-3-fluoro-phenyl)-1-methyl-1H-pyrazolo[3,4-d]pyrimidin-4-ylamine (intermediate 3, 50 mg; 0.19 mmol; 1.0 eq) as a white solid (15 mg, 15%). 1H NMR (400 MHz, DMSO-d6) δ 9.12 (s, 1H), 8.88 (s, 1H), 8.33 (t, J=8.6 Hz, 1H), 8.26 (s, 1H), 7.50-7.31 (m, 6H), 6.42 (s, 1H), 3.95 (s, 3H), 2.40 (s, 3H), 1.29 (s, 8H). UPLC: (254 nm) 100% purity; Rt 3.5 min. UPLC/MS: 514.5 [M+H].

Example 5: 1-[4-(4-Amino-1-methyl-1H-pyrazolo[3,4-d]pyrimidin-3-yl)-2-chloro-phenyl]-3-(5-tert-butyl-2-p-tolyl-2H-pyrazol-3-yl)-urea (4)

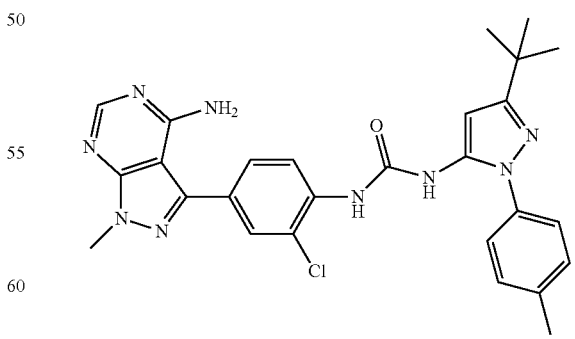

The title compound was obtained following a similar procedure as described for example 1 but starting from 5-tert-Butyl-2-p-tolyl-2H-pyrazol-3-ylamine (658 mg; 2.87 mmol; 1.0 eq) and 3-(4-Amino-3-chloro-phenyl)-1-methyl- 1H-pyrazolo[3,4-d]pyrimidin-4-ylamine (intermediate 4, 789 mg; 2.87 mmol; 1.0 eq) as white solid (41 mg, 3%). 1H NMR (400 MHz, DMSO-d6) δ 9.21 (s, 1H), 8.77 (s, 1H), 8.30 (d, J=8.6 Hz, 1H), 8.26 (s, 1H), 7.68 (d, J=2.1 Hz, 1H), 7.58 (dd, J=8.6, 2.1 Hz, 1H), 7.45-7.33 (m, 4H), 6.41 (s, 1H), 3.95 (s, 3H), 2.39 (s, 3H), 1.29 (s, 9H). UPLC: (254 nm) 100% purity; Rt 3.65 min. UPLC/MS: 530.5 [M+H].

Example 6: 1-[4-(4-Amino-thieno[2,3-d]pyrimidin-5-yl)-3-fluoro-phenyl]-3-(5-tert-butyl-2-p-tolyl-2H-pyrazol-3-yl)-urea (12)

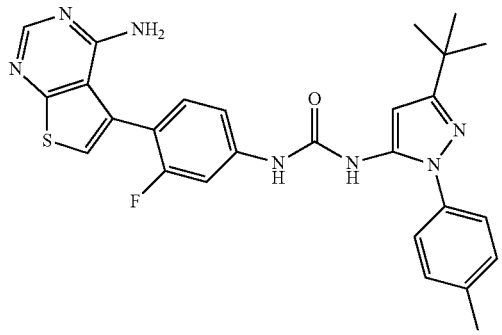 [SMILES: Cc1ccc(-n2nc(C(C)(C)C)cc2NC(=O)Nc2ccc(-c3csc4ncnc(N)c34)c(F)c2)cc1]

The title compound was obtained following a similar procedure as described for example 1 but starting from 5-tert-Butyl-2-p-tolyl-2H-pyrazol-3-ylamine (73 mg; 0.32 mmol) and 3-(4-Amino-2-fluoro-phenyl)-isothiazolo[5,4-d]pyrimidin-4-ylamine (intermediate 5, 83 mg; 0.32 mmol) as a white solid (34 mg, 20%). 1H NMR (400 MHz, DMSO-d6) δ 9.42 (s, 1H), 8.50 (s, 1H), 8.34 (s, 1H), 7.61 (dd, J=12.4, 2.1 Hz, 1H), 7.52 (s, 1H), 7.45-7.33 (m, 5H), 7.23 (dd, J=8.4, 2.1 Hz, 1H), 6.39 (s, 1H), 2.39 (s, 3H), 1.29 (s, 8H). UPLC: (254 nm) 100% purity; Rt 3.81 min. UPLC/MS: 516 [M+H].

Example 7: 1-[4-(4-Amino-thieno[2,3-d]pyrimidin-5-yl)-2-fluoro-phenyl]-3-(5-tert-butyl-2-p-tolyl-2H-pyrazol-3-yl)-urea (9)

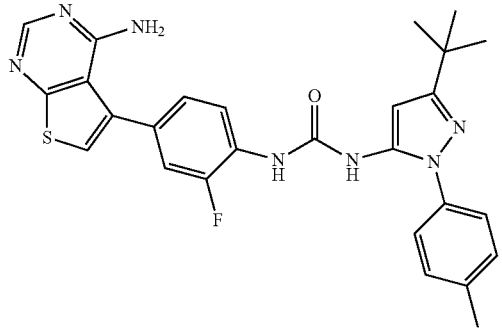 [SMILES: Cc1ccc(-n2nc(C(C)(C)C)cc2NC(=O)Nc2ccc(-c3csc4ncnc(N)c34)cc2F)cc1]

The title compound was obtained following a similar procedure as described for example 1 but starting from 5-tert-Butyl-2-p-tolyl-2H-pyrazol-3-ylamine (116 mg; 0.51 mmol) and 5-(4-Amino-3-fluoro-phenyl)-thieno[2,3-d]pyrimidin-4-ylamine (intermediate 6, 132 mg; 0.51 mmol) as a yellow solid (27 mg, 10%). 1H NMR (400 MHz, DMSO-d6) δ 9.10 (s, 1H), 8.88 (s, 1H), 8.35 (s, 1H), 8.29 (t, J=8.5 Hz, 1H), 7.49 (s, 1H), 7.44-7.34 (m, 5H), 7.29-7.19 (m, 1H), 6.41 (s, 1H), 2.40 (s, 3H), 1.29 (s, 10H). UPLC: (254 nm) 100% purity; Rt 3.7 min. UPLC/MS: 516 [M+H].

Example 8: 1-[4-(4-Amino-1-methyl-1H-pyrazolo[3,4-d]pyrimidin-3-yl)-3-chloro-phenyl]-3-(5-tert-butyl-2-p-tolyl-2H-pyrazol-3-yl)-urea (8)

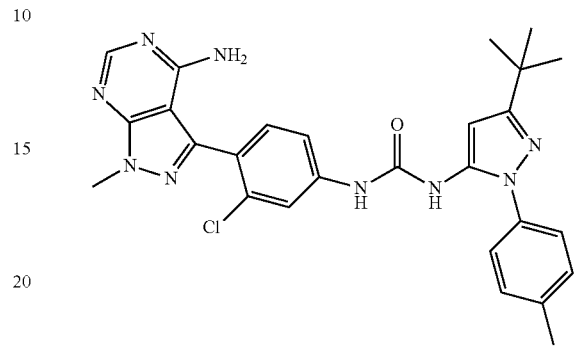

The title compound was obtained following a similar procedure as described for example 1 but starting from 5-tert-Butyl-2-p-tolyl-2H-pyrazol-3-ylamine (42 mg; 0.18 mmol) and 3-(4-Amino-2-chloro-phenyl)-1-methyl-1H-pyrazolo[3,4-d]pyrimidin-4-ylamine (intermediate 7, 50 mg, 0.18 mmol) as white solid (8 mg, 8%). 1H NMR (400 MHz, DMSO-d6) δ 9.39 (s, 1H), 8.48 (s, 1H), 8.24 (s, 1H), 7.86 (d, J=1.9 Hz, 1H), 7.49-7.24 (m, 5H), 6.39 (s, 1H), 3.94 (s, 3H), 2.39 (s, 3H), 1.30 (s, 9H). UPLC: (254 nm) 96% purity; Rt 3.63 min. UPLC/MS: 530.3 [M+H].

Example 9: 1-(4-{4-amino-1-methyl-1H-pyrazolo[3,4-d]pyrimidin-3-yl}-2-fluorophenyl)-3-{3-tert-butyl-1-[4-(propan-2-yl)phenyl]-1H-pyrazol-5-yl}urea (10)

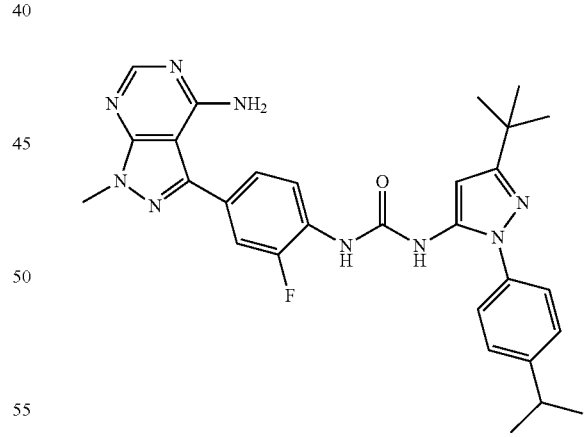

A mixture of 3-[3-tert-butyl-1-[4-(propan-2-yl)phenyl]-1H-pyrazol-5-yl]-1-[2-fluoro-4-(tetramethyl-1,3,2-dioxaborolan-2-yl)phenyl]urea (intermediate 8, 160 mg, 0.29 mmol, 1.0 eq), 3-iodo-1-methyl-1H-pyrazolo[3,4-d]pyrimidin-4-amine (101 mg, 0.35 mmol, 1.2 eq), Pd(dppf)Cl$_2$·CH$_2$Cl$_2$ (25 mg, 0.03 mmol, 0.10 eq) and KOAc (90.4 mg, 0.90 mmol, 3.1 eq) in dioxane (15 mL) and water (1.5 mL) was purged with nitrogen and heated in MW for 1 h at 80° C. in a sealed tube. Solvent was removed under reduced pressure and the residue was purified by flash chromatography on silica (DCM:MeOH, 20:1) to afford the title compound as a white solid (30 mg, 19%). mp: 166-168° C. 1H NMR (400 MHz, DMSO-d6) δ 9.13-9.12 (m, 1H), 8.94 (s, 1H), 8.34-8.30 (m, 1H), 8.24 (s, 1H), 7.45-7.41 (m, 6H), 6.40 (s, 1H), 3.92 (s, 3H), 2.99-2.95 (m, 1H), 1.26-1.23 (m, 15H). LC/MS (Column XBridge C18, 4.6×50 mm, 3.5 um; Water with 5 mM NH$_4$HCO$_3$/ACN; Gradient from 10% to 95% in 1.2 min, hold 1.0 min; 254 nm): 99% (purity); 542.2 [M+H].

Example 10: 1-[4-(4-Amino-thieno[2,3-d]pyrimidin-5-yl)-3-chloro-phenyl]-3-(5-tert-butyl-2-p-tolyl-2H-pyrazol-3-yl)-urea (14)

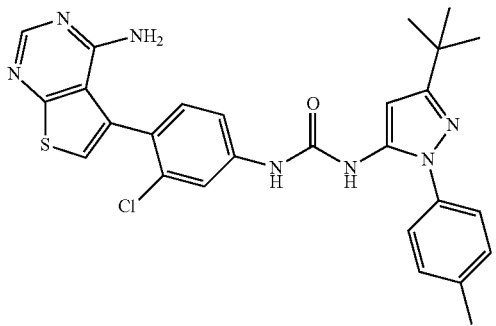 [SMILES: Cc1ccc(-n2nc(C(C)(C)C)cc2NC(=O)Nc2ccc(-c3csc4ncnc(N)c34)c(Cl)c2)cc1]

The title compound was obtained following a similar procedure as described for example 1 but starting from 5-tert-Butyl-2-p-tolyl-2H-pyrazol-3-ylamine (58 mg; 0.26 mmol; 1.0 eq) and 5-(4-Amino-2-chloro-phenyl)-thieno[2,3-d]pyrimidin-4-ylamine (intermediate 9, 71 mg; 0.26 mmol; 1.0 eq) as a yellow foam (12 mg, 12%). 1H NMR (400 MHz, DMSO-d6) δ 9.41 (s, 1H), 8.50 (s, 1H), 8.34 (s, 1H), 7.87 (d, J=2.0 Hz, 1H), 7.48 (s, 1H), 7.44-7.32 (m, 6H), 6.39 (s, 1H), 2.39 (s, 3H), 1.29 (s, 9H). UPLC: (254 nm) 100% purity; Rt 3.97 min. LC/MS: 533.2 [M+H].

Example 11: 1-[4-(4-Amino-thieno[2,3-d]pyrimidin-5-yl)-2-chloro-phenyl]-3-(5-tert-butyl-2-p-tolyl-2H-pyrazol-3-yl)-urea (20)

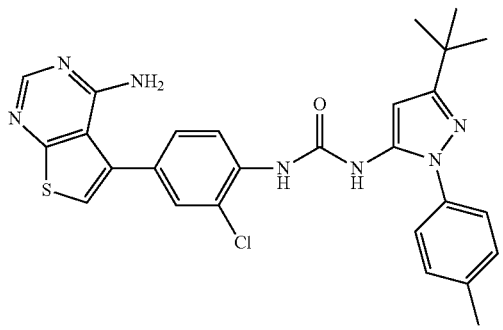 [SMILES: Cc1ccc(-n2nc(C(C)(C)C)cc2NC(=O)Nc2ccc(-c3csc4ncnc(N)c34)cc2Cl)cc1]

The title compound was obtained following a similar procedure as described for example 1 but starting from 5-tert-Butyl-2-p-tolyl-2H-pyrazol-3-ylamine (76 mg; 0.33 mmol; 1.0 eq) and 5-(4-Amino-3-chloro-phenyl)-thieno[2,3-d]pyrimidin-4-ylamine (Intermediate 10, 91 mg; 0.33 mmol; 1.0 eq) as a yellow foam (10 mg, 5%). 1H NMR (400 MHz, DMSO-d6) δ 9.20 (s, 1H), 8.78 (s, 1H), 8.35 (s, 1H), 8.26 (d, J=8.5 Hz, 1H), 7.58 (d, J=2.1 Hz, 1H), 7.52 (s, 1H), 7.44-7.34 (m, 5H), 6.40 (s, 1H), 2.39 (s, 3H), 1.29 (s, 8H). UPLC: (254 nm) 99% purity; Rt 3.93 min. LC/MS: 533.2 [M+H].

Example 12: 1-[4-(4-Amino-thieno[2,3-d]pyrimidin-5-yl)-phenyl]-3-(5-tert-butyl-2-p-tolyl-2H-pyrazol-3-yl)-urea (13)

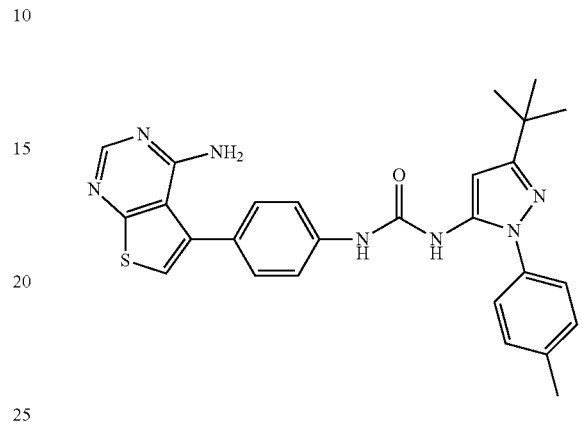

A mixture of 5-Bromo-thieno[2,3-d]pyrimidin-4-ylamine (100 mg; 0.43 mmol; 1.2 eq), 1-(5-tert-Butyl-2-p-tolyl-2H-pyrazol-3-yl)-3-[4-(4,4,5,5-tetramethyl-[1,3,2]dioxaborolan-2-yl)-phenyl]-urea (172 mg; 0.36 mmol; 1.0 eq), Pd(dppf)Cl$_2$·DCM (59 mg; 0.73 mmol; 0.2 eq) and cesium carbonate (260 mg; 0.8 mmol; 2.2 eq) in 1,4-dioxane (3.5 mL) and water (1 mL) was stirred overnight at 100° C. under nitrogen atmosphere. The reaction mixture was then filtered through a celite pad. The filtrate was diluted with EtOAc (50 mL) and washed with 1M NaOH (2×30 mL) and brine (2×30 mL). The organic layer was dried over sodium sulfate, filtered and concentrated. Purification by Preparative HPLC (column C18 X-Bridge 30×250 mm, 10 um, gradient 30-95 ACN with 0.1% ammonium hydroxide) afforded the title compound as a white powder (41 mg, 23%). 1H NMR (400 MHz, DMSO-d6) δ 9.22 (s, 1H), 8.44 (s, 1H), 8.34 (s, 1H), 7.57 (d, J=8.6 Hz, 2H), 7.48-7.28 (m, 7H), 6.38 (s, 1H), 2.39 (s, 3H), 1.29 (s, 9H). UPLC: (254 nm) 100% purity; Rt 3.63 min. LC/MS: 598.3 [M+H].

Example 13: 1-[4-(4-Amino-1-methyl-1H-pyrazolo[3,4-d]pyrimidin-3-yl)-3-fluoro-phenyl]-3-(2-p-tolyl-5-trifluoromethyl-2H-pyrazol-3-yl)-urea (26)

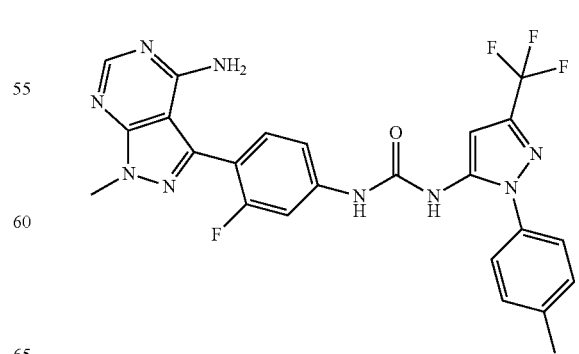

The title compound was obtained following a similar procedure as described for example 1 but starting from 2-p-Tolyl-5-trifluoromethyl-2H-pyrazol-3-ylamine (56 mg; 0.23 mmol; 1.0 eq) and 3-(4-Amino-2-fluoro-phenyl)-1-methyl-1H-pyrazolo[3,4-d]pyrimidin-4-ylamine (Intermediate 2, 60 mg; 0.23 mmol; 1.0 eq) as a white powder (7 mg, 6%). 1H NMR (400 MHz, DMSO-d6) δ 9.24 (s, 1H), 9.20 (s, 1H), 8.31 (t, J=8.6 Hz, 1H), 8.26 (s, 1H), 7.57-7.39 (m, 6H), 6.91 (s, 1H), 3.95 (s, 3H), 2.44 (s, 3H). UPLC: (254 nm) 100% purity; Rt 3.72 min. LC/MS: 525.2 [M+H].

Example 14: 1-[4-(4-Amino-1-methyl-1H-pyrazolo[4,3-c]pyridin-3-yl)-phenyl]-3-[5-tert-butyl-2-(4-isopropyl-phenyl)-2H-pyrazol-3-yl]-urea (16)

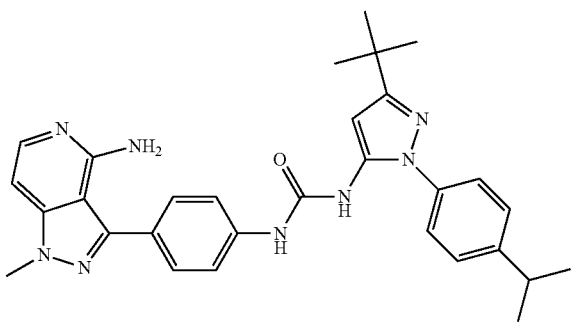 [SMILES: CC(C)c1ccc(-n2nc(C(C)(C)C)cc2NC(=O)Nc2ccc(-c3nn(C)c4ccnc(N)c34)cc2)cc1]

The title compound was obtained following a similar procedure as described for example 9 but starting from 3-[3-tert-butyl-1-[4-(propan-2-yl)phenyl]-1H-pyrazol-5-yl]-1-[4-(tetramethyl-1,3,2-dioxaborolan-2-yl)phenyl]urea (intermediate 13, 200 mg, 0.38 mmol, 1.0 eq) and 3-iodo-1-methyl-1H-pyrazolo[4,3-c]pyridin-4-amine (intermediate 12, 130 mg, 0.45 mmol, 1.2 eq) as a white solid (20 mg, 10%). 1H NMR (400 MHz, DMSO-d6): δ 9.22 (s, 1H), 8.48 (s, 1H), 7.74-7.73 (d, J=6 Hz, 1H), 7.59-7.51 (m, 4H), 7.44-7.38 (m, 4H), 6.83-6.82 (d, J=6 Hz, 1H), 6.38 (s, 1H), 5.74 (s, 2H), 3.94 (s, 3H), 2.98-2.95 (m, 1H), 1.27 (s, 9H), 1.25-1.23 (d, J=6.8 Hz, 6H); LC/MS (Column Kinetex 2.6u XB-C18 100 A, 3.0×50 mm, 2.6 um; Water/ACN with 0.05% TFA, Gradient from 5% to 95% in 1.2 min, hold 0.55 min; 254 nm): 99% purity; 523 [M+H]. mp: 152-154° C.

Example 15: 2-[4-(4-Amino-1-methyl-1H-pyrazolo[3,4-d]pyrimidin-3-yl)-phenyl]-N-[5-tert-butyl-2-(4-isopropyl-phenyl)-2H-pyrazol-3-yl]-acetamide (21)

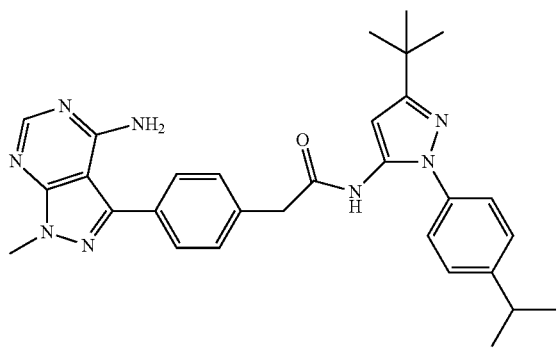 [SMILES: CC(C)c1ccc(-n2nc(C(C)(C)C)cc2NC(=O)Cc2ccc(-c3nn(C)c4ncnc(N)c34)cc2)cc1]

The title compound was obtained following a similar procedure as described for example 9 but starting from N-[3-tert-butyl-1-[4-(propan-2-yl)phenyl]-1H-pyrazol-5-yl]-2-[4-(tetramethyl-1,3,2-dioxaborolan-2-yl)phenyl]acetamide (intermediate 14, 65 mg, 0.09 mmol, 1.0 eq) and 3-iodo-1-methyl-1H-pyrazolo[3,4-d]pyrimidin-4-amine (30 mg, 0.10 mmol, 1.1 eq) as a white solid (15 mg, 32%). 1H NMR (300 MHz, CDCl₃) δ 8.43 (s, 1H), 7.68 (d, J=8.0 Hz, 2H), 7.44-7.34 (m, 3H), 7.24-7.17 (m, 2H), 7.09 (m, 2H), 6.64 (s, 1H), 5.40 (s, 2H), 4.12 (s, 3H), 3.78 (s, 2H), 2.80 (m, 1H), 1.33 (s, 9H), 1.11 (d, J=6.9 Hz, 6H). LC/MS (Column Kinetex EVO C18 100 A, 3.0×50 mm, 2.6 um; water with 5 mM NH₄HCO₃/ACN Gradient from 10% to 95% in 2.0 min, hold 0.5 min; 254 nm): 100% purity; 523.3 [M+H]. mp: 218-219° C.

Example 16: 2-[4-(4-Amino-1-methyl-1H-pyrazolo[3,4-d]pyrimidin-3-yl)-2-fluoro-phenyl]-N-[5-tert-butyl-2-(4-isopropyl-phenyl)-2H-pyrazol-3-yl]-acetamide (19)

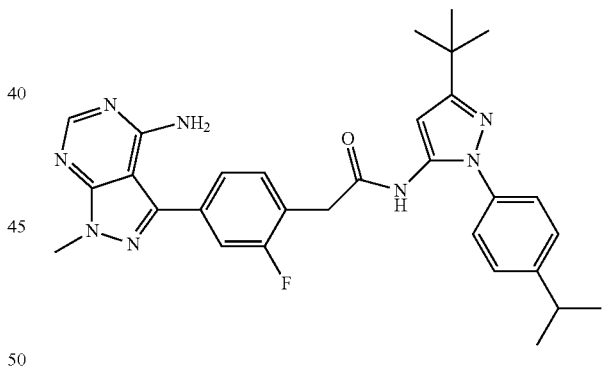

The title compound was obtained following a similar procedure as described for example 9 but starting from N-[3-tert-butyl-1-[4-(propan-2-yl)phenyl]-1H-pyrazol-5-yl]-2-[2-fluoro-4-(tetramethyl-1,3,2-dioxaborolan-2-yl)phenyl]acetamide (300 mg, 0.32 mmol, 1.0 eq) and 3-iodo-1-methyl-1H-pyrazolo[3,4-d]pyrimidin-4-amine (150 mg, 0.38 mmol, 1.2 eq) as a white solid (30 mg, 17%). 1H NMR (400 MHz, CDCl₃) δ 8.41 (s, 1H), 7.54-7.43 (m, 4H), 7.29 (m, 2H), 7.24 (m, 2H), 6.63 (s, 1H), 5.81 (s, 2H), 4.12 (s, 3H), 3.77 (s, 2H), 2.89 (m, 1H), 1.33 (s, 9H), 1.19 (d, J=6.9 Hz, 6H). LC/MS (Column Kinetex EVO C18 100 A, 3.0×50 mm, 2.6 um; water/5 mM NH₄HCO₃/Acetonitrile from 10 to 95%, 254 nm): 100% purity; 541.3 [M+H].

Example 17: 1-(4-{4-amino-1-methyl-1H-pyrazolo [3,4-d]pyrimidin-3-yl}-2-chlorophenyl)-3-[3-(1-hydroxy-2-methylpropan-2-yl)-1-(4-methylphenyl)-1H-pyrazol-5-yl]urea (22)

Step 1: 2-(5-{3-[4-(4-amino-1-methyl-1H-pyrazolo [3,4-d]pyrimidin-3-yl)-2-chloro-phenyl]-ureido}-1-p-tolyl-1H-pyrazol-3-yl)-2-methyl-propyl acetate

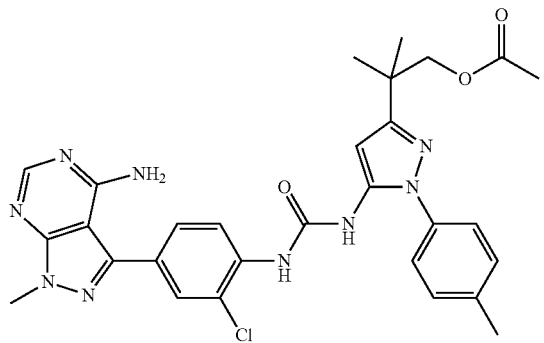 [SMILES: CC(=O)OCC(C)(C)c1cc(NC(=O)Nc2ccc(-c3nn(C)c4ncnc(N)c34)cc2Cl)n(-c2ccc(C)cc2)n1]

The title compound was obtained following a similar procedure as described for example 9 but starting from 2-[5-([[2-chloro-4-(tetramethyl-1,3,2-dioxaborolan-2-yl) phenyl]carbamoyl]amino)-1-(4-methylphenyl)-1H-pyrazol-3-yl]-2-methylpropyl acetate (intermediate 16, 200 mg, 0.35 mmol, 1.00 eq) and 3-iodo-1-methyl-1H-pyrazolo[3,4-d] pyrimidin-4-amine (100 mg, 0.36 mmol, 1.03 eq) as an off-white solid (15 mg, 7%). 1H NMR (400 MHz, DMSO-d6) δ 9.25 (s, 1H), 8.79 (s, 1H), 8.29-8.27 (d, 1H), 8.24 (s, 1H), 7.66-7.65 (d, 1H), 7.57-7.54 (dd, 1H), 7.41-7.39 (d, 2H), 7.36-7.34 (d, 2H), 6.43 (s, 1H), 4.09 (s, 2H), 3.92 (s, 3H), 2.37 (s, 3H), 2.01 (s, 3H), 1.27 (s, 6H). LC/MS (Column Kinetex EVO C18 100 A, 3.0×50 mm, 2.6 um; water with 5 mM NH4HCO3/ACN Gradient from 10% to 95% in 2.0 min, hold 0.5 min; 254 nm): 96% purity; 588.2 [M+H]. mp: 126-128° C.

Step 2: 1-(4-{4-amino-1-methyl-1H-pyrazolo[3,4-d] pyrimidin-3-yl}-2-chlorophenyl)-3-[3-(1-hydroxy-2-methylpropan-2-yl)-1-(4-methylphenyl)-1H-pyrazol-5-yl]urea

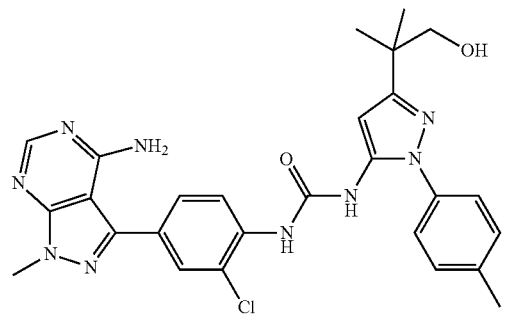

A solution of 2-(5-[[(4-[4-amino-1-methyl-1H-pyrazolo [3,4-d]pyrimidin-3-yl]-2-chlorophenyl)carbamoyl]amino]-1-(4-methylphenyl)-1H-pyrazol-3-yl)-2-methylpropyl acetate (100 mg, 0.15 mmol, 1.00 eq) and potassium carbonate (33 mg, 0.23 mmol, 1.5 eq) in MeOH (5 mL) was stirred for 2 h at RT. Solvent was removed under reduced pressure. Purification by Preparative HPLC (Column Gemini-NX C18 AXAI Packed, 21.2×150 mm, 5um, Water with 0.05% NH4OH/ACN from 33% to 46% in 8 min) afforded the title compound as a white solid (10 mg, 12%). 1H NMR (300 MHz, DMSO-d6) δ 9.22 (s, 1H), 8.78 (s, 1H), 8.30 (d, J=8.6 Hz, 1H), 8.26 (s, 1H), 7.67 (d, J=2.0 Hz, 1H), 7.57 (dd, J=8.6, 2.1 Hz, 1H), 7.45-7.33 (m, 4H), 6.91 (s, 1H), 6.39 (s, 1H), 4.62 (t, J=5.5 Hz, 1H), 3.94 (s, 3H), 3.44 (d, J=5.1 Hz, 2H), 2.38 (s, 3H), 1.22 (s, 6H). LC/MS (Column Kinetex EVO C18 100 A, 3.0×50 mm, 2.6 um; water with 5 mM NH4HCO3/ACN Gradient from 10% to 95% in 2.0 min, hold 0.5 min; 254 nm): 98% (purity); 546.3 [M+H], mp: 192-194° C.

Example 18: 1-(4-{4-amino-1-methyl-1H-pyrazolo [3,4-d]pyrimidin-3-yl}-2-chlorophenyl)-3-[3-(3-methyloxetan-3-yl)-1-(4-methylphenyl)-1H-pyrazol-5-yl]urea (24)

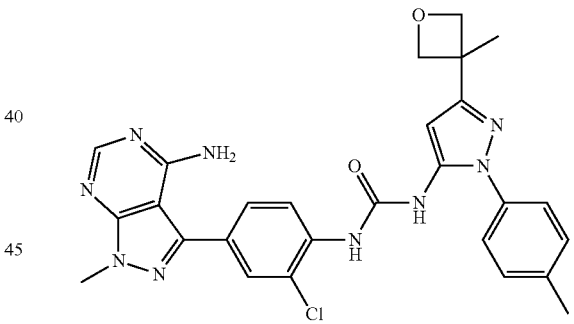

The title compound was obtained following a similar procedure as described for example 9 but starting from 1-[2-chloro-4-(tetramethyl-1,3,2-dioxaborolan-2-yl)phenyl]-3-[3-(3-methyloxetan-3-yl)-1-(4-methylphenyl)-1H-pyrazol-5-yl]urea (intermediate 18, 120 mg, 0.18 mmol, 1.0 eq) and 3-iodo-1-methyl-1H-pyrazolo[3,4-d]pyrimidin-4-amine (intermediate 17, 68 mg, 0.22 mmol, 1.2 eq) as a white solid (10 mg, 10%). 1H NMR (300 MHz, DMSO-d6) δ 9.32 (s, 1H), 8.83 (s, 1H), 8.30 (d, J=8.6 Hz, 1H), 8.26 (s, 1H), 7.68 (d, J=2.0 Hz, 1H), 7.58 (dd, J=8.5, 2.0 Hz, 1H), 7.41 (d, 4H), 6.93 (s, 1H), 6.54 (s, 1H), 4.85 (d, J=5.3 Hz, 2H), 4.47 (d, J=5.4 Hz, 2H), 3.94 (s, 3H), 2.40 (s, 3H), 1.67 (s, 3H). LC/MS (Column Shim-pack XR-ODS, 3.0×50 mm, 2.2 um; Water/CAN with 0.05% TFA, Gradient from 5 to 100% in 2.2 min, hold 1.0 min; 254 nm): 95% purity; 544.2 [M+H]. mp: 170-172° C.

Example 19: 2-[4-(4-Amino-1-methyl-1H-pyrazolo[3,4-d]pyrimidin-3-yl)-phenyl]-N-(5-tert-butyl-2-p-tolyl-2H-pyrazol-3-yl)-2-hydroxy-acetamide (17)

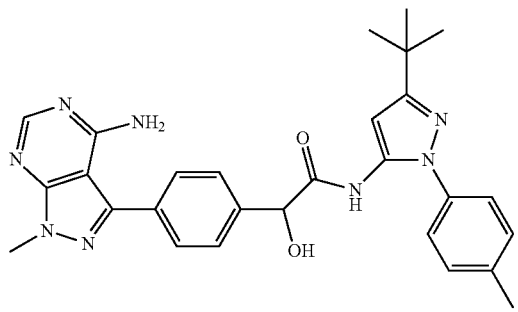

The title compound was obtained following a similar procedure as described for example 9 but starting from N-[3-tert-butyl-1-(4-methylphenyl)-1H-pyrazol-5-yl]-2-hydroxy-2-[4-(tetramethyl-1,3,2-dioxaborolan-2-yl)phenyl]acetamide (intermediate 19, 40 mg, 0.07 mmol, 1.0 eq) and 3-iodo-1-methyl-1H-pyrazolo[3,4-d]pyrimidin-4-amine (22 mg, 0.07 mmol, 1.10 eq) as a white solid (21 mg, 62%). 1H NMR (300 MHz, DMSO-d6) δ 9.87 (s, 1H), 8.28 (s, 1H), 7.65 (d, J=8.2 Hz, 2H), 7.55 (d, J=8.1 Hz, 2H), 7.34-7.24 (m, 2H), 7.19 (d, J=8.3 Hz, 2H), 6.66-6.57 (m, 1H), 6.30 (s, 1H), 5.18-5.12 (m, 1H), 3.97 (s, 3H), 2.30 (s, 3H), 1.26 (s, 9H). LC/MS (Column Shim-pack XR-ODS, 3.0×50 mm, 2.2 um; Water/ACN with 0.05% TFA Gradient from 5% to 100% in 2.2 min, hold 1.0 min; 254 nm): 99% purity; 511.3 [M+H]. mp: 260-262° C.

Example 20: 2-[4-(4-Amino-1-methyl-1H-pyrazolo[3,4-d]pyrimidin-3-yl)-phenyl]-N-(5-tert-butyl-2-p-tolyl-2H-pyrazol-3-yl)-2-oxo-acetamide (7)

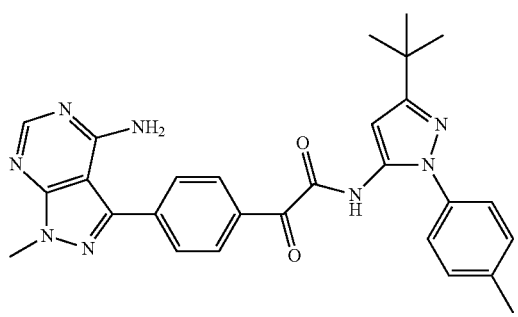

A solution of 2-(4-[4-amino-1-methyl-1H-pyrazolo[3,4-d]pyrimidin-3-yl]phenyl)-N-[3-tert-butyl-1-(4-methylphenyl)-1H-pyrazol-5-yl]-2-hydroxyacetamide (50 mg, 0.09 mmol, 1.0 eq) and IBX (52 mg, 0.18 mmol, 2.0 eq) in DMSO (1 mL) was stirred for 4 h at 20° C. Purification by Prep-HPLC (Column Gemini-NX C18 AXAI Packed, 21.2× 150 mm, 5um, Water with 0.05% NH₄OH/ACN gradient from 50% to 62% in 8 min) afforded the title compound as a yellow solid (20 mg, 44%). 1H NMR (300 MHz, DMSO-d6) δ 10.99 (s, 1H), 8.30 (s, 1H), 8.00 (d, J=8.4 Hz, 2H), 7.84 (d, J=8.4 Hz, 2H), 7.40 (d, J=8.4 Hz, 2H), 7.32 (d, J=8.3 Hz, 2H), 7.05 (s, 2H), 6.53 (s, 1H), 3.99 (s, 3H), 2.37 (s, 3H), 1.32 (s, 9H). LC/MS (Column Phenomenex Gemini-NX C18 3.0×50 mm, 3.0 um; Water with 6.5 mM NH₄HCO₃/ACN, Gradient from 5% to 95% in 2.2 min, hold 1.0 min; 254 nm): 99% purity; 509.1 [M+H].

Example 21: 1-(4-{4-aminothieno[2,3-d]pyrimidin-5-yl}-2-chlorophenyl)-3-[3-(1-hydroxy-2-methylpropan-2-yl)-1-(4-methylphenyl)-1H-pyrazol-5-yl]urea (27)

Step 1: 2-(5-{3-[4-(4-amino-thieno[2,3-d]pyrimidin-5-yl)-2-chloro-phenyl]-ureido}-1-p-tolyl-1H-pyrazol-3-yl)-2-methyl-propyl acetate

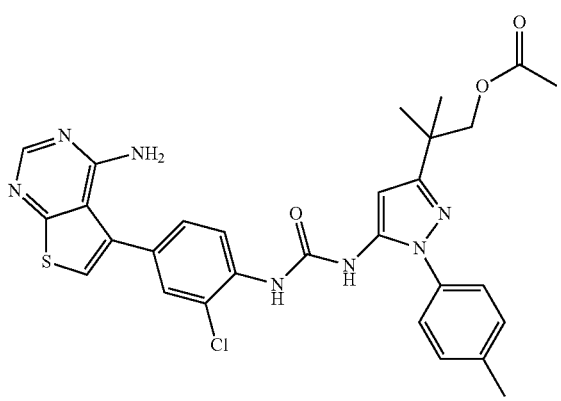 [SMILES: CC(=O)OCC(C)(C)c1cc(NC(=O)Nc2ccc(-c3csc4ncnc(N)c34)cc2Cl)n(-c2ccc(C)cc2)n1]

The title compound was obtained following a similar procedure as described for example 1 but starting from 2-(5-amino-1-p-tolyl-1H-pyrazol-3-yl)-2-methyl-propyl ester (prepared as described in Journal of Medicinal Chemistry, 46(22), 4676-4686; 2003; 208 mg; 0.72 mmol; 1.0 eq) and 5-(4-Amino-3-chloro-phenyl)-thieno[2,3-d]pyrimidin-4-ylamine (intermediate 10; 200 mg; 0.72 mmol; 1.0 eq) as a white solid (40 mg, 9%). 1H NMR (400 MHz, DMSO-d6) δ 9.24 (s, 1H), 8.78 (s, 1H), 8.35 (s, 1H), 8.25 (d, J=8.6 Hz, 1H), 7.63-7.27 (m, 7H), 6.45 (s, 1H), 4.12 (s, 2H), 2.39 (s, 3H), 2.04 (s, 3H), 1.29 (s, 6H). UPLC/MS 590.3 [M+H].

Step 2: 1-(4-{4-aminothieno[2,3-d]pyrimidin-5-yl}-2-chlorophenyl)-3-[3-(1-hydroxy-2-methylpropan-2-yl)-1-(4-methylphenyl)-1H-pyrazol-5-yl]urea

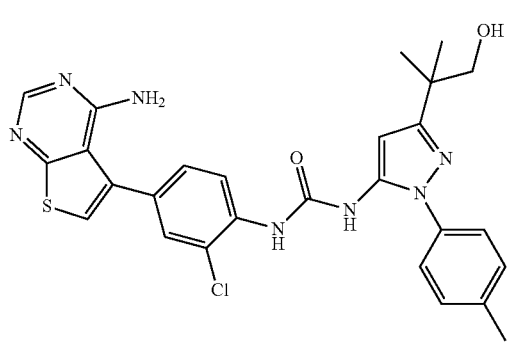 [SMILES: Cc1ccc(-n2nc(C(C)(C)CO)cc2NC(=O)Nc2ccc(-c3csc4ncnc(N)c34)cc2Cl)cc1]

A solution of 2-(5-{3-[4-(4-amino-thieno[2,3-d]pyrimidin-5-yl)-2-chloro-phenyl]-ureido}-1-p-tolyl-1H-pyrazol-3-yl)-2-methyl-propyl ester (40 mg; 0.07 mmol; 1.0 eq) and K₂CO₃ (28 mg, 0.20 mmol; 3 eq) in MeOH (2 mL) was stirred for 1 h at RT. The reaction mixture was then diluted with a saturated solution of sodium bicarbonate (2 mL) and extracted with EtOAc (3×3 mL). Combined organic layers were washed with brine, dried over anhydrous sodium sulfate, filtered and concentrated. Purification by flash chromatography on silica (EP:EtOAc; gradient from 100:0 to 0:100) afforded the title compound as a white solid (27 mg, 73%). 1H NMR (400 MHz, DMSO-d6) δ 9.21 (s, 1H), 8.77 (s, 1H), 8.35 (s, 1H), 8.26 (d, J=8.5 Hz, 1H), 7.57 (d, J=2.1 Hz, 1H), 7.52 (s, 1H), 7.47-7.33 (m, 4H), 6.39 (s, 1H), 4.59 (t, J=5.6 Hz, 1H), 3.45 (d, J=5.5 Hz, 2H), 2.39 (s, 3H), 1.23 (s, 6H). UPLC: (254 nm) 100% purity; Rt 3.13 min. LC/MS: 551.0 [M+H].

Example 22: 1-[4-(4-Amino-thieno[2,3-d]pyrimidin-5-yl)-2-chloro-phenyl]-3-[5-(cyano-dimethyl-methyl)-2-p-tolyl-2H-pyrazol-3-yl]-urea (25)

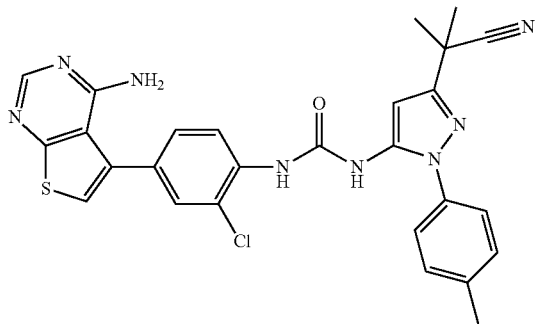 [SMILES: Cc1ccc(-n2nc(C(C)(C)C#N)cc2NC(=O)Nc2ccc(-c3csc4ncnc(N)c34)cc2Cl)cc1]

The title compound was obtained following a similar procedure as described for example 1 but starting from 2-(5-Amino-1-p-tolyl-1H-pyrazol-3-yl)-2-methyl-propionitrile (intermediate 21; 43 mg; 0.18 mmol; 1.0 eq) and 5-(4-Amino-3-chloro-phenyl)-thieno[2,3-d]pyrimidin-4-ylamine (intermediate 10; 50 mg; 0.18 mmol; 1.0 eq) as a white solid (18 mg, 19%). 1H NMR (400 MHz, DMSO-d6) δ 9.36 (s, 1H), 8.86 (s, 1H), 8.35 (s, 1H), 8.26 (d, J=8.5 Hz, 1H), 7.58 (d, J=2.1 Hz, 1H), 7.53 (s, 1H), 7.48-7.38 (m, 5H), 6.62 (s, 1H), 5.76 (s, 1H), 2.42 (s, 3H), 1.71 (s, 6H). UPLC: (254 nm) 99% purity; Rt 3.69 min. UPLC/MS: 543.0 [M+H].

Example 23: 1-[4-(4-Amino-thieno[2,3-d]pyrimidin-5-yl)-2-chloro-3-fluoro-phenyl]-3-(5-tert-butyl-2-p-tolyl-2H-pyrazol-3-yl)-urea (23)

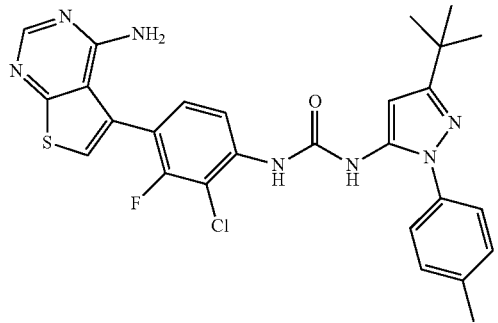 [SMILES: Cc1ccc(-n2nc(C(C)(C)C)cc2NC(=O)Nc2ccc(-c3csc4ncnc(N)c34)c(F)c2Cl)cc1]

The title compound was obtained following a similar procedure as described for example 1 but starting from 5-tert-Butyl-2-p-tolyl-2H-pyrazol-3-ylamine (24 mg; 0.11 mmol; 1.0 eq) and 5-(4-Amino-3-chloro-2-fluoro-phenyl)-thieno[2,3-d]pyrimidin-4-ylamine (intermediate 23; 31 mg; 0.11 mmol; 1.0 eq) as a white solid (3 mg, 5%). 1H NMR (400 MHz, DMSO-d6) δ 9.27 (s, 1H), 8.90 (s, 1H), 8.35 (s, 1H), 8.13 (d, J=8.2 Hz, 1H), 7.59 (s, 1H), 7.48-7.28 (m, 4H), 6.41 (s, 1H), 2.40 (s, 3H), 1.29 (s, 9H). UPLC: (254 nm) 100% purity; Rt 4.02 min. UPLC/MS: 550.0 [M+H].

Example 24: 1-[4-(4-Amino-thieno[2,3-d]pyrimidin-5-yl)-2-chloro-phenyl]-3-[2-p-tolyl-5-(2,2,2-trifluoro-1,1-dimethyl-ethyl)-2H-pyrazol-3-yl]-urea (18)

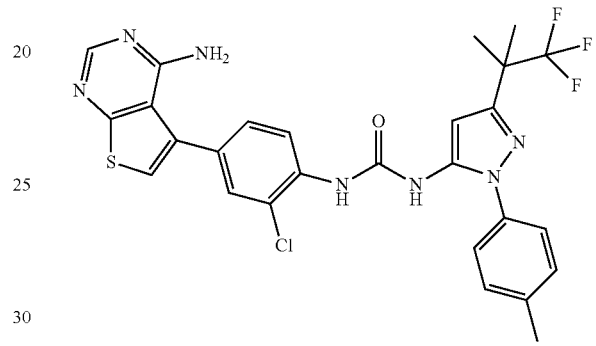

The title compound was obtained following a similar procedure as described for example 1 but starting from 2-p-Tolyl-5-(2,2,2-trifluoro-1,1-dimethyl-ethyl)-2H-pyrazol-3-ylamine (51 mg; 0.18 mmol; 1.0 eq) and 5-(4-Amino-3-chloro-phenyl)-thieno[2,3-d]pyrimidin-4-ylamine (intermediate 10; 50 mg; 0.18 mmol; 1.0 eq) as a white solid (14 mg, 13%). 1H NMR (400 MHz, DMSO-d6) δ 9.32 (s, 1H), 8.83 (s, 1H), 8.35 (s, 1H), 8.26 (d, J=8.6 Hz, 1H), 7.58 (d, J=2.1 Hz, 1H), 7.53 (s, 1H), 7.46 (d, J=8.1 Hz, 2H), 7.42-7.37 (m, 3H), 6.59 (s, 1H), 2.41 (s, 3H), 1.53 (s, 6H). UPLC: (254 nm) 100% purity; Rt 4.28 min. LC/MS: 586.0 [M+H].

Example 25: 1-[4-(4-Amino-7-methyl-7H-pyrrolo[2,3-d]pyrimidin-5-yl)-cyclohex-3-enyl]-3-(5-tert-butyl-2-p-tolyl-2H-pyrazol-3-yl)-urea (1)

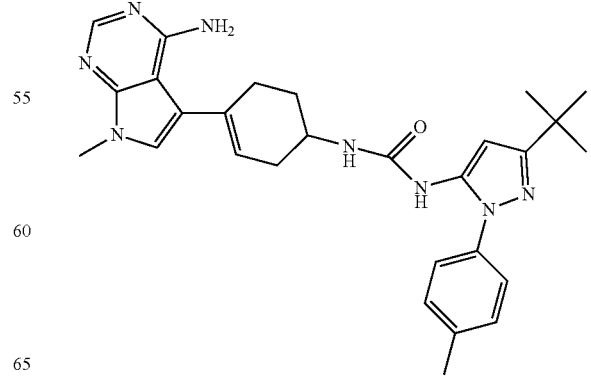

A solution of 3-tert-butyl-1-(4-methylphenyl)-1H-pyrazol-5-amine (94 mg, 0.37 mmol, 1.0 eq) and DIEA (201 mg, 1.48 mmol, 4.0 eq) in DCM (2 mL) was added dropwise to a solution of triphosgene (69 mg, 0.22 mmol, 0.60 eq) in DCM (2 mL) maintained at 0° C. and under nitrogen atmosphere. The reaction mixture was stirred for 2 h at 0° C. before the addition of a solution of 5-(4-aminocyclohex-1-en-1-yl)-7-methyl-7H-pyrrolo[2,3-d]pyrimidin-4-amine (intermediate 24; 100 mg, 0.37 mmol, 1.0 eq) in DMF (2 mL). The resulting reaction mixture was stirred for 4 h at RT and diluted with DCM (10 mL). It was washed with a saturated solution of NH₄Cl (2×10 mL) and brine (1×10 mL), dried over anhydrous sodium sulfate, filtered and concentrated. Purification by Prep-HPLC (Column XBridge BEH130 Prep C18 OBD Column, 19×150 mm, 5um; Water with 0.05% NH₄OH/CAN, 36% ACN for 17 min) afforded the title compound as a white solid (16 mg, 8%). 1H NMR (300 MHz, DMSO-d6) δ 8.09-8.04 (m, 2H), 7.36-7.29 (m, 4H), 7.18 (s, 1H), 6.68-6.65 (m, 1H), 6.29-6.25 (m, 3H), 5.62 (s, 1H), 3.85-3.81 (m, 1H), 3.66 (s, 3H), 2.49-2.43 (m, 3H), 2.36 (s, 3H), 2.08-2.01 (m, 1H), 1.91-1.88 (m, 1H), 1.68-1.62 (m, 1H), 1.25 (s, 9H). LC/MS (Column Ascentis Express C18, 3.0×50 mm, 2.7 um; Water/ACN with 0.05% TFA, Gradient 5% to 100% in 1.2 min, hold 0.5 min; 254 nm): 96% purity; 499.3 [M+H]. mp: 145-147° C.

Example 26: 1-[4-(4-Amino-1-methyl-1H-pyrazolo[4,3-c]pyridin-3-yl)-2-fluoro-phenyl]-3-(5-tert-butyl-2-p-tolyl-2H-pyrazol-3-yl)-urea (3)

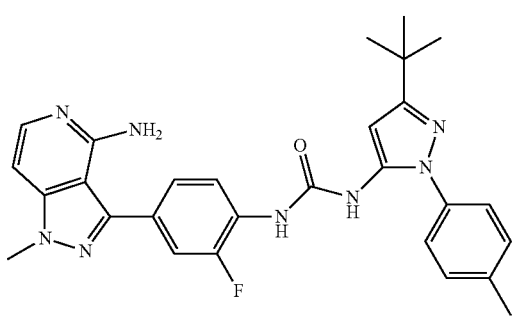

The title compound was obtained following a similar procedure as described for example 9 but starting from 3-[3-tert-butyl-1-(4-methylphenyl)-1H-pyrazol-5-yl]-1-[2-fluoro-4-(tetramethyl-1,3,2-dioxaborolan-2-yl)phenyl]urea (intermediate 25, 150 mg, 0.27 mmol, 1.0 eq) and 3-iodo-1-methyl-1H-pyrazolo[4,3-c]pyridin-4-amine (intermediate 12, 894 mg, 3.1 mmol, 11.3 eq) as a white solid (10 mg, 7%). 1H NMR (300 MHz, DMSO-d6) δ 9.09 (s, 1H), 8.86 (s, 1H), 8.27 (t, J=8.4 Hz, 1H), 7.73 (d, J=6.1 Hz, 1H), 7.49-7.27 (m, 6H), 6.82 (d, J=6.0 Hz, 1H), 6.38 (s, 1H), 5.79 (s, 2H), 3.93 (s, 3H), 2.36 (s, 3H), 2.04 (s, 1H), 1.25 (s, 10H). LC/MS (Column Poroshell HPH-C18, 3.0×50 mm, 2.7 um; Water with 5 mM NH₄HCO₃/ACN, Gradient from 10% to 95% in 2.2 min, hold 1.0 min; 254 nm): 100% purity; 513.0 [M+H].

Example 27: 3-[3-tert-butyl-1-(4-methylphenyl)-1H-pyrazol-5-yl]-1-[(1s,4s)-4-{4-amino-7-methyl-7H-pyrrolo[2,3-d]pyrimidin-5-yl}cyclohexyl]urea (5)

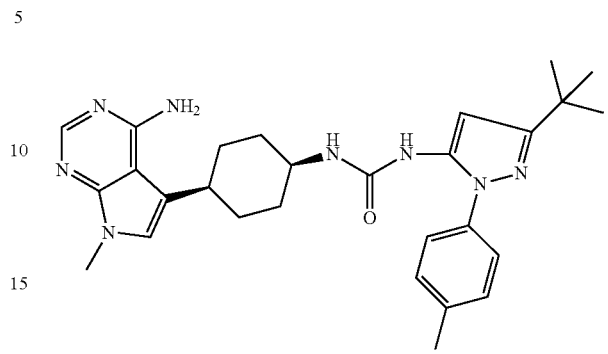

A solution of 1-(4-[4-amino-7-methyl-7H-pyrrolo[2,3-d]pyrimidin-5-yl]cyclohex-3-en-1-yl)-3-[3-tert-butyl-1-(4-methylphenyl)-1H-pyrazol-5-yl]urea (60 mg, 0.11 mmol, 1.0 eq) in MeOH (5 mL) was hydrogenated (1 atm) for 48 h in presence of Palladium on carbon (20 mg). The reaction mixture was then filtrated through a Celite pad and concentrated under reduced pressure. Purification by Prep-HPLC (Column X-Bridge Prep C18 OBD Column, 19×150 mm, 5 um, Water with 10 mM NH₄CO₃+0.1% NH₄OH/ACN, gradient from 38.0% to 40.0% in 20 min) afforded the title compound as a white solid (9.9 mg, 17%). 1H NMR (300 MHz, DMSO-d6): δ 8.05-8.03 (m, 2H), 7.36-7.30 (m, 4H), 6.83 (s, 1H), 6.74-6.71 (m, 1H), 6.43 (s, 2H), 6.29 (s, 1H), 3.86 (m, 1H), 3.58 (s, 3H), 2.97 (s, 1H), 2.32 (s, 3H), 2.01-1.56 (m, 6H), 1.40 (m, 2H), 1.21 (s, 9H). LC/MS (Column Shim-pack XR-ODS, 3.0×50 mm, 2.2 um; Water/CAN with 0.05% TFA, Gradient from 5% to 100% in 2.0 min, hold 0.7 min; 254 nm): 95% purity; 501.3 [M+H]. mp: 228-230° C.

Example 28: 1-(4-{4-amino-1-methyl-1H-pyrazolo[3,4-d]pyrimidin-3-yl}-2-chlorophenyl)-3-[3-tert-butyl-1-(4-cyanophenyl)-1H-pyrazol-5-yl]urea (28)

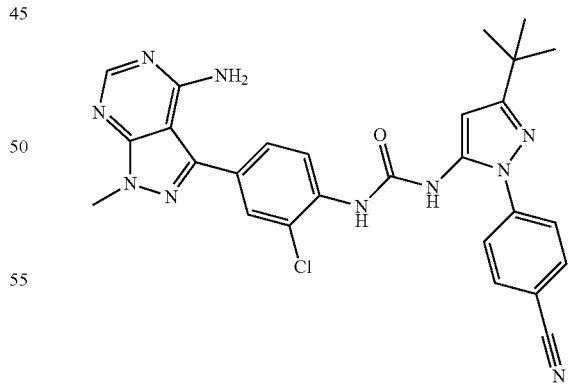

The title compound was obtained following a similar procedure as described for example 1 but starting from 4-[5-Amino-3-(1,1-dimethylethyl)-1H-pyrazol-1-yl]benzonitrile as a beige solid. 1H NMR (400 MH DMSO-d6) δ 1.30 (s, 9H), 3.99 (s, 3H), 5.76 (s, 1H), 7.55 (d, J=8.6 Hz, 1H), 7.69 (d, J=1.6 Hz, 1H), 7.77 (d, J=7.2 Hz, 2H), 7.98 (d, J=7.2 Hz, 2H), 8.20 (d, =8.5 Hz, 1H), 8.39 (s, 1H), 8.80 (s, 1H), 9.43 (s, 1H). HPLC (Atlantis dC18, 254×4.6 mm, 5um, gradient TFA 0.1% in water/ACN 10% to 100% in 15 min, 254 nm) 98.0% purity; Rt 12.7 min. LC/MS (ESI−): 539.0 [M−H].

Example 29: 1-[4-(4-Amino-1-methyl-1H-pyrazolo[3,4-d]pyrimidin-3-yl)-2-chloro-phenyl]-3-[5-tert-butyl-2-(3-fluoro-4-methyl-phenyl)-2H-pyrazol-3-yl]-urea (29)

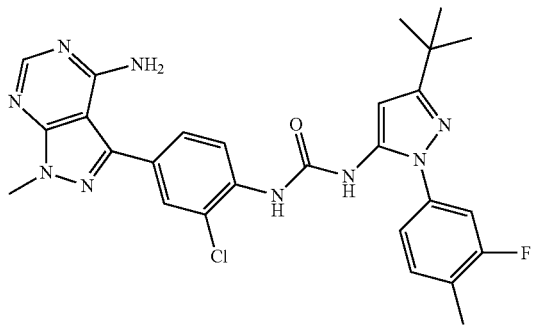 [SMILES: Cc1ccc(-n2nc(C(C)(C)C)cc2NC(=O)Nc2ccc(-c3nn(C)c4ncnc(N)c34)cc2Cl)cc1F]

The title compound was obtained following a similar procedure as described for example 1 but starting from 5-tert-Butyl-2-(3-fluoro-4-methyl-phenyl)-2H-pyrazol-3-ylamine as a beige solid. 1H NMR (400 MH, DMSO-d6) δ 1.28 (s, 9H), 2.29 (s, 3H), 3.98 (s, 3H), 4.5 (brs, 2H), 6.41 (s, 1H), 7.30 (d, J=8.1 Hz, 1H), 7.37 (d, J=11.8 Hz, 1H), 7.45 (t, J=8.3 Hz, 1H), 7.57 (d, J=8.6 Hz, 1H), 7.69 (d, J=1.4 Hz, 1H), 8.29 (d, J=8.6 Hz, 1H), 8.80 (s, 1H), 9.28 (s, 1H). HPLC: (Atlantis dC18, 254×4.6 mm, 5 um, gradient TFA 0.1% in water/ACN 10% to 100% in 15 min, 254 nm) 97.3% purity; Rt 13.3 min. LC/MS (ESI−): 546.0 [M−H].

Example 30: Enzymatic and Cellular Assays

IRAK4 Enzymatic Assay:

IRAK4 is a human purified recombinant enzyme (His-TEV-IRAK4 (1-460)). In this assay, IRAK4 hydrolysed ATP, autophosphorylated and phosphorylated a Serine/Threonine generic peptidic substrate (STK: 61ST1BLC from CisBio International). Measurement of IRAK-4 inhibition was performed in 384-well format based on a luminescence assay (ADP-Glo™ Kinase Assay from Promega). Purified human recombinant IRAK4 (0.3 μg/ml) and serial diluted compounds in DMSO (range of concentration from 10 μM to 0.5 nM) or controls (1% DMSO) were incubated for 15 minutes at RT in assay buffer containing 50 mM Hepes pH 7.0, Fatty acid-free BSA 0.1%, Dithiothreitol (DTT) 2 mM, MgCl2 10 mM, EGTA 0.5 mM, Triton X-100 0.01%, MnCl2 5 mM. The kinase reaction was then initiated by the addition of ATP (2 μM) and the peptidic substrate STK1-biotin peptide (300 nM). After 2 hours of incubation at RT, the reaction was stopped and the unconsumed ATP depleted by the addition of ADP-Glo™ Reagent according to supplier instructions. After 40 minutes of incubation at RT, the Kinase Detection Reagent was then added to the assay plate according to supplier instructions. After 20 minutes of incubation at RT, the luminescence signal was measured with a plate-reading luminometer (PerkinElmer Envision or equivalent reader).

IRAK1 Enzymatic Assay:

IRAK1 is a human purified recombinant enzyme (His-TEV-IRAK1 (194-712)). In this assay, IRAK1 hydrolysed ATP and autophosphorylated. Measurement of IRAK-1 inhibition was performed in 384-well format based on luminescence assay (ADP-Glo™ Kinase Assay from Promega). Purified human recombinant IRAK1 (0.3 μg/ml) and serial diluted compounds in DMSO (range of concentration from 10 μM to 0.5 nM) or controls (1% DMSO) were incubated for 15 minutes at RT in assay buffer containing 50 mM Hepes pH 7.0, Fatty acid-free BSA 0.1%, Dithiothreitol (DTT) 2 mM, MgCl2 10 mM, EGTA 0.5 mM, Triton X-100 0.01%. The kinase reaction was then initiated by the addition of ATP at a concentration of 1 μM. After 2 hours of incubation at RT, the reaction was stopped and the unconsumed ATP depleted by the addition of ADP-Glo™ Reagent according to supplier instructions. After 40 minutes of incubation at RT, the Kinase Detection Reagent was then added to the assay plate according to supplier instructions. After 20 minutes of incubation at RT, the luminescence signal was measured with a luminometer (PerkinElmer Envision or equivalent reader).

TLR7 Induced IL-6 in Human PBMC's

Human PBMC assay was used as one of the functional assays to monitor the activity of IRAK1 and IRAK4 small molecule inhibitors on TLR7 induced IL-6 secretion in human mononuclear cells (PBMC's). Human PBMCs were prepared from buffy coats (whole blood enriched with leukocytes and platelets) obtained from healthy volunteers used either fresh or frozen were plated in assay media (RPMI+2% P/S/L-glu+10% HI-FBS) and pre-treated with compounds in DMSO/media (range of concentrations from 25 uM to 0.4 nM) or controls (0.25% DMSO) for 30 minutes at 37° C. in assay media. Following pre-treatment with IRAK1 and IRAK4 inhibitors, PBMC's were stimulated with TLR7 specific ligand (2 uM) overnight (16-18 hrs) at 37° C. After incubation supernatant was transferred to 384 well PE AlphaPlate-384 and IL-6 was quantified using Perkin Elmer IL-6 Alpha LISA kit (AL223C). Plates were read on an Envision® plate reader with Alpha Technology®.

Results are given in the following table.

| Example | Compound | IRAK1 | IRAK4 | PBMC |
|---|---|---|---|---|
| 1 | 15 | **** | *** | **** |
| 2 | 2 | **** | **** | **** |
| 3 | 11 | **** | *** | **** |
| 4 | 6 | **** | **** | **** |
| 5 | 4 | **** | **** | **** |
| 6 | 12 | **** | *** | **** |
| 7 | 9 | **** | **** | **** |
| 8 | 8 | **** | **** | **** |
| 9 | 10 | **** | **** | **** |
| 10 | 14 | **** | *** | **** |
| 11 | 20 | **** | ** | **** |
| 12 | 13 | **** | *** | **** |
| 13 | 26 | *** | * | *** |
| 14 | 16 | **** | *** | **** |
| 15 | 21 | **** | ** | ** |
| 16 | 19 | **** | *** | ** |
| 17 | 22 | **** | ** | **** |
| 18 | 24 | **** | ** | *** |
| 19 | 17 | **** | *** | *** |
| 20 | 7 | **** | **** | ** |
| 21 | 27 | *** | * | * |
| 22 | 25 | *** | ** | * |
| 23 | 23 | **** | ** | **** |
| 24 | 18 | **** | *** | **** |
| 25 | 1 | **** | **** | NT |
| 26 | 3 | **** | *** | **** |

-continued

| Example | Compound | IRAK1 | IRAK4 | PBMC |
|---|---|---|---|---|
| 27 | 5 | *** | ** | NT |
| 28 | 28 | **** | *** | NT |
| 29 | 29 | **** | *** | NT |

\* $IC_{50}$ >5 μM
\*\* $IC_{50}$ ranges from 1 μM-5 μM
\*\*\* $IC_{50}$ ranges from 100 nM-1.0 μM
\*\*\*\* $IC_{50}$ <100 nM
NT Not Tested Example 31: Pharmaceutical Preparations (A) Injection vials: A solution of 100 g of an active ingredient according to the invention and 5 g of disodium hydrogen phosphate in 3 l of bidistilled water is adjusted to pH 6.5 using 2 N hydrochloric acid, sterile filtered, transferred into injection vials, is lyophilized under sterile conditions and is sealed under sterile conditions. Each injection vial contains 5 mg of active ingredient.

(B) Suppositories: A mixture of 20 g of an active ingredient according to the invention is melted with 100 g of soy lecithin and 1400 g of cocoa butter, is poured into moulds and is allowed to cool. Each suppository contains 20 mg of active ingredient.

(C) Solution: A solution is prepared from 1 g of an active ingredient according to the invention, 9.38 g of $NaH_2PO_4 \cdot 2H_2O$, 28.48 g of $Na_2HPO_4 \cdot 12H_2O$ and 0.1 g of benzalkonium chloride in 940 ml of bidistilled water. The pH is adjusted to 6.8, and the solution is made up to 1 l and sterilized by irradiation. This solution could be used in the form of eye drops.

(D) Ointment: 500 mg of an active ingredient according to the invention is mixed with 99.5 g of Vaseline under aseptic conditions.

(E) Tablets: A mixture of 1 kg of an active ingredient according to the invention, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

(F) Coated tablets: Tablets are pressed analogously to Example E and subsequently are coated in a conventional manner with a coating of sucrose, potato starch, talc, tragacanth and dye.

(G) Capsules: 2 kg of an active ingredient according to the invention are introduced into hard gelatin capsules in a conventional manner in such a way that each capsule contains 20 mg of the active ingredient.

(H) Ampoules: A solution of 1 kg of an active ingredient according to the invention in 60 l of bidistilled water is sterile filtered, transferred into ampoules, is lyophilized under sterile conditions and is sealed under sterile conditions. Each ampoule contains 10 mg of active ingredient.

(I) Inhalation spray: 14 g of an active ingredient according to the invention are dissolved in 10 l of isotonic NaCl solution, and the solution is transferred into commercially available spray containers with a pump mechanism. The solution could be sprayed into the mouth or nose. One spray shot (about 0.1 ml) corresponds to a dose of about 0.14 mg.

While a number of embodiments of this invention are described herein, it is apparent that the basic examples may be altered to provide other embodiments that utilize the compounds and methods of this invention. Therefore, it will be appreciated that the scope of this invention is to be defined by the appended claims rather than by the specific embodiments that have been represented by way of example.

We claim:
1. A compound of Formula I:

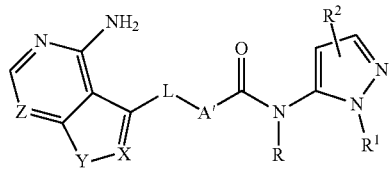

or a pharmaceutically acceptable salt or stereoisomer thereof,
wherein:
X is CR or N;
Y is —NR— or —S—;
Z is CR or N;
L is:

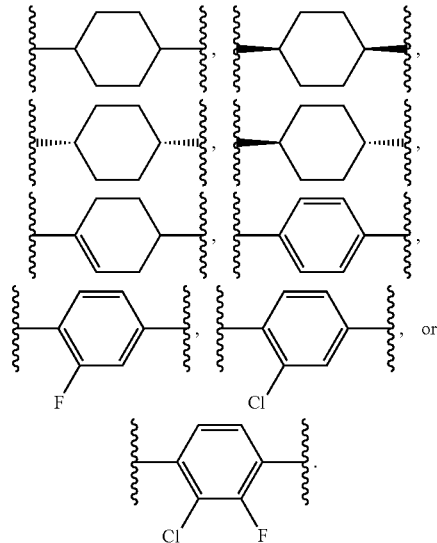

$A'$ is —CRR—, —CHOH—, —C(O)—, or —NR—;
$R^1$ is:

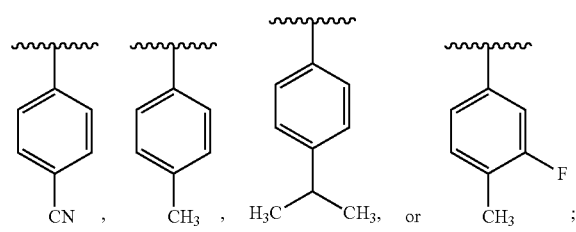

$R^2$ is $CF_3$, $C(CH_3)_2CN$, $C(CH_3)_3$, $C(CH_3)_2CF_3$, $C(CH_3)_2CH_2OH$, or 3-methyloxetan-3-yl; and
each R is independently hydrogen, $C_{1-6}$ aliphatic, a saturated or partially unsaturated 3- to 8-membered carbocyclic ring, a 3- to 7-membered heterocyclic ring, $C_{6-10}$ aryl, or a monocyclic 5- or 6-membered heteroaryl, wherein each 3- to 7-membered heterocyclic ring and 5- or 6-membered heteroaryl independently contains 1, 2, 3, or 4 heteroatoms independently selected from the group consisting of nitrogen, oxygen, and sulfur.

2. The compound of claim 1, or a pharmaceutically acceptable salt or stereoisomer thereof, wherein A' is —CH$_2$—, —CHOH—, —C(O)—, or —NH—.

3. The compound of claim 1, wherein the compound is of Formula I-a:

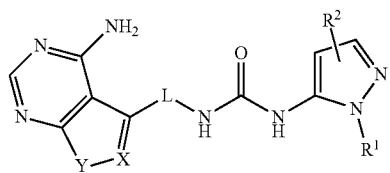

I-a or a pharmaceutically acceptable salt or stereoisomer thereof.

4. The compound of claim 1, wherein the compound is of Formula I-c:

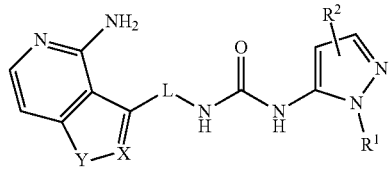

I-c or a pharmaceutically acceptable salt or stereoisomer thereof.

5. The compound of claim 1, wherein the compound is of Formula I-e:

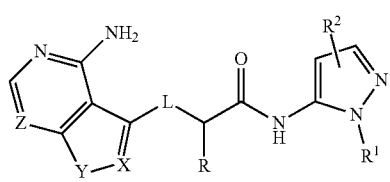

I-e or a pharmaceutically acceptable salt or stereoisomer thereof.

6. The compound of claim 1, wherein the compound is of Formula I-h:

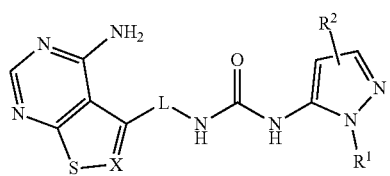

I-h or a pharmaceutically acceptable salt or stereoisomer thereof.

7. The compound of claim 1, or a stereoisomer thereof, wherein the compound, or stereoisomer thereof, is selected from the group consisting of:

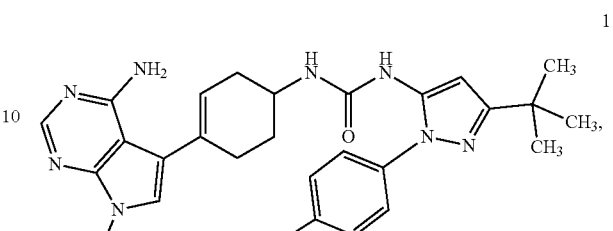

1

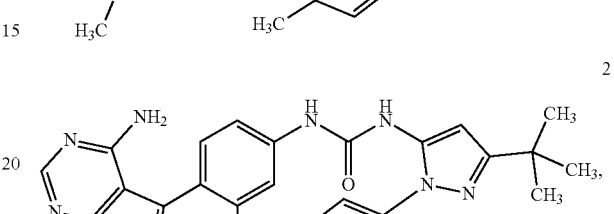

2

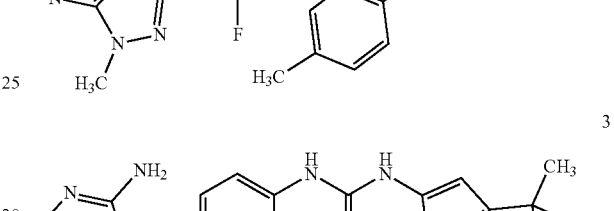

3

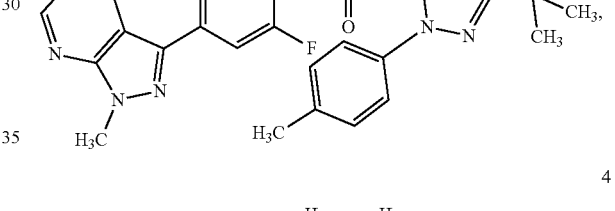

4

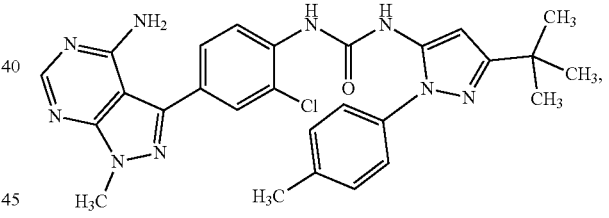

5

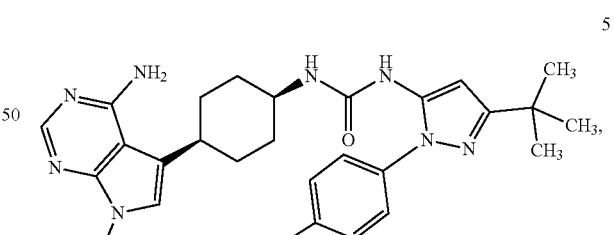

6

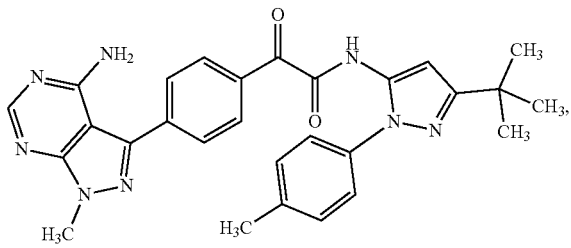
7
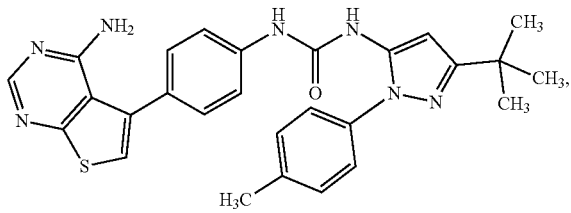
13
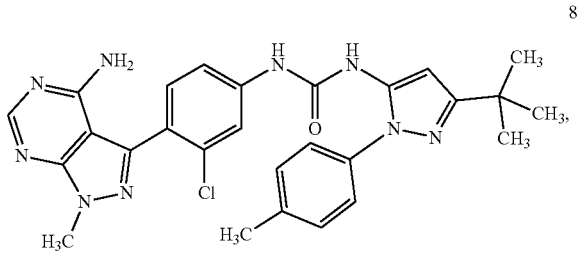
8
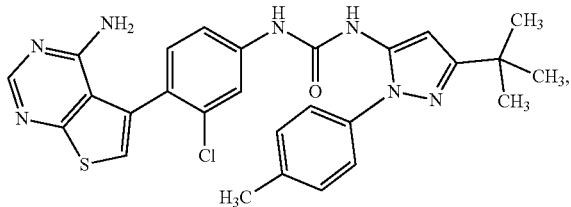
14
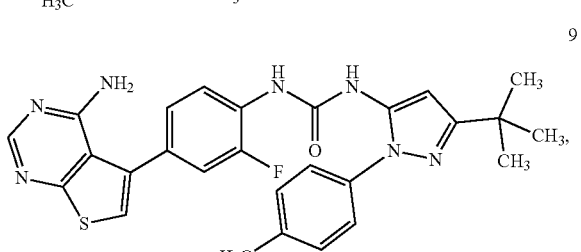
9
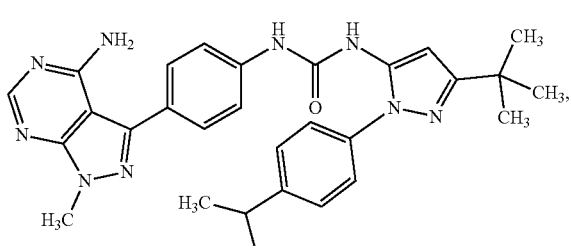
15
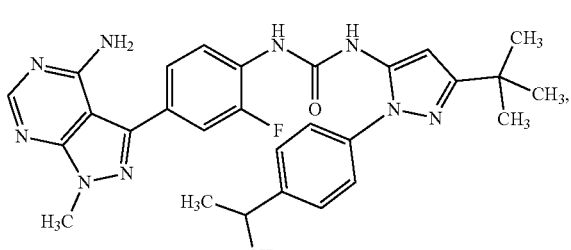
10
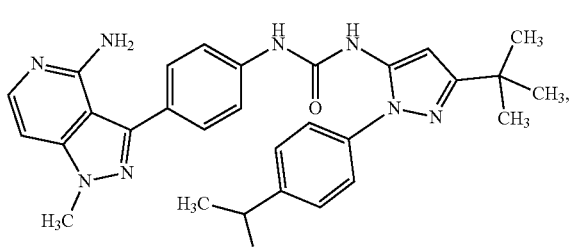
16
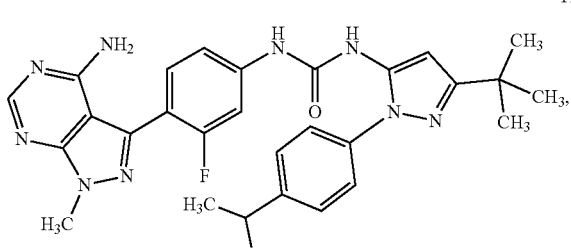
11
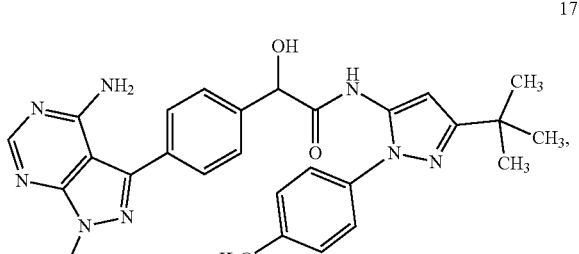
17
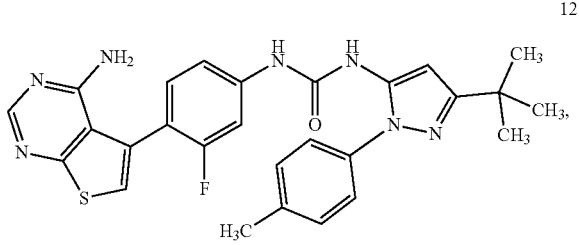
12
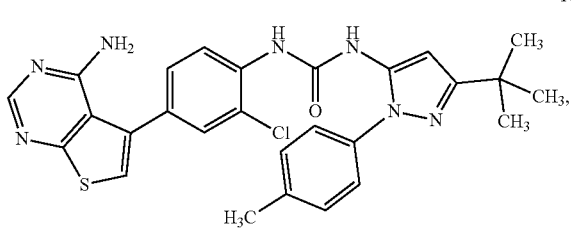
18

19

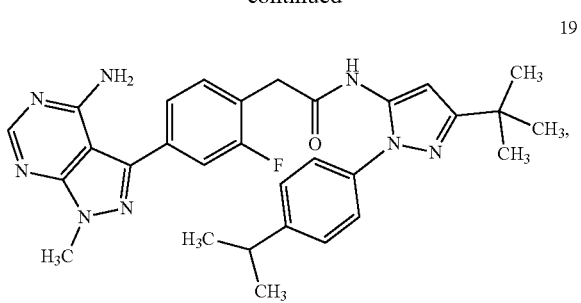

20

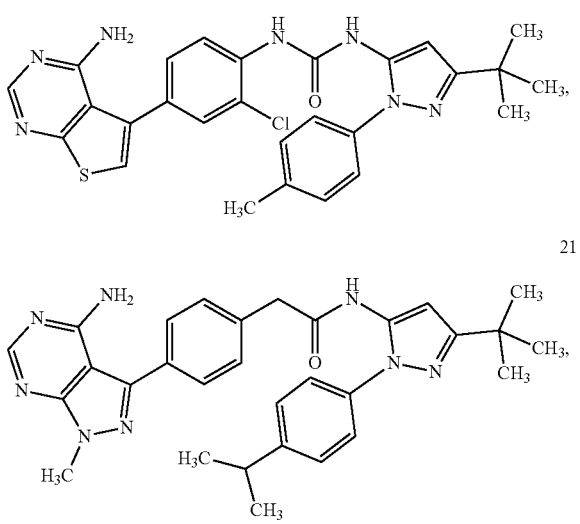

21

22

23

24

25

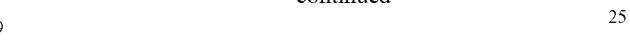

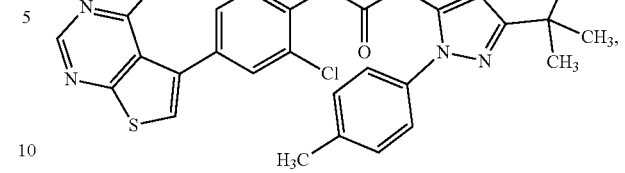

26

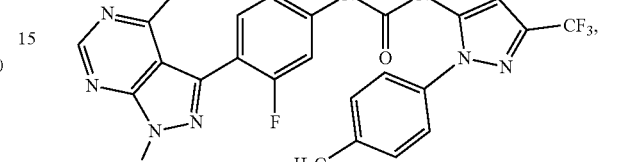

27

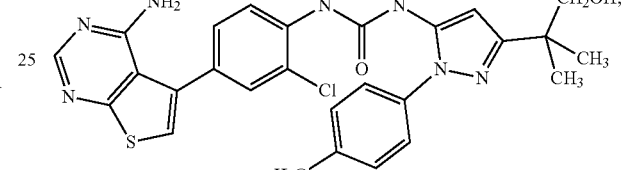

28

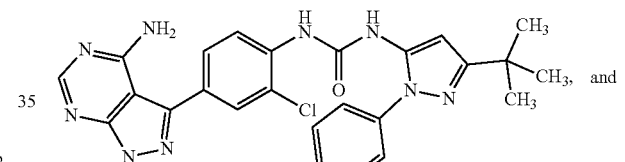

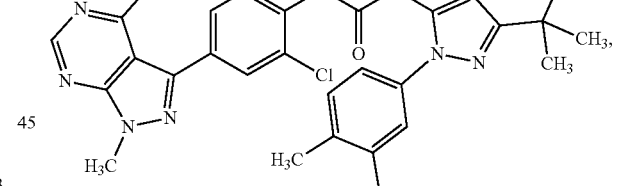

or a pharmaceutically acceptable salt thereof.

8. A pharmaceutical composition comprising a pharmaceutically acceptable adjuvant, carrier, or vehicle and a compound of claim 1, or a pharmaceutically acceptable salt or stereoisomer thereof.

9. A method for inhibiting interleukin-1 receptor associated kinase, or a mutant thereof, activity in a biological sample, wherein the method comprises contacting the biological sample with a compound of claim 1, or a pharmaceutically acceptable salt or stereoisomer thereof.

10. A method for inhibiting interleukin-1 receptor associated kinase, or a mutant thereof, activity in a patient in need thereof, wherein the method comprises administering to the patient a therapeutically effective amount of a compound of claim 1, or a pharmaceutically acceptable salt or stereoisomer thereof.

11. The method of claim 10, wherein the patient has an interleukin-1 receptor associated kinase-mediated disorder selected from the group consisting of adult onset Still's disease, Alzheimer's disease, ankylosing spondylitis, atherosclerosis, Castleman's disease, celiac disease, a ciyopyrin-associated periodic syndrome, deficiency of interleukin-1 receptor antagonist (DIRA), endometriosis, gout, hyperimmunoglobulinemia D and periodic fever syndrome, inflammatory bowel disease, lupus nephritis, multiple sclerosis, osteoarthritis, osteoporosis, Parkinson's disease, pseudogout, psoriasis, psoriatic arthritis, rheumatoid arthritis, synovitis, acne, pustulosis, hyperostosis, and osteitis (SAPHO) syndrome, Schnitzler's syndrome, sepsis, stroke, systemic lupus erythematosus, systemic juvenile idiopathic arthritis, systemic sclerosis, type I diabetes, and type II diabetes.

12. The method of claim 11, wherein the interleukin-1 receptor associated kinase-mediated disorder is selected from the group consisting of lupus nephritis, multiple sclerosis, rheumatoid arthritis, and systemic lupus erythematosus.

13. The method of claim 11, wherein the inflammatory bowel disease is Crohn's disease or ulcerative colitis.

* * * * *